US012746129B2

(12) United States Patent
Hayes et al.

(10) Patent No.: US 12,746,129 B2
(45) Date of Patent: Sep. 29, 2026

(54) EXPANDABLE CERVICAL INTERBODY AND INSTRUMENTS THEREOF

(71) Applicant: Warsaw Orthopedic, Inc., Warsaw, IN (US)

(72) Inventors: Stanley Kyle Hayes, Mission Viejo, CA (US); Darren L. Davis, Knoxville, TN (US); Patrick Ryan Keene, Youngsville, NC (US); Cristian A. Capote, Memphis, TN (US); John A. Hall, Germantown, TN (US); Robert M. Loke, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 22 days.

(21) Appl. No.: 18/665,521

(22) Filed: May 15, 2024

(65) Prior Publication Data

US 2024/0390157 A1 Nov. 28, 2024

Related U.S. Application Data

(60) Provisional application No. 63/503,859, filed on May 23, 2023.

(51) Int. Cl.

| | |
|---|---|
| ***A61F 2/44*** | (2006.01) |
| ***A61F 2/30*** | (2006.01) |
| ***A61F 2/46*** | (2006.01) |

(52) U.S. Cl.

CPC ........ *A61F 2/4455* (2013.01); *A61F 2/30734* (2013.01); *A61F 2/30771* (2013.01); (Continued)

(58) Field of Classification Search

CPC .................... A61F 2/447; A61F 2/4425; A61F 2002/30471; A61F 2002/30507; A61F 2002/30538

See application file for complete search history.

(56) References Cited

U.S. PATENT DOCUMENTS

| | | | |
|---|---|---|---|
| 1,677,337 | A | 7/1928 | Grove |
| 3,847,154 | A | 11/1974 | Nordin |

(Continued)

FOREIGN PATENT DOCUMENTS

| | | | |
|---|---|---|---|
| CN | 107 137 166 | A | 9/2017 |
| CN | 116056669 | A | 5/2023 |

(Continued)

OTHER PUBLICATIONS

Search Report, and Written Opinion for Application. No. PCT/US2019/019067, dated Jun. 3, 2019.

(Continued)

*Primary Examiner* — Jacqueline T Johanas

(74) *Attorney, Agent, or Firm* — FOX ROTHSCHILD LLP

(57) ABSTRACT

A system including an implant and a tool for inserting and expanding the medical implant and locking the implant in place is disclosed. The medical implant may include an expandable body defined by a superior endplate and an inferior endplate that are hingedly coupled and may be expanded and lordosed. The implant may include a wedge disposed between the superior and inferior endplates that is configured to slide across a channel on inferior endplate and along an inclined groove on superior endplate. In at least some embodiments, an expansion screw is operative coupled to the threaded portion of the wedge that when expansion screw is rotated, the wedge is translated thereby expanding the implant.

19 Claims, 28 Drawing Sheets

(52) U.S. Cl.
CPC ... *A61F 2/4611* (2013.01); *A61F 2002/30471* (2013.01); *A61F 2002/30481* (2013.01); *A61F 2002/30528* (2013.01); *A61F 2002/30579* (2013.01); *A61F 2002/30736* (2013.01); *A61F 2002/30827* (2013.01); *A61F 2002/30884* (2013.01); *A61F 2002/443* (2013.01); *A61F 2002/4622* (2013.01); *A61F 2002/4627* (2013.01); *A61F 2002/4668* (2013.01)

(56) References Cited

U.S. PATENT DOCUMENTS 4,553,273 A 11/1985 Wu
4,636,217 A 1/1987 Ogilvie et al.
4,716,894 A 1/1988 Lazzeri et al.
4,759,769 A 7/1988 Hedman et al.
5,059,193 A 10/1991 Kuslich
5,171,278 A 12/1992 Pisharodi
5,228,811 A 7/1993 Potter
5,284,483 A 2/1994 Johnson et al.
5,336,223 A 8/1994 Rogers
5,390,683 A 2/1995 Pisharodi
5,522,899 A 6/1996 Michelson
5,554,191 A 9/1996 Lahille et al.
5,575,790 A 11/1996 Chen et al.
5,609,635 A 3/1997 Michelson
5,653,762 A 8/1997 Pisharodi
5,653,763 A 8/1997 Errico et al.
5,658,336 A 8/1997 Pisharodi
5,665,122 A 9/1997 Kambin
5,693,100 A 12/1997 Pisharodi
5,697,977 A 12/1997 Pisharodi
5,702,391 A 12/1997 Lin
5,702,453 A 12/1997 Rabbe et al.
5,702,455 A 12/1997 Saggar
5,797,918 A 8/1998 McGuire et al.
5,800,550 A 9/1998 Sertich
5,865,848 A 2/1999 Baker
5,893,890 A 4/1999 Pisharodi
5,931,777 A 8/1999 Sava
5,941,885 A 8/1999 Jackson
5,971,987 A 10/1999 Huxel et al.
5,980,522 A 11/1999 Koros et al.
6,045,579 A 4/2000 Hochshuler et al.
6,074,343 A 6/2000 Nathanson et al.
6,080,193 A 6/2000 Hochshuler et al.
6,099,531 A 8/2000 Bonutti
6,102,949 A 8/2000 Biedermann et al.
6,102,950 A 8/2000 Vaccaro
6,106,557 A 8/2000 Robioneck et al.
6,113,638 A 9/2000 Williams et al.
6,117,174 A 9/2000 Nolan
6,132,465 A 10/2000 Ray et al.
6,159,211 A 12/2000 Boriani et al.
6,159,244 A 12/2000 Suddaby
6,176,882 B1 1/2001 Biedermann et al.
6,179,873 B1 1/2001 Zientek
6,190,414 B1 2/2001 Young et al.
6,193,757 B1 2/2001 Foley et al.
6,217,579 B1 4/2001 Koros
6,245,108 B1 6/2001 Biscup
6,309,421 B1 10/2001 Pisharodi
6,342,074 B1 1/2002 Simpson
6,371,989 B1 4/2002 Chauvin et al.
6,395,031 B1 5/2002 Foley et al.
6,423,063 B1 7/2002 Bonutti
6,432,106 B1 8/2002 Fraser
6,436,140 B1 8/2002 Liu et al.
6,443,989 B1 9/2002 Jackson
6,443,990 B1 9/2002 Aebi et al.
6,454,806 B1 9/2002 Cohen et al.
6,454,807 B1 9/2002 Jackson
6,461,359 B1 10/2002 Tribus et al.
6,475,218 B2 11/2002 Gournay et al.
6,491,724 B1 12/2002 Ferree
6,520,991 B2 2/2003 Huene
6,520,993 B2 2/2003 James et al.
6,524,238 B2 2/2003 Velikaris et al.
6,527,803 B1 3/2003 Crozet et al.
6,562,074 B2 5/2003 Gerbec et al.
6,576,016 B1 6/2003 Hochshuler et al.
6,623,525 B2 9/2003 Ralph et al.
6,629,998 B1 10/2003 Lin
6,635,086 B2 10/2003 Lin
6,648,917 B2 11/2003 Gerbec et al.
6,676,703 B2 1/2004 Biscup
6,685,742 B1 2/2004 Jackson
6,723,126 B1 4/2004 Berry
6,770,096 B2 8/2004 Bolger et al.
6,773,460 B2 8/2004 Jackson
6,821,298 B1 11/2004 Jackson
6,835,206 B2 12/2004 Jackson
6,849,093 B2 2/2005 Michelson
6,852,129 B2 2/2005 Gerbec et al.
6,863,673 B2 3/2005 Gerbec et al.
6,923,814 B1 8/2005 Hildebrand et al.
6,926,737 B2 8/2005 Jackson
6,953,477 B2 10/2005 Berry
6,964,687 B1 11/2005 Bernard et al.
6,974,480 B2 12/2005 Messerli et al.
6,984,234 B2 1/2006 Bray
7,112,222 B2 9/2006 Fraser et al.
7,135,043 B2 11/2006 Nakahara et al.
7,137,997 B2 11/2006 Paul
7,172,627 B2 2/2007 Fiere et al.
7,188,626 B2 3/2007 Foley et al.
7,204,853 B2 4/2007 Gordon et al.
7,232,464 B2 6/2007 Mathieu et al.
7,238,203 B2 7/2007 Bagga et al.
7,255,700 B2 8/2007 Kaiser et al.
7,316,532 B2 1/2008 Matthys-Mark
7,316,714 B2 1/2008 Gordon et al.
7,407,483 B2 8/2008 Perez-Cruet et al.
7,481,766 B2 1/2009 Lee et al.
7,491,168 B2 2/2009 Raymond et al.
7,537,565 B2 5/2009 Bass
7,618,456 B2 11/2009 Mathieu et al.
7,625,394 B2 12/2009 Molz, IV et al.
7,635,366 B2 12/2009 Abdou
7,637,909 B2 12/2009 Lechot et al.
7,655,046 B2 2/2010 Dryer et al.
7,678,148 B2 3/2010 Peterman
7,703,727 B2 4/2010 Selness
7,708,778 B2 5/2010 Gordon et al.
7,708,779 B2 5/2010 Edie et al.
7,727,280 B2 6/2010 McLuen
7,753,958 B2 7/2010 Gordon et al.
7,780,594 B2 8/2010 Hutton
7,806,932 B2 10/2010 Webb et al.
7,815,682 B1 10/2010 Peterson et al.
7,819,801 B2 10/2010 Miles et al.
7,824,428 B2 11/2010 Mikkonen et al.
7,828,849 B2 11/2010 Lim
7,846,167 B2 12/2010 Garcia et al.
7,846,207 B2 12/2010 Lechmann et al.
7,850,731 B2 12/2010 Brittan et al.
7,850,733 B2 12/2010 Baynham et al.
7,862,616 B2 1/2011 Lechmann et al.
7,875,076 B2 1/2011 Mathieu et al.
7,883,542 B2 2/2011 Zipnick
7,892,173 B2 2/2011 Miles et al.
7,909,869 B2 3/2011 Gordon et al.
7,914,559 B2 3/2011 Carls et al.
7,967,821 B2 6/2011 Sicvol et al.
7,981,031 B2 7/2011 Frasier et al.
8,016,836 B2 9/2011 Corrao et al.
8,062,375 B2 11/2011 Glerum et al.
8,105,382 B2 1/2012 Olmos et al.
8,118,870 B2 2/2012 Gordon et al.
8,118,871 B2 2/2012 Gordon et al.
8,123,810 B2 2/2012 Gordon et al.
8,147,550 B2 4/2012 Gordon et al.
8,172,903 B2 5/2012 Gordon et al.
8,182,539 B2 5/2012 Tyber et al.

(56) References Cited

U.S. PATENT DOCUMENTS

| | | | |
|---|---|---|---|
| 8,257,442 | B2 | 9/2012 | Edie et al. |
| 8,262,570 | B2 | 9/2012 | White et al. |
| 8,262,662 | B2 | 9/2012 | Beardsley et al. |
| 8,262,710 | B2 | 9/2012 | Freedman et al. |
| 8,287,597 | B1 | 10/2012 | Pimenta et al. |
| 8,303,498 | B2 | 11/2012 | Miles et al. |
| 8,303,658 | B2 | 11/2012 | Peterman |
| 8,303,663 | B2 | 11/2012 | Jimenez et al. |
| 8,317,866 | B2 | 11/2012 | Palmatier et al. |
| 8,323,185 | B2 | 12/2012 | Perez-Cruet et al. |
| 8,328,872 | B2 | 12/2012 | Duffield et al. |
| 8,343,048 | B2 | 1/2013 | Warren, Jr. |
| 8,353,826 | B2 | 1/2013 | Weiman |
| 8,355,780 | B2 | 1/2013 | Miles et al. |
| 8,382,842 | B2 | 2/2013 | Greenhalgh et al. |
| 8,388,527 | B2 | 3/2013 | Miles et al. |
| 8,398,713 | B2 | 3/2013 | Weiman |
| 8,403,990 | B2 | 3/2013 | Dryer et al. |
| 8,419,797 | B2 | 4/2013 | Biedermann et al. |
| 8,425,528 | B2 | 4/2013 | Berry et al. |
| 8,435,298 | B2 | 5/2013 | Weiman |
| 8,480,576 | B2 | 7/2013 | Sandhu |
| 8,496,706 | B2 | 7/2013 | Ragab et al. |
| 8,500,634 | B2 | 8/2013 | Miles et al. |
| 8,500,749 | B2 | 8/2013 | Lee et al. |
| 8,506,635 | B2 | 8/2013 | Palmatier et al. |
| 8,517,935 | B2 | 8/2013 | Marchek et al. |
| 8,518,120 | B2 | 8/2013 | Glerum et al. |
| 8,535,380 | B2 | 9/2013 | Greenhalgh et al. |
| 8,545,566 | B2 | 10/2013 | Niemiec et al. |
| 8,550,994 | B2 | 10/2013 | Miles et al. |
| 8,556,808 | B2 | 10/2013 | Miles et al. |
| 8,556,979 | B2 | 10/2013 | Glerum et al. |
| 8,579,809 | B2 | 11/2013 | Parker |
| 8,579,898 | B2 | 11/2013 | Prandi et al. |
| 8,579,979 | B2 | 11/2013 | Edie et al. |
| 8,579,981 | B2 | 11/2013 | Lim et al. |
| 8,602,984 | B2 | 12/2013 | Raymond et al. |
| 8,608,785 | B2 | 12/2013 | Reed et al. |
| 8,628,576 | B2 | 1/2014 | Triplett et al. |
| 8,628,578 | B2 | 1/2014 | Miller et al. |
| 8,632,595 | B2 | 1/2014 | Weiman |
| 8,641,768 | B2 | 2/2014 | Duffield et al. |
| 8,647,386 | B2 | 2/2014 | Gordon et al. |
| 8,663,329 | B2 | 3/2014 | Ernst |
| 8,668,419 | B2 | 3/2014 | Hardt et al. |
| 8,668,715 | B2 | 3/2014 | Sandhu |
| 8,679,183 | B2 | 3/2014 | Glerum et al. |
| 8,685,095 | B2 | 4/2014 | Miller et al. |
| 8,685,098 | B2 | 4/2014 | Glerum et al. |
| 8,696,559 | B2 | 4/2014 | Miles et al. |
| 8,709,083 | B2 | 4/2014 | Duffield et al. |
| 8,709,085 | B2 | 4/2014 | Lechmann et al. |
| 8,709,086 | B2 | 4/2014 | Glerum |
| 8,715,285 | B2 | 5/2014 | Lewis et al. |
| 8,715,353 | B2 | 5/2014 | Bagga et al. |
| 8,740,983 | B1 | 6/2014 | Arnold et al. |
| 8,753,271 | B1 | 6/2014 | Miles et al. |
| 8,753,396 | B1 | 6/2014 | Hockett et al. |
| 8,764,649 | B2 | 7/2014 | Miles et al. |
| 8,771,360 | B2 | 7/2014 | Jimenez et al. |
| 8,778,025 | B2 | 7/2014 | Ragab et al. |
| 8,778,027 | B2 | 7/2014 | Medina |
| 8,795,366 | B2 | 8/2014 | Varela |
| 8,808,304 | B2 | 8/2014 | Weiman et al. |
| 8,808,305 | B2 | 8/2014 | Kleiner |
| 8,827,902 | B2 | 9/2014 | Dietze, Jr. et al. |
| 8,828,085 | B1 | 9/2014 | Jensen |
| 8,840,668 | B1 | 9/2014 | Donahoe et al. |
| 8,845,731 | B2 | 9/2014 | Weiman |
| 8,845,732 | B2 | 9/2014 | Weiman |
| 8,845,734 | B2 | 9/2014 | Weiman |
| 8,852,252 | B2 | 10/2014 | Venturini et al. |
| 8,852,282 | B2 | 10/2014 | Farley et al. |
| 8,864,833 | B2 | 10/2014 | Glerum et al. |
| 8,882,813 | B2 | 11/2014 | Jones et al. |
| 8,888,853 | B2 | 11/2014 | Glerum et al. |
| 8,894,708 | B2 | 11/2014 | Thalgott et al. |
| 8,894,711 | B2 | 11/2014 | Varela |
| 8,894,712 | B2 | 11/2014 | Varela |
| 8,906,095 | B2 | 12/2014 | Christensen et al. |
| 8,920,500 | B1 | 12/2014 | Pimenta et al. |
| 8,926,704 | B2 | 1/2015 | Glerum et al. |
| 8,936,641 | B2 | 1/2015 | Cain |
| 8,940,049 | B1 | 1/2015 | Jimenez et al. |
| 8,968,363 | B2 | 3/2015 | Weiman et al. |
| 8,986,344 | B2 | 3/2015 | Sandhu |
| 8,992,425 | B2 | 3/2015 | Karpowicz et al. |
| 8,992,544 | B2 | 3/2015 | Sasing |
| 8,998,906 | B2 | 4/2015 | Kirschman |
| 9,005,292 | B2 | 4/2015 | Melamed |
| 9,005,293 | B2 | 4/2015 | Moskowitz et al. |
| 9,005,295 | B2 | 4/2015 | Kueenzi et al. |
| 9,017,412 | B2 | 4/2015 | Wolters et al. |
| 9,034,045 | B2 | 5/2015 | Davenport et al. |
| 9,050,146 | B2 | 6/2015 | Woolley et al. |
| 9,050,194 | B2 | 6/2015 | Thibodeau |
| 9,060,877 | B2 | 6/2015 | Kleiner |
| 9,072,548 | B2 | 7/2015 | Matityahu |
| 9,072,563 | B2 | 7/2015 | Garcia et al. |
| 9,084,591 | B2 | 7/2015 | Reglos et al. |
| 9,113,854 | B2 | 8/2015 | Ellman |
| 9,119,730 | B2 | 9/2015 | Glerum et al. |
| 9,125,757 | B2 | 9/2015 | Weiman |
| 9,132,021 | B2 | 9/2015 | Mermuys et al. |
| 9,138,217 | B2 | 9/2015 | Smith et al. |
| 9,138,330 | B2 | 9/2015 | Hansell et al. |
| 9,138,331 | B2 | 9/2015 | Aferzon |
| 9,149,367 | B2 | 10/2015 | Davenport et al. |
| 9,155,628 | B2 | 10/2015 | Glerum et al. |
| 9,155,631 | B2 | 10/2015 | Seifert et al. |
| 9,161,841 | B2 | 10/2015 | Kana et al. |
| 9,179,903 | B2 | 11/2015 | Cianfrani et al. |
| 9,179,952 | B2 | 11/2015 | Biedermann et al. |
| 9,186,193 | B2 | 11/2015 | Kleiner et al. |
| 9,186,258 | B2 | 11/2015 | Davenport et al. |
| 9,192,482 | B1 | 11/2015 | Pimenta et al. |
| 9,192,483 | B1 | 11/2015 | Radcliffe et al. |
| 9,198,772 | B2 | 12/2015 | Weiman |
| 9,204,972 | B2 | 12/2015 | Weiman et al. |
| 9,204,974 | B2 | 12/2015 | Glerum et al. |
| 9,211,194 | B2 | 12/2015 | Bagga et al. |
| 9,211,196 | B2 | 12/2015 | Glerum et al. |
| 9,216,095 | B2 | 12/2015 | Glerum et al. |
| 9,226,836 | B2 | 1/2016 | Glerum |
| 9,233,007 | B2 | 1/2016 | Sungarian et al. |
| 9,233,009 | B2 | 1/2016 | Gray et al. |
| 9,233,010 | B2 | 1/2016 | Thalgott et al. |
| 9,259,327 | B2 | 2/2016 | Niemiec et al. |
| 9,271,846 | B2 | 3/2016 | Lim et al. |
| 9,308,099 | B2 | 4/2016 | Triplett et al. |
| 9,320,610 | B2 | 4/2016 | Alheidt et al. |
| 9,351,845 | B1 | 5/2016 | Pimenta et al. |
| 9,351,848 | B2 | 5/2016 | Glerum et al. |
| 9,357,909 | B2 | 6/2016 | Perez-Cruet et al. |
| 9,358,126 | B2 | 6/2016 | Glerum et al. |
| 9,358,127 | B2 | 6/2016 | Duffield et al. |
| 9,358,128 | B2 | 6/2016 | Glerum et al. |
| 9,358,129 | B2 | 6/2016 | Weiman |
| 9,364,341 | B2 | 6/2016 | Gowan |
| 9,364,343 | B2 | 6/2016 | Duffield et al. |
| 9,370,434 | B2 | 6/2016 | Weiman |
| 9,370,435 | B2 | 6/2016 | Walkenhorst et al. |
| 9,381,008 | B2 | 7/2016 | Thornburg |
| 9,386,916 | B2 | 7/2016 | Predick et al. |
| 9,387,092 | B2 | 7/2016 | Mermuys et al. |
| 9,402,673 | B2 | 8/2016 | Cormier et al. |
| 9,402,739 | B2 | 8/2016 | Weiman et al. |
| 9,408,596 | B2 | 8/2016 | Blain |
| 9,408,708 | B2 | 8/2016 | Greenhalgh |
| 9,414,828 | B2 | 8/2016 | Abidin et al. |
| 9,414,934 | B2 | 8/2016 | Cain |
| 9,414,937 | B2 | 8/2016 | Carlson et al. |
| 9,421,110 | B2 | 8/2016 | Masson et al. |

(56) References Cited

U.S. PATENT DOCUMENTS 9,427,331 B2 8/2016 Arnin
9,445,919 B2 9/2016 Palmatier et al.
9,452,063 B2 9/2016 Glerum et al.
9,456,903 B2 10/2016 Glerum et al.
9,456,906 B2 10/2016 Gray et al.
9,468,405 B2 10/2016 Miles et al.
9,474,622 B2 10/2016 McLaughlin et al.
9,474,625 B2 10/2016 Weiman
9,480,573 B2 11/2016 Perloff et al.
9,480,576 B2 11/2016 Pepper et al.
9,480,579 B2 11/2016 Davenport et al.
9,486,133 B2 11/2016 Lee et al.
9,486,325 B2 11/2016 Davenport et al.
9,486,327 B2 11/2016 Martynova et al.
9,486,328 B2 11/2016 Jimenez et al.
9,492,287 B2 11/2016 Glerum et al.
9,492,288 B2 11/2016 Wagner et al.
9,492,289 B2 11/2016 Davenport et al.
9,498,349 B2 11/2016 Patterson et al.
9,510,954 B2 12/2016 Glerum et al.
9,517,098 B2 12/2016 Anderson
9,522,070 B2 12/2016 Flower et al.
9,526,620 B2 12/2016 Slivka et al.
9,526,625 B2 12/2016 Cain
9,532,821 B2 1/2017 Moskowitz et al.
9,539,103 B2 1/2017 McLaughlin et al.
9,539,108 B2 1/2017 Glerum et al.
9,545,320 B2 1/2017 Padovani et al.
9,549,723 B2 1/2017 Hynes et al.
9,549,824 B2 1/2017 McAfee
9,561,116 B2 2/2017 Weiman et al.
9,566,163 B2 2/2017 Suddaby et al.
9,566,166 B2 2/2017 Parry et al.
9,566,168 B2 2/2017 Glerum et al.
9,572,560 B2 2/2017 Mast et al.
9,572,677 B2 2/2017 Davenport et al.
9,572,681 B2 2/2017 Mathieu et al.
9,579,124 B2 2/2017 Gordon et al.
9,579,139 B2 2/2017 Cormier et al.
9,579,213 B2 2/2017 Bal et al.
9,585,649 B2 3/2017 Blain et al.
9,585,762 B2 3/2017 Suddaby et al.
9,585,766 B2 3/2017 Robinson
9,585,767 B2 3/2017 Robinson
9,592,129 B2 3/2017 Slivka et al.
9,597,195 B2 3/2017 Cain
9,603,643 B2 3/2017 Reed et al.
9,603,713 B2 3/2017 Moskowitz et al.
9,603,717 B2 3/2017 Ibarra et al.
9,615,818 B2 4/2017 Baudouin et al.
9,615,936 B2 4/2017 Duffield et al.
9,622,732 B2 4/2017 Martinelli et al.
9,622,875 B2 4/2017 Moskowitz et al.
9,622,876 B1 4/2017 Greenhalgh et al.
9,629,729 B2 4/2017 Grimberg, Jr. et al.
9,636,097 B2 5/2017 Bass
9,642,720 B2 5/2017 Radcliffe et al.
9,649,198 B2 5/2017 Wolters et al.
9,655,746 B2 5/2017 Seifert
9,655,747 B2 5/2017 Glerum et al.
9,662,224 B2 5/2017 Weiman et al.
9,668,784 B2 6/2017 Brumfield et al.
9,668,876 B2 6/2017 Blain et al.
9,668,879 B2 6/2017 Jimenez et al.
9,675,465 B2 6/2017 Padovani et al.
9,675,467 B2 6/2017 Duffield et al.
9,675,468 B1 6/2017 Jensen
9,693,871 B2 7/2017 Richerme et al.
9,700,428 B2 7/2017 Niemiec et al.
9,707,092 B2 7/2017 Davenport et al.
9,713,536 B2 7/2017 Foley et al.
9,717,601 B2 8/2017 Miller
9,730,684 B2 8/2017 Beale et al.
9,730,806 B2 8/2017 Capote
9,737,288 B2 8/2017 Karpowicz et al.
9,750,617 B2 9/2017 Lim et al.
9,750,618 B1 9/2017 Daffinson et al.
9,757,249 B2 9/2017 Radcliffe et al.
9,763,722 B2 9/2017 Roybal
9,770,343 B2 9/2017 Weiman
9,782,265 B2 10/2017 Weiman et al.
9,788,971 B1 10/2017 Stein
9,795,370 B2 10/2017 O'Connell et al.
9,795,371 B2 10/2017 Miles et al.
9,801,733 B2 10/2017 Wolters et al.
9,801,734 B1 10/2017 Stein et al.
9,808,352 B2 11/2017 Suddaby et al.
9,826,966 B2 11/2017 Mast et al.
9,827,024 B2 11/2017 Cormier et al.
9,827,107 B1 11/2017 Arnin
9,833,333 B2 12/2017 Duffield et al.
9,833,336 B2 12/2017 Davenport et al.
9,839,527 B2 12/2017 Robinson
9,839,528 B2 12/2017 Weiman et al.
9,848,993 B2 12/2017 Moskowitz et al.
9,848,996 B2 12/2017 Faulhaber
9,855,151 B2 1/2018 Weiman
9,867,715 B2 1/2018 McLaughlin et al.
9,872,779 B2 1/2018 Miller et al.
9,889,019 B2 2/2018 Rogers et al.
9,907,671 B2 3/2018 Fessler
9,907,673 B2 3/2018 Weiman et al.
9,918,709 B2 3/2018 Sandhu
9,924,859 B2 3/2018 Lee et al.
9,924,940 B2 3/2018 Moskowitz et al.
9,925,062 B2 3/2018 Glerum et al.
9,925,064 B2 3/2018 Duffield et al.
9,931,223 B2 4/2018 Cain
9,937,053 B2 4/2018 Melkent et al.
9,937,060 B2 4/2018 Fuhrer et al.
9,943,342 B2 4/2018 Tanaka et al.
9,943,418 B2 4/2018 Davenport et al.
9,949,775 B2 4/2018 Reed et al.
9,949,841 B2 4/2018 Glerum et al.
9,956,087 B2 5/2018 Seifert et al.
9,962,202 B2 5/2018 Anderson
9,962,270 B2 5/2018 Alheidt et al.
9,962,271 B2 5/2018 Glerum
9,962,272 B1 5/2018 Daffinson et al.
9,968,461 B2 5/2018 Zappacosta et al.
9,968,462 B2 5/2018 Weiman
9,974,531 B2 5/2018 Miles et al.
9,974,662 B2 5/2018 Hessler et al.
9,974,664 B2 5/2018 Emerick et al.
9,980,825 B2 5/2018 Nichols et al.
9,980,826 B2 5/2018 Martynova et al.
9,987,141 B2 6/2018 Duffield et al.
9,987,143 B2 6/2018 Robinson et al.
9,987,144 B2 6/2018 Seifert et al.
9,987,146 B1 6/2018 Lentner et al.
9,993,239 B2 6/2018 Karpowicz et al.
9,993,350 B2 6/2018 Cain
10,004,607 B2 6/2018 Weiman et al.
10,004,608 B2 6/2018 Carnes et al.
10,016,282 B2 7/2018 Seifert et al.
10,016,284 B2 7/2018 Moskowitz et al.
10,022,239 B1 7/2018 Lentner et al.
10,028,842 B2 7/2018 Gray et al.
10,034,765 B2 7/2018 Blain et al.
10,034,769 B2 7/2018 Baynham
10,034,771 B2 7/2018 Capote et al.
10,034,772 B2 7/2018 Glerum et al.
10,034,773 B2 7/2018 McLaughlin et al.
10,039,539 B2 8/2018 Friedrich et al.
10,039,650 B2 8/2018 Lamborne et al.
10,052,214 B2 8/2018 Jimenez et al.
10,058,431 B2 8/2018 Tyber et al.
10,060,469 B2 8/2018 Jimenez et al.
10,070,852 B2 9/2018 Mast et al.
10,076,320 B2 9/2018 Mast et al.
10,076,423 B2 9/2018 Miller et al.
10,080,666 B2 9/2018 Suddaby et al.
10,080,669 B2 9/2018 Davenport et al.
10,085,846 B2 10/2018 Grotz

(56) References Cited

U.S. PATENT DOCUMENTS

| | | | |
|---|---|---|---|
| 10,085,849 | B2 | 10/2018 | Weiman et al. |
| 10,092,417 | B2 | 10/2018 | Weiman et al. |
| 10,098,758 | B2 | 10/2018 | Matthews et al. |
| 10,098,759 | B2 | 10/2018 | Weiman |
| 10,111,755 | B2 | 10/2018 | Foley et al. |
| 10,111,758 | B2 | 10/2018 | Robinson |
| 10,117,754 | B2 | 11/2018 | Davenport et al. |
| 10,117,755 | B2 | 11/2018 | Emerick et al. |
| 10,137,002 | B2 | 11/2018 | Padovani et al. |
| 10,137,006 | B2 | 11/2018 | Dewey et al. |
| 10,137,007 | B2 | 11/2018 | Dewey et al. |
| 10,137,009 | B2 | 11/2018 | Weiman et al. |
| 10,149,671 | B2 | 12/2018 | Predick et al. |
| 10,149,710 | B2 | 12/2018 | Tanaka et al. |
| 10,154,781 | B2 | 12/2018 | Weiman |
| 10,154,912 | B2 | 12/2018 | Glerum |
| 10,154,914 | B2 | 12/2018 | Robinson |
| 10,159,584 | B2 | 12/2018 | Carnes et al. |
| 10,166,117 | B1 | 1/2019 | Daffinson et al. |
| 10,172,515 | B2 | 1/2019 | Lee et al. |
| 10,172,652 | B2 | 1/2019 | Woolley et al. |
| 10,178,987 | B2 | 1/2019 | Predick et al. |
| 10,179,053 | B2 | 1/2019 | Zappacosta et al. |
| 10,182,922 | B2 | 1/2019 | Nichols et al. |
| 10,188,527 | B2 | 1/2019 | Rogers et al. |
| 10,195,050 | B2 | 2/2019 | Palmatier et al. |
| 10,201,431 | B2 | 2/2019 | Slater et al. |
| 10,213,192 | B2 | 2/2019 | Capote |
| 10,213,193 | B2 | 2/2019 | Karpowicz et al. |
| 10,219,798 | B2 | 3/2019 | Capote |
| 10,219,913 | B2 | 3/2019 | Matthews et al. |
| 10,219,914 | B2 | 3/2019 | Faulhaber |
| 10,219,915 | B1 | 3/2019 | Stein |
| 10,226,356 | B2 | 3/2019 | Grotz |
| 10,226,359 | B2 | 3/2019 | Glerum et al. |
| 10,238,375 | B2 | 3/2019 | O'Connell et al. |
| 10,238,383 | B2 | 3/2019 | Moskowitz et al. |
| 10,238,503 | B2 | 3/2019 | Branch et al. |
| 10,245,015 | B2 | 4/2019 | Predick et al. |
| 10,251,643 | B2 | 4/2019 | Moskowitz et al. |
| 10,265,191 | B2 | 4/2019 | Lim et al. |
| 10,278,686 | B2 | 5/2019 | Baudouin et al. |
| 10,278,786 | B2 | 5/2019 | Friedrich et al. |
| 10,278,830 | B1 | 5/2019 | Walker et al. |
| 10,278,831 | B2 | 5/2019 | Sandul |
| 10,278,832 | B2 | 5/2019 | Nichols et al. |
| 10,285,680 | B2 | 5/2019 | Friedrich et al. |
| 10,285,819 | B2 | 5/2019 | Greenhalgh |
| 10,285,824 | B2 | 5/2019 | Robinson |
| 10,292,828 | B2 | 5/2019 | Greenhalgh |
| 10,299,777 | B2 | 5/2019 | Mast et al. |
| 10,299,934 | B2 | 5/2019 | Seifert et al. |
| 10,299,937 | B2 | 5/2019 | McAfee |
| 10,307,268 | B2 | 6/2019 | Moskowitz et al. |
| 10,314,622 | B2 | 6/2019 | Brumfield et al. |
| 10,314,719 | B2 | 6/2019 | Hessler et al. |
| 10,322,007 | B2 | 6/2019 | Masson et al. |
| 10,322,009 | B2 | 6/2019 | Aghayev et al. |
| 10,327,909 | B2 | 6/2019 | Baynham |
| 10,327,912 | B1 | 6/2019 | Suddaby |
| 10,327,917 | B2 | 6/2019 | Glerum et al. |
| 10,342,675 | B2 | 7/2019 | Alheidt |
| 10,350,085 | B2 | 7/2019 | Glerum et al. |
| 10,357,233 | B2 | 7/2019 | Miles et al. |
| 10,363,142 | B2 | 7/2019 | McClintock et al. |
| 10,363,144 | B2 | 7/2019 | Overes et al. |
| 10,369,004 | B2 | 8/2019 | Faulhaber |
| 10,369,008 | B2 | 8/2019 | Jimenez et al. |
| 10,369,010 | B2 | 8/2019 | Robinson et al. |
| 10,369,012 | B2 | 8/2019 | Fessler |
| 10,376,377 | B2 | 8/2019 | Seifert et al. |
| 10,390,962 | B2 | 8/2019 | Weiman |
| 10,390,964 | B2 | 8/2019 | Faulhaber |
| 10,398,563 | B2 | 9/2019 | Engstrom |
| 10,398,566 | B2 | 9/2019 | Olmos et al. |
| 10,413,419 | B2 | 9/2019 | Thibodeau |
| 10,413,422 | B2 | 9/2019 | Flower et al. |
| 10,413,423 | B2 | 9/2019 | Overes et al. |
| 10,426,450 | B2 | 10/2019 | Vogel et al. |
| 10,426,633 | B2 | 10/2019 | Moskowitz et al. |
| 10,426,634 | B1 | 10/2019 | Al-Jazaeri et al. |
| 10,441,430 | B2 | 10/2019 | Ludwig et al. |
| 10,449,056 | B2 | 10/2019 | Cain |
| 10,456,122 | B2 | 10/2019 | Koltz et al. |
| 10,470,894 | B2 | 11/2019 | Foley et al. |
| 10,478,319 | B2 | 11/2019 | Moskowitz et al. |
| 10,492,912 | B2 | 12/2019 | Gregersen et al. |
| 10,492,922 | B2 | 12/2019 | Mathieu et al. |
| 10,492,924 | B2 | 12/2019 | Stein et al. |
| 10,500,064 | B2 | 12/2019 | Robinson |
| 10,512,550 | B2 | 12/2019 | Bechtel et al. |
| 10,517,645 | B2 | 12/2019 | van der Pol |
| 10,524,924 | B2 | 1/2020 | Davenport et al. |
| 10,531,903 | B2 | 1/2020 | Daly et al. |
| 10,537,436 | B2 | 1/2020 | Maguire et al. |
| 10,537,438 | B2 | 1/2020 | Martynova et al. |
| 10,555,729 | B1 | 2/2020 | Cole et al. |
| 10,561,411 | B1 | 2/2020 | Cole et al. |
| 10,575,889 | B2 | 3/2020 | Roybal |
| 10,575,960 | B2 | 3/2020 | Duffield et al. |
| 10,582,959 | B2 | 3/2020 | Langer et al. |
| 10,583,015 | B2 | 3/2020 | Olmos et al. |
| 10,603,078 | B2 | 3/2020 | Simpson et al. |
| 10,610,376 | B2 | 4/2020 | Kuyler et al. |
| 10,624,757 | B2 | 4/2020 | Bost et al. |
| 10,624,758 | B2 | 4/2020 | Slivka et al. |
| 10,624,761 | B2 | 4/2020 | Davenport et al. |
| 10,639,163 | B2 | 5/2020 | Tyber et al. |
| 10,639,166 | B2 | 5/2020 | Weiman et al. |
| 10,653,458 | B2 | 5/2020 | Tanaka et al. |
| 10,667,925 | B2 | 6/2020 | Emerick et al. |
| 10,667,927 | B2 | 6/2020 | Lamborne et al. |
| 10,675,157 | B2 | 6/2020 | Zakelj et al. |
| 10,682,241 | B2 | 6/2020 | Glerum et al. |
| 10,687,963 | B2 | 6/2020 | Jimenez et al. |
| 10,702,393 | B2 | 7/2020 | Davenport et al. |
| 10,709,569 | B2 | 7/2020 | McLaughlin et al. |
| 10,709,571 | B2 | 7/2020 | Iott et al. |
| 10,709,572 | B2 | 7/2020 | Daffinson et al. |
| 10,709,575 | B2 | 7/2020 | Robinson |
| 10,722,377 | B2 | 7/2020 | Glerum et al. |
| 10,722,379 | B2 | 7/2020 | McLaughlin et al. |
| 10,729,561 | B2 | 8/2020 | Glerum |
| 10,743,858 | B1 | 8/2020 | Cole et al. |
| 10,744,002 | B2 | 8/2020 | Glerum et al. |
| 10,758,366 | B2 | 9/2020 | Daffinson et al. |
| 10,758,367 | B2 | 9/2020 | Weiman et al. |
| 10,758,369 | B2 | 9/2020 | Rogers et al. |
| 10,765,528 | B2 | 9/2020 | Weiman et al. |
| 10,772,737 | B2 | 9/2020 | Gray et al. |
| 10,779,955 | B2 | 9/2020 | Kuyler et al. |
| 10,779,957 | B2 | 9/2020 | Weiman et al. |
| 10,786,364 | B2 | 9/2020 | Davenport et al. |
| 10,786,369 | B2 | 9/2020 | Carnes et al. |
| 10,799,368 | B2 | 10/2020 | Glerum et al. |
| 10,835,387 | B2 | 11/2020 | Weiman et al. |
| 10,842,640 | B2 | 11/2020 | Weiman et al. |
| 10,842,644 | B2 | 11/2020 | Weiman et al. |
| 10,856,997 | B2 | 12/2020 | Cowan et al. |
| 10,869,769 | B2 | 12/2020 | Eisen et al. |
| 10,874,447 | B2 | 12/2020 | Tanaka et al. |
| 10,874,522 | B2 | 12/2020 | Weiman |
| 10,874,523 | B2 | 12/2020 | Weiman et al. |
| 10,874,524 | B2 | 12/2020 | Bjork |
| 10,881,524 | B2 | 1/2021 | Eisen et al. |
| 10,881,531 | B2 | 1/2021 | Berry |
| 10,888,431 | B1 | 1/2021 | Robinson |
| 10,898,344 | B2 | 1/2021 | Alheidt et al. |
| 10,898,346 | B1 | 1/2021 | Suddaby |
| 10,925,656 | B2 | 2/2021 | Cole et al. |
| 10,925,750 | B2 | 2/2021 | Zappacosta et al. |
| 10,925,752 | B2 | 2/2021 | Weiman |
| 10,932,920 | B2 | 3/2021 | Dewey et al. |
| 10,940,014 | B2 | 3/2021 | Greenhalgh |

(56) References Cited

U.S. PATENT DOCUMENTS

| | | | |
|---|---|---|---|
| 10,945,858 | B2 | 3/2021 | Bechtel et al. |
| 10,952,866 | B2 | 3/2021 | Warren et al. |
| 10,959,855 | B2 | 3/2021 | Miller et al. |
| 10,959,856 | B2 | 3/2021 | Seifert et al. |
| 10,973,649 | B2 | 4/2021 | Weiman et al. |
| 10,973,650 | B2 | 4/2021 | Stein |
| 10,980,642 | B2 | 4/2021 | Glerum et al. |
| 10,980,644 | B2 | 4/2021 | Purcell et al. |
| 10,993,814 | B2 | 5/2021 | Wolters |
| 11,007,067 | B2 | 5/2021 | Masson et al. |
| 11,013,617 | B2 | 5/2021 | Weiman et al. |
| 11,020,238 | B2 | 6/2021 | Nichols et al. |
| 11,020,239 | B2 | 6/2021 | Miller et al. |
| 11,026,804 | B2 | 6/2021 | Jimenez et al. |
| 11,026,812 | B2 | 6/2021 | Daffinson et al. |
| 11,033,401 | B2 | 6/2021 | Shoshtaev |
| 11,033,402 | B2 | 6/2021 | Melkent et al. |
| 11,033,404 | B2 | 6/2021 | Faulhaber |
| 11,039,935 | B2 | 6/2021 | McAfee |
| 11,045,326 | B2 | 6/2021 | Seifert et al. |
| 11,045,327 | B2 | 6/2021 | Nichols et al. |
| 11,051,949 | B2 | 7/2021 | Walker et al. |
| 11,051,951 | B2 | 7/2021 | Robinson et al. |
| 11,058,469 | B2 | 7/2021 | Mahajan et al. |
| 11,065,127 | B1 | 7/2021 | Lentner et al. |
| 11,065,129 | B2 | 7/2021 | Sandul |
| 11,065,130 | B2 | 7/2021 | Branch et al. |
| 11,076,966 | B2 | 8/2021 | Faulhaber |
| 11,083,584 | B2 | 8/2021 | Lauf et al. |
| 11,083,595 | B2 | 8/2021 | Robinson |
| 11,090,167 | B2 | 8/2021 | Emerick et al. |
| 11,096,795 | B2 | 8/2021 | Padovani et al. |
| 11,096,797 | B2 | 8/2021 | Moskowitz et al. |
| 11,103,366 | B2 | 8/2021 | Glerum et al. |
| RE48,719 | E | 9/2021 | Suddaby et al. |
| 11,109,980 | B2 | 9/2021 | Seifert et al. |
| 11,116,644 | B2 | 9/2021 | Marrocco et al. |
| 11,123,198 | B2 | 9/2021 | Black et al. |
| 11,123,200 | B2 | 9/2021 | Faulhaber |
| 11,129,731 | B2 | 9/2021 | Miller et al. |
| 11,135,071 | B2 | 10/2021 | Dewey et al. |
| 11,147,680 | B2 | 10/2021 | Tyber et al. |
| 11,154,404 | B2 * | 10/2021 | Freedman .......... A61B 17/7059 |
| 11,160,666 | B2 | 11/2021 | Burkhardt et al. |
| 11,160,669 | B2 | 11/2021 | Rogers et al. |
| 11,166,826 | B2 | 11/2021 | Huang |
| 11,173,044 | B1 | 11/2021 | Jones et al. |
| 11,179,234 | B2 | 11/2021 | Dacosta et al. |
| 11,285,014 | B1 | 3/2022 | Josse et al. |
| 11,376,134 | B1 | 7/2022 | Dewey et al. |
| 11,395,743 | B1 | 7/2022 | Hynes et al. |
| 11,602,440 | B2 * | 3/2023 | Zakelj .................. A61F 2/4611 |
| 11,612,499 | B2 * | 3/2023 | Barfield ................ A61F 2/4455 623/17.16 |
| 11,617,658 | B2 | 4/2023 | Josse et al. |
| 11,723,780 | B2 | 8/2023 | Seifert et al. |
| 11,737,892 | B1 | 8/2023 | Kadaba et al. |
| 11,806,250 | B2 * | 11/2023 | Miller .................. A61F 2/4455 |
| 12,064,354 | B2 | 8/2024 | Robinson et al. |
| 2002/0045943 | A1 | 4/2002 | Uk |
| 2002/0045945 | A1 | 4/2002 | Liu et al. |
| 2002/0055741 | A1 | 5/2002 | Schlapfer et al. |
| 2002/0116066 | A1 | 8/2002 | Chauvin et al. |
| 2002/0128713 | A1 | 9/2002 | Ferree |
| 2002/0151976 | A1 | 10/2002 | Foley et al. |
| 2002/0183762 | A1 | 12/2002 | Anderson et al. |
| 2003/0050701 | A1 | 3/2003 | Michelson |
| 2003/0130739 | A1 | 7/2003 | Gerbec et al. |
| 2003/0163132 | A1 | 8/2003 | Chin |
| 2004/0102778 | A1 | 5/2004 | Huebner et al. |
| 2004/0172134 | A1 | 9/2004 | Berry |
| 2004/0186570 | A1 | 9/2004 | Rapp |
| 2004/0193158 | A1 | 9/2004 | Lim et al. |
| 2004/0204713 | A1 | 10/2004 | Abdou |
| 2004/0249461 | A1 | 12/2004 | Ferree |
| 2004/0254643 | A1 | 12/2004 | Jackson |
| 2004/0254644 | A1 | 12/2004 | Taylor |
| 2005/0015094 | A1 | 1/2005 | Keller |
| 2005/0015149 | A1 | 1/2005 | Michelson |
| 2005/0033429 | A1 | 2/2005 | Kuo |
| 2005/0033439 | A1 | 2/2005 | Gordon et al. |
| 2005/0147478 | A1 | 7/2005 | Greenberg |
| 2005/0154459 | A1 | 7/2005 | Wolek et al. |
| 2005/0209698 | A1 | 9/2005 | Gordon et al. |
| 2005/0228398 | A1 | 10/2005 | Rathbun et al. |
| 2006/0122701 | A1 | 6/2006 | Kiester |
| 2006/0129244 | A1 | 6/2006 | Ensign |
| 2006/0260446 | A1 | 11/2006 | Chang |
| 2006/0276901 | A1 | 12/2006 | Zipnick et al. |
| 2007/0173840 | A1 | 7/2007 | Huebner |
| 2007/0218750 | A1 | 9/2007 | Corrao et al. |
| 2007/0233150 | A1 | 10/2007 | Blain et al. |
| 2007/0270859 | A1 | 11/2007 | Companioni et al. |
| 2008/0058804 | A1 | 3/2008 | Lechot et al. |
| 2008/0132959 | A1 | 6/2008 | Mikkonen et al. |
| 2008/0140207 | A1 | 6/2008 | Olmos et al. |
| 2008/0287957 | A1 | 11/2008 | Hester et al. |
| 2009/0024158 | A1 | 1/2009 | Viker |
| 2009/0036746 | A1 | 2/2009 | Blackwell et al. |
| 2009/0093830 | A1 | 4/2009 | Miller |
| 2009/0105834 | A1 | 4/2009 | Hovda et al. |
| 2009/0292361 | A1 | 11/2009 | Lopez |
| 2010/0049324 | A1 | 2/2010 | Valdevit et al. |
| 2010/0070035 | A1 | 3/2010 | Mayer |
| 2010/0076440 | A1 | 3/2010 | Pamichev et al. |
| 2010/0082109 | A1 | 4/2010 | Greenhalgh et al. |
| 2010/0114183 | A1 | 5/2010 | Wassinger et al. |
| 2010/0152853 | A1 | 6/2010 | Kirschman |
| 2010/0191336 | A1 | 7/2010 | Greenhalgh |
| 2010/0211176 | A1 | 8/2010 | Greenhalgh |
| 2010/0280617 | A1 | 11/2010 | Coppes et al. |
| 2010/0286777 | A1 | 11/2010 | Errico et al. |
| 2011/0118843 | A1 | 5/2011 | Mathieu et al. |
| 2011/0130838 | A1 | 6/2011 | Morgenstern Lopez |
| 2011/0144755 | A1 | 6/2011 | Baynham et al. |
| 2011/0153020 | A1 | 6/2011 | Abdelgany et al. |
| 2011/0218572 | A1 | 9/2011 | Lechmann et al. |
| 2011/0218631 | A1 | 9/2011 | Woodburn, Sr. et al. |
| 2011/0237898 | A1 | 9/2011 | Stone et al. |
| 2011/0301577 | A1 | 12/2011 | Simmen et al. |
| 2012/0004732 | A1 | 1/2012 | Goel et al. |
| 2012/0010717 | A1 | 1/2012 | Spann |
| 2012/0022575 | A1 | 1/2012 | Mire et al. |
| 2012/0095515 | A1 | 4/2012 | Hamilton |
| 2012/0101581 | A1 | 4/2012 | Mathieu et al. |
| 2012/0109142 | A1 | 5/2012 | Dayan |
| 2012/0109309 | A1 | 5/2012 | Mathieu et al. |
| 2012/0109310 | A1 | 5/2012 | Mathieu et al. |
| 2012/0109312 | A1 | 5/2012 | Mathieu et al. |
| 2012/0109313 | A1 | 5/2012 | Mathieu et al. |
| 2012/0123546 | A1 | 5/2012 | Medina |
| 2012/0143195 | A1 | 6/2012 | Sander |
| 2012/0150237 | A1 | 6/2012 | Combrowski |
| 2012/0197401 | A1 | 8/2012 | Duncan et al. |
| 2012/0209385 | A1 | 8/2012 | Aferzon |
| 2012/0215313 | A1 | 8/2012 | Saidha et al. |
| 2012/0215316 | A1 | 8/2012 | Mohr et al. |
| 2012/0232349 | A1 | 9/2012 | Perrow |
| 2013/0103095 | A1 | 4/2013 | Brumfield et al. |
| 2013/0158664 | A1 | 6/2013 | Palmatier et al. |
| 2013/0184823 | A1 | 7/2013 | Malberg |
| 2013/0190876 | A1 | 7/2013 | Drochner et al. |
| 2013/0211526 | A1 | 8/2013 | Alheidt et al. |
| 2013/0226191 | A1 | 8/2013 | Thoren et al. |
| 2013/0231747 | A1 | 9/2013 | Olmos et al. |
| 2013/0274557 | A1 | 10/2013 | Bowman et al. |
| 2013/0304136 | A1 | 11/2013 | Gourlaouen-Preissler et al. |
| 2013/0317312 | A1 | 11/2013 | Eastlack et al. |
| 2014/0018816 | A1 | 1/2014 | Fenn et al. |
| 2014/0039622 | A1 | 2/2014 | Glerum et al. |
| 2014/0107790 | A1 | 4/2014 | Combrowski |
| 2014/0114321 | A1 | 4/2014 | Davenport et al. |
| 2014/0114420 | A1 | 4/2014 | Robinson |
| 2014/0148904 | A1 | 5/2014 | Robinson |

(56) References Cited

U.S. PATENT DOCUMENTS

2014/0163682 A1 6/2014 Iott et al.
2014/0180419 A1 6/2014 Dmuschewsky
2014/0194992 A1 7/2014 Medina
2014/0249629 A1 9/2014 Moskowitz et al.
2014/0249631 A1 9/2014 Weiman
2014/0277471 A1 9/2014 Gray et al.
2014/0277473 A1 9/2014 Perrow
2014/0277487 A1 9/2014 Davenport et al.
2014/0277500 A1 9/2014 Logan et al.
2014/0303674 A1 10/2014 Sasing
2014/0364855 A1 12/2014 Stoll et al.
2014/0379085 A1 12/2014 Duffield et al.
2015/0173915 A1 6/2015 Laubert et al.
2015/0223945 A1 8/2015 Weiman et al.
2015/0230931 A1 8/2015 Greenhalgh
2015/0238236 A1 8/2015 Sasing
2015/0354635 A1 12/2015 McClymont et al.
2015/0374507 A1 12/2015 Wolters et al.
2016/0008924 A1 1/2016 Canourgues et al.
2016/0022434 A1 1/2016 Robinson
2016/0051373 A1 2/2016 Faulhaber
2016/0058571 A1 3/2016 McLaughlin et al.
2016/0081681 A1 3/2016 Waugh et al.
2016/0089247 A1 3/2016 Nichols et al.
2016/0095710 A1 4/2016 Juszczyk et al.
2016/0095718 A1 4/2016 Burkhardt et al.
2016/0100951 A1 4/2016 Suddaby et al.
2016/0128847 A1 5/2016 Kurtaliaj et al.
2016/0199073 A1 7/2016 Nino et al.
2016/0242930 A1 8/2016 Duffield et al.
2016/0256291 A1 9/2016 Miller
2016/0278830 A1 9/2016 Arrington
2016/0296340 A1 10/2016 Gordon et al.
2016/0310291 A1 10/2016 Greenhalgh
2016/0345952 A1 12/2016 Kucharzyk et al.
2016/0367377 A1 12/2016 Faulhaber
2017/0010025 A1 1/2017 Mayershofer
2017/0029635 A1 2/2017 Doll et al.
2017/0035406 A1 2/2017 Abidin et al.
2017/0049651 A1 2/2017 Lim et al.
2017/0049653 A1 2/2017 Lim et al.
2017/0095345 A1 4/2017 Davenport et al.
2017/0100255 A1 4/2017 Hleihil et al.
2017/0100257 A1 4/2017 Weiman et al.
2017/0105844 A1 4/2017 Kuyler et al.
2017/0112630 A1 4/2017 Kuyler et al.
2017/0151065 A1 6/2017 Warren et al.
2017/0156882 A1 6/2017 Rathbun et al.
2017/0156884 A1 6/2017 Rathbun et al.
2017/0189200 A1 7/2017 Miller et al.
2017/0189204 A1 7/2017 Riemhofer et al.
2017/0202678 A1 7/2017 Duffield et al.
2017/0215856 A1 8/2017 Martinelli et al.
2017/0224502 A1 8/2017 Wolters et al.
2017/0224504 A1 8/2017 Butler et al.
2017/0231675 A1 8/2017 Combrowski
2017/0231780 A1 8/2017 D'Urso
2017/0246006 A1 8/2017 Carnes et al.
2017/0290677 A1 10/2017 Olmos et al.
2017/0296352 A1 10/2017 Richerme et al.
2017/0333200 A1 11/2017 Arnin
2017/0367842 A1 12/2017 Predick et al.
2017/0367843 A1 12/2017 Eisen et al.
2017/0367844 A1 12/2017 Eisen et al.
2017/0367845 A1 12/2017 Eisen et al.
2018/0000606 A1 1/2018 Hessler et al.
2018/0030362 A1 2/2018 Kosler et al.
2018/0031810 A1 2/2018 Hsu et al.
2018/0036136 A1 2/2018 Duffield et al.
2018/0036138 A1 2/2018 Robinson
2018/0104066 A1 4/2018 Bae et al.
2018/0116819 A1 5/2018 Maguire et al.
2018/0116891 A1 5/2018 Beale et al.
2018/0193160 A1 7/2018 Hsu et al.
2018/0193164 A1 7/2018 Shoshtaev
2018/0206999 A1 7/2018 Suddaby
2018/0256356 A1 9/2018 Robinson et al.
2018/0256359 A1 9/2018 Greenhalgh
2018/0256360 A1 9/2018 Cain
2018/0256362 A1 9/2018 Slivka et al.
2018/0263784 A1 9/2018 Bechtel et al.
2018/0271513 A1 9/2018 Perrow et al.
2018/0280142 A1 10/2018 Schultz et al.
2018/0303473 A1 10/2018 Spann et al.
2018/0303621 A1 10/2018 Brotman et al.
2018/0303625 A1 10/2018 Alheidt et al.
2018/0311048 A1 11/2018 Glerum et al.
2018/0318101 A1 11/2018 Engstrom
2018/0318102 A1 11/2018 Seifert et al.
2018/0325574 A1 11/2018 Bjork et al.
2018/0338838 A1 11/2018 Cryder et al.
2018/0338841 A1 11/2018 Miller et al.
2018/0344307 A1 12/2018 Hynes et al.
2018/0360616 A1 12/2018 Luu
2019/0000640 A1 1/2019 Weiman
2019/0000702 A1 1/2019 Lim et al.
2019/0000707 A1 1/2019 Lim et al.
2019/0020121 A1 1/2019 Paulotto et al.
2019/0021716 A1 1/2019 Waugh et al.
2019/0021873 A1 1/2019 Dmuschewsky
2019/0046329 A1 2/2019 Padovani et al.
2019/0046381 A1 2/2019 Lim et al.
2019/0046383 A1 2/2019 Lim et al.
2019/0060083 A1 2/2019 Weiman et al.
2019/0082949 A1 3/2019 Weiman
2019/0083081 A1 3/2019 Ortiz et al.
2019/0091033 A1 3/2019 Dewey et al.
2019/0105175 A1 4/2019 Zappacosta et al.
2019/0125328 A1 5/2019 Blain
2019/0133434 A1 5/2019 Lee et al.
2019/0133645 A1 5/2019 Gordon et al.
2019/0133779 A1 5/2019 McLaughlin et al.
2019/0133780 A1 5/2019 Matthews et al.
2019/0133784 A1 5/2019 Gunn et al.
2019/0133788 A1 5/2019 Weiman et al.
2019/0142480 A1 5/2019 Woolley et al.
2019/0151115 A1 5/2019 Nichols et al.
2019/0183656 A1 6/2019 Stein
2019/0201209 A1 7/2019 Branch et al.
2019/0201210 A1 7/2019 Besaw et al.
2019/0209155 A1 7/2019 Mast et al.
2019/0216453 A1 7/2019 Predick et al.
2019/0231551 A1* 8/2019 Freedman .......... A61B 17/8009
2019/0231552 A1 8/2019 Sandul
2019/0240039 A1 8/2019 Walker et al.
2019/0240043 A1 8/2019 Greenhalgh
2019/0247098 A1 8/2019 Brumfield et al.
2019/0254650 A1 8/2019 Martinelli et al.
2019/0254838 A1 8/2019 Miller et al.
2019/0254839 A1 8/2019 Nichols et al.
2019/0262009 A1 8/2019 Cheng
2019/0262139 A1 8/2019 Wolters
2019/0269521 A1 9/2019 Shoshtaev
2019/0274670 A1 9/2019 O'Connell et al.
2019/0274671 A1 9/2019 Lauf et al.
2019/0274836 A1 9/2019 Eisen et al.
2019/0282373 A1 9/2019 Alheidt
2019/0290446 A1 9/2019 Masson et al.
2019/0290447 A1 9/2019 Stein
2019/0298416 A1 10/2019 Rezach
2019/0298524 A1 10/2019 Lauf et al.
2019/0298540 A1 10/2019 Aghayev et al.
2019/0321022 A1 10/2019 Karpowicz et al.
2019/0321190 A1 10/2019 Wagner et al.
2019/0328539 A1 10/2019 Suh et al.
2019/0328540 A1 10/2019 Seifert et al.
2019/0329388 A1 10/2019 Erickson et al.
2019/0336301 A1 11/2019 Engstrom
2019/0336304 A1 11/2019 Burkhardt et al.
2019/0350573 A1 11/2019 Vogel et al.
2019/0358049 A1 11/2019 Faulhaber
2019/0358050 A1 11/2019 Fessler
2019/0358051 A1 11/2019 Flower et al.
2019/0380840 A1 12/2019 Tyber et al.

(56) References Cited

U.S. PATENT DOCUMENTS

2019/0388232 A1 12/2019 Purcell et al.
2020/0008951 A1 1/2020 McClintock et al.
2020/0030114 A1 1/2020 Cain
2020/0030116 A1 1/2020 Jimenez et al.
2020/0038200 A1 2/2020 Foley et al.
2020/0054461 A1 2/2020 Marrocco et al.
2020/0060844 A1 2/2020 Mathieu et al.
2020/0069316 A1 3/2020 DeSoutter et al.
2020/0078190 A1 3/2020 Rogers et al.
2020/0093526 A1 3/2020 Daly et al.
2020/0093607 A1 3/2020 Davenport et al.
2020/0093609 A1 3/2020 Shoshtaev
2020/0100904 A1 4/2020 Stein et al.
2020/0107824 A1 4/2020 Fleischer
2020/0129306 A1 4/2020 Miller et al.
2020/0129307 A1 4/2020 Hunziker et al.
2020/0138591 A1 5/2020 Moskowitz et al.
2020/0138593 A1 5/2020 Martynova et al.
2020/0146840 A1 5/2020 Black et al.
2020/0179120 A1 6/2020 Bielenstein et al.
2020/0205993 A1 7/2020 Davenport et al.
2020/0214754 A1 7/2020 Bowen et al.
2020/0222202 A1 7/2020 Kuyler et al.
2020/0229944 A1 7/2020 Suh et al.
2020/0246159 A1 8/2020 Suh et al.
2020/0246162 A1 8/2020 Schultz et al.
2020/0261242 A1 8/2020 Bost et al.
2020/0268524 A1 8/2020 Glerum et al.
2020/0276028 A1 9/2020 Blain et al.
2020/0281741 A1 9/2020 Grotz
2020/0289287 A1 9/2020 Emerick et al.
2020/0297507 A1 9/2020 Iott et al.
2020/0330239 A1 10/2020 Davenport et al.
2020/0330245 A1 10/2020 Glerum
2020/0345511 A1 11/2020 Daffinson et al.
2020/0352731 A1 11/2020 Berry
2020/0352738 A1 11/2020 Berry
2020/0360153 A1 11/2020 Weiman et al.
2020/0375753 A1 12/2020 McLaughlin et al.
2020/0375755 A1 12/2020 Cain
2020/0383797 A1 12/2020 Predick et al.
2020/0383799 A1 12/2020 Cain
2020/0390433 A1 12/2020 Yu et al.
2020/0390565 A1 12/2020 Jimenez et al.
2020/0397593 A1 12/2020 Davenport et al.
2020/0405497 A1 12/2020 Olmos et al.
2020/0405498 A1 12/2020 Gray et al.
2020/0405499 A1 12/2020 Gerbec et al.
2020/0405500 A1 12/2020 Cain
2021/0007860 A1 1/2021 Glerum et al.
2021/0015626 A1 1/2021 Suddaby
2021/0030555 A1 2/2021 Weiman et al.
2021/0030561 A1 2/2021 Gleason
2021/0045891 A1 2/2021 Rogers et al.
2021/0045892 A1 2/2021 Rogers et al.
2021/0052395 A1 2/2021 Iott et al.
2021/0068959 A1 3/2021 McLuen et al.
2021/0068973 A1* 3/2021 McLuen ............... A61F 2/4455
2021/0068974 A1 3/2021 Cowan et al.
2021/0068982 A1 3/2021 Carnes et al.
2021/0077271 A1 3/2021 Sharabani
2021/0077272 A1 3/2021 Eisen et al.
2021/0085479 A1 3/2021 Weiman et al.
2021/0093462 A1 4/2021 Lucasiewicz et al.
2021/0106434 A1 4/2021 Alheidt et al.
2021/0113349 A1 4/2021 Weiman et al.
2021/0121299 A1 4/2021 Hyder
2021/0121300 A1 4/2021 Weiman et al.
2021/0137697 A1 5/2021 Weiman
2021/0137699 A1 5/2021 Jang et al.
2021/0137701 A1 5/2021 Miller et al.
2021/0154811 A1 5/2021 Spreiter et al.
2021/0161678 A1 6/2021 Dewey et al.
2021/0177618 A1 6/2021 Branch et al.
2021/0186706 A1 6/2021 Spitler et al.
2021/0186709 A1 6/2021 Weiman et al.
2021/0196470 A1 7/2021 Shoshtaev
2021/0205092 A1 7/2021 Glerum et al.
2021/0205094 A1 7/2021 Weiman et al.
2021/0220145 A1 7/2021 Stein
2021/0220147 A1 7/2021 Berry
2021/0236298 A1 8/2021 Weiman et al.
2021/0251770 A1 8/2021 Purcell et al.
2021/0251776 A1 8/2021 Daffinson et al.
2021/0259848 A1 8/2021 Kang et al.
2021/0259849 A1 8/2021 Robinson et al.
2021/0259850 A1 8/2021 Eisen et al.
2021/0267767 A1 9/2021 Stein
2021/0275317 A1 9/2021 Spetzger
2021/0275318 A1 9/2021 Reimels
2021/0275319 A1 9/2021 Reimels
2021/0275321 A1 9/2021 Seifert et al.
2021/0282938 A1 9/2021 Nichols et al.
2021/0298915 A1 9/2021 Faulhaber
2021/0298916 A1 9/2021 Melkent et al.
2021/0307920 A1 10/2021 Walker et al.
2021/0315705 A1 10/2021 Altarac et al.
2021/0322179 A1 10/2021 Miller et al.
2021/0322181 A1 10/2021 Predick
2021/0322182 A1 10/2021 Faulhaber
2021/0330472 A1 10/2021 Shoshtaev
2021/0346174 A1 11/2021 Flint et al.
2021/0353277 A1 11/2021 Gregersen et al.
2021/0401586 A1 12/2021 Zakelj
2022/0015924 A1 1/2022 Freedman et al.
2022/0047312 A1 2/2022 Seykora et al.
2022/0087819 A1 3/2022 Robinson et al.
2022/0133336 A1 5/2022 Tsai et al.
2022/0133497 A1 5/2022 Dewey et al.
2022/0133498 A1 5/2022 Josse et al.
2022/0133499 A1 5/2022 Josse et al.
2022/0218325 A1 7/2022 Josse
2022/0265256 A1 8/2022 Villamil et al.
2022/0296384 A1* 9/2022 Ludwig ................... A61F 2/442
2022/0313450 A1 10/2022 Donohoe et al.
2022/0387184 A1 12/2022 Josse et al.
2022/0409397 A1 12/2022 Hayes et al.
2022/0409398 A1* 12/2022 Hayes ................... A61F 2/4455
2023/0015512 A1 1/2023 Eisen et al.
2023/0018019 A1* 1/2023 Protopsaltis .......... A61F 2/4455
2023/0027836 A1 1/2023 Predick et al.
2023/0137358 A1 5/2023 Hayes et al.
2024/0341968 A1* 10/2024 Scheinfield ........... A61F 2/4202
2024/0382318 A1 11/2024 Dewey
2025/0375302 A1* 12/2025 Scheinfield ........... A61F 2/4225

FOREIGN PATENT DOCUMENTS

DE 44 16 605 C1 6/1995
EP 0 767 636 A1 4/1997
EP 0 880 950 A1 12/1998
EP 0 857 042 B1 11/2001
EP 1 442 732 A1 8/2004
EP 1 124 512 B1 9/2004
EP 1 107 711 B1 10/2004
EP 1 506 753 A1 2/2005
EP 1 459 711 B1 7/2007
EP 2954860 A2 12/2015
EP 3031424 A1 6/2016
EP 3 069 694 A1 9/2016
EP 3213720 A1 9/2017
EP 4000564 A1 5/2022
FR 2781998 A1 2/2000
FR 3082115 A1 12/2019
GB 2 377 387 A 1/2003
KR 102117224 B1 6/2020
KR 102192022 B1 12/2020
KR 20210064236 A 6/2021
KR 102850891 B1 8/2025
WO 92/14423 A1 9/1992
WO 97/ 00054 A1 1/1997
WO 99/ 26562 A1 6/1999
WO 99/66867 A1 12/1999
WO 00/12033 A1 3/2000

(56) References Cited

FOREIGN PATENT DOCUMENTS

| | | | | |
|---|---|---|---|---|
| WO | 00/25706 | A1 | 5/2000 | |
| WO | 00/ 49977 | A1 | 8/2000 | |
| WO | 02/19952 | A1 | 3/2002 | |
| WO | 03/105673 | A2 | 12/2003 | |
| WO | 2006116850 | A1 | 11/2006 | |
| WO | 2012139022 | A2 | 10/2012 | |
| WO | 2014/133755 | A1 | 9/2014 | |
| WO | 2015063721 | A1 | 5/2015 | |
| WO | 2015198335 | A1 | 12/2015 | |
| WO | 2016057940 | A1 | 4/2016 | |
| WO | 2016/205607 | A1 | 12/2016 | |
| WO | 2017/168208 | A1 | 10/2017 | |
| WO | 2018049227 | A1 | 3/2018 | |
| WO | 2021055323 | A1 | 3/2021 | |
| WO | WO-2024241245 | A1 * | 11/2024 | ............ A61F 2/4611 |
| WO | 2025179249 | A1 | 8/2025 | |

OTHER PUBLICATIONS

Search Report and Written Opinion for Application No. PCT/US2019/019060, dated Jun. 5, 2019.
Search Report and Written Opinion for Application No. PCT/IB2020/000932, dated Jul. 29, 2021.
Search Report and Written Opinion for Application No. PCT/IB2020/000942, dated Aug. 10, 2021.
European Search Report, EP19756905, dated Oct. 18, 2021.
International Search Report and Written Opinion in Application No. PCT/US2022/016809 dated Jul. 27, 2022.
International Search Report and Written Opinion in Application No. PCT/US2022/027695 dated Jul. 27, 2022.
International Search Report and Written Opinion in Application No. PCT/US2022/027200 dated Aug. 19, 2022.
International Search Report and Written Opinion in Application No. PCT/US2022/030094 dated Sep. 16, 2022.
International Search Report and Written Opinion in Application No. PCT/US2022/016831 dated Sep. 29, 2022.
Chinese Office Action in Application No. 201980010758.4 dated Jun. 16, 2023.
Chinese Office Action in Application No. 201980010758.4 dated Sep. 16, 2023.
International Search Report and Written Opinion in Application No. PCT/IB2023/057720 dated Nov. 8, 2023.
International Search Report and Written Opinion in Application No. PCT/IB2023/058417 dated Dec. 7, 2023.
European Search Report in Application No. 22828961.7 dated Mar. 14, 2025.
International Search Report and Written Opinion in Application No. PCT/IB2024/054985 dated Sep. 10, 2024.

* cited by examiner

100

100

100

100

100

200

EXPANDABLE CERVICAL INTERBODY AND INSTRUMENTS THEREOF

CROSS-REFERENCE TO RELATED APPLICATION

This application claims the benefit of and priority to U.S. Provisional Patent Application No. 63/503,859 filed May 23, 2023, the entire disclosure of which is incorporated by reference herein.

In one aspect, the present technology is generally related to an externally driven and expandable implant for use in a medical procedure that may, for example, be related to the spine and more specifically may be useful as an intervertebral implant. In another aspect, the present technology is generally related to a surgical tool for inserting and expanding the externally driven and expandable intervertebral implant. In some embodiments, disclosed implants and surgical tools may form a system that may be used in an anterior cervical discectomy and fusion (ACDF) procedure although other uses in other areas of the spine or between two bones are also contemplated.

BACKGROUND

Mechanically operated interbody implants may be used to align and/or realign a patient's spine during a medical procedure and/or for purposes of fusion, degenerative tissue and/or trauma/repair procedures. Conventional expandable implants designed for the thoracic and lumbar region of the spine often include top and bottom endplates and a mechanical means to separate the top and bottom endplates. The mechanical mechanisms to separate the top and bottom endplates are often cumbersome and require a large footprint that is often unsuitable, for example, for ACDF type surgeries of the cervical portion of the spine. Many currently available ACDF type implants may be limited in their ability to optimize the adjustment of lordosis or sagittal alignment of the vertebral bodies because they may rely on a fixed lordotic angle between the superior/cephalad and inferior/caudad faces of the device.

SUMMARY

The techniques of this disclosure generally relate to an expandable implant including a superior endplate and an inferior endplate hingedly coupled and which may further include a locking element to secure the inferior endplate and superior endplate in a particular configuration, for example. The superior and inferior endplates may be moved in a multitude of expanded and/or lordosed or kyphosed or otherwise angled configurations via an external surgical tool for example.

In one aspect, the present disclosure provides for an expandable implant movable between a contracted position (closed position) and an expanded position, for example. The expandable implant may include an expandable body extending from a proximal end to a distal end in a proximal-to-distal direction (may also be referred to as an anterior-to-posterior direction depending on surgical technique), extending from a first lateral side to a second lateral side in a widthwise direction, and extend from a superior endplate to an inferior endplate in a heightwise direction (may also be referred to as a cephalad-to-caudal and/or vertical direction depending on surgical technique), for example. In various embodiments, the expandable body may be defined by a superior endplate and an inferior endplate that are hingedly connected, for example. In various embodiments, the inferior endplate may include a support frame having a proximal surface and a distal surface, a wedge channel, and a hinge member. In some embodiments, the superior endplate may include an arcuate channel, a ramp having an inclined surface coaxially in line with a support frame, and a wedge pin groove. In some embodiments, the expandable implant may comprise a drive wedge disposed between the superior endplate and the inferior endplate having a bearing surface on an upper end thereof configured to slide across the inclined ramp and a tang on a lower end thereof configured for disposal within the wedge channel. In various embodiments, the implant may include an expansion screw extending through the support frame and being operatively coupled to the wedge so that when the expansion screw is rotated, the wedge is linearly translated in a longitudinal direction thereby expanding the implant.

In another aspect, the disclosure provides for a system including a medical implant and a surgical tool, for example. The system may include an expandable implant movable between a contracted position and an expanded position, for example. In various embodiments, the expanded position may also refer to a distracted and angled orientation of the superior endplate and inferior endplate. The expandable implant may include an expandable body extending from a proximal end to a distal end in a proximal-to-distal direction and extending from a first lateral side to a second lateral side in a widthwise direction, for example. In various embodiments, the expandable body may be defined by a superior endplate and an inferior endplate that are hingedly connected, for example. In various embodiments, the inferior endplate may include a support frame having a proximal surface and a distal surface, a wedge channel, and a hinge member. In some embodiments, the superior endplate may include an arcuate channel, a ramp having an inclined surface coaxially in line with a support frame, and a wedge pin groove. In some embodiments, the expandable implant may comprise a drive wedge disposed between the superior endplate and the inferior endplate having a bearing surface on an upper end thereof configured to slide across the inclined ramp and a tang on a lower end thereof configured for disposal within the wedge channel. In various embodiments, the implant may include an expansion screw extending through the support frame and being operatively coupled to the wedge so that when the expansion screw is rotated, the wedge is linearly translated in a longitudinal direction thereby expanding the implant. In various embodiments, the system may also include a surgical tool for inserting and expanding the implant and tightening the expansion screw while the implant is expanded at a desired height, position, and/or angle. In some embodiments, the surgical tool may include a plunger having a mounting jaw extending in a lengthwise direction from a proximal end thereof to a distal end thereof that engages with the gripping grooves of disclosed expandable implants to insert, and release disclosed implants. In various embodiments, the surgical tool may include a drive shaft having a drive end disposed within hollow aperture of the plunger to rotate the expansion screw and expand the implant at a desired height, position and/or angle. Furthermore, in various embodiments, the drive end may have a size and shape generally corresponding to a size and shape of a drive feature of the expansion screw. In some embodiments, the mounting jaw may have a size and shape generally corresponding to the shape of the gripping grooves of the expandable implant. In various embodiments, the surgical tool may include an angle indicator ring to identify the angle of inclination of the expanded implant.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 29 is a reference drawing showing the human spine of which various disclosed implant embodiments may be installed in.

DETAILED DESCRIPTION

Figure 1:
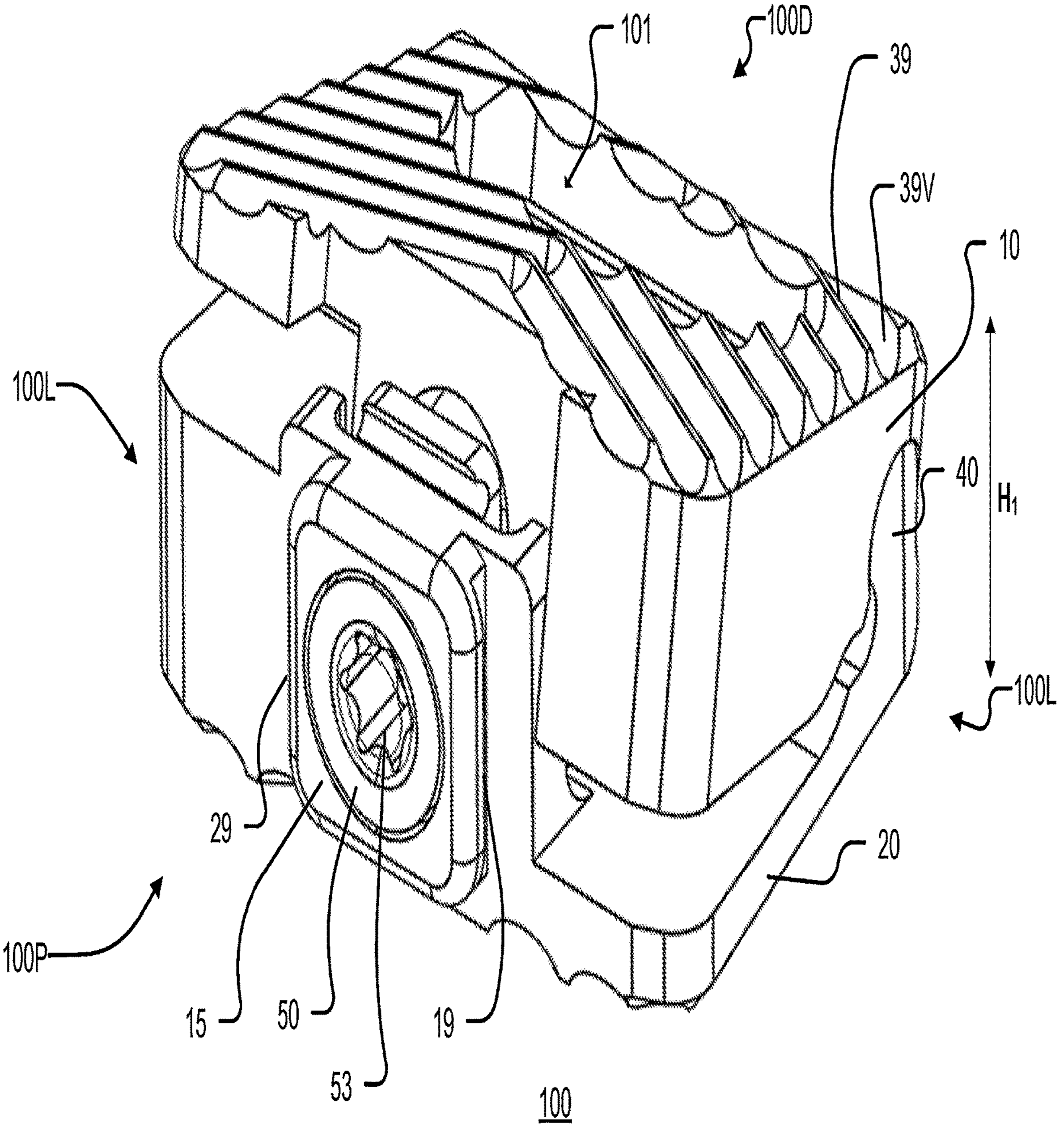
FIG. 1 is a perspective view of an expandable implant.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise. The term "about" may also be used herein to emphasize this meaning and if a value and/or a range of values is provided in the specification or claims with the modifier "about" a meaning of +/− ten percent (10%) to those provided values are encompassed by the meaning of "about," unless the context clearly indicates otherwise.

Referring to FIGS. 1-28B generally, various embodiments and views of an expandable implant 100 and corresponding surgical tool 200 are disclosed. The components of expandable implant 100 and surgical tool 200 can be fabricated from biologically acceptable materials suitable for medical applications, including metals, synthetic polymers, ceramics, and bone material and/or their composites. For example, the components, individually or collectively, can be fabricated from materials such as stainless steel alloys, commercially pure titanium, titanium alloys, Grade 5 titanium, super-clastic titanium alloys, cobalt-chrome alloys, superelastic metallic alloys (e.g., Nitinol, super elasto-plastic metals, such as GUM METAL™), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyactide, polyglycolide, polytyrosine carbonate, polycaroplactohe, polylactic acid or polylactide and their combinations.

In various embodiments, components may be coated with a ceramic, titanium, and/or other biocompatible material to provide surface texturing at (a) the macro scale, (b) the micro scale, and/or (c) the nano scale, for example. Similarly, components may undergo a subtractive manufacturing process providing for surface texturing configured to facilitate osscointegration and cellular attachment, and osteoblast maturation. Example surface texturing of additive and subtractive manufacturing processes may comprise (a) macro-scale structural features having a maximum peak-to-valley height of about 40 microns to about 500 microns, (b) micro-scale structural features having a maximum peak-to-valley height of about 2 microns to about 40 microns, and/or (c) nano-scale structural features having a maximum peak-to-valley height of about 0.05 microns to about 5 microns. In various embodiments, the three types of structural features may be overlapping with one another, for example. Additionally, such surface texturing may be applied to any surface, e.g., both external exposed facing surfaces of components and internal nonexposed surfaces of components. Further discussion regarding relevant surface texturing and coatings is described in, for example, U.S. Pat. No. 11,096,796, titled Interbody spinal implant having a roughened surface topography on one or more internal surfaces, and filed on Mar. 4, 2013—the entire disclosure of which is incorporated herein by reference in its entirety. Accordingly, it shall be understood that any of the described coating and texturing processes of U.S. Pat. No. 11,096,796, may be applied to any component of the various embodiments disclosed herein, e.g., the exposed surfaces and internal surfaces of endplates. Another example technique for manufacturing an orthopedic implant having surfaces with osteoinducting roughness features including micro-scale structures and nano-scale structures is disclosed in U.S. Pat. No. 10,821,000, the entire contents of which are incorporated herein by reference. Additionally, an example of a commercially available product may be the Adaptix™ Interbody System sold by Medtronic and comprising a titanium cage made with Titan nanoLOCK™.

Figure 2:
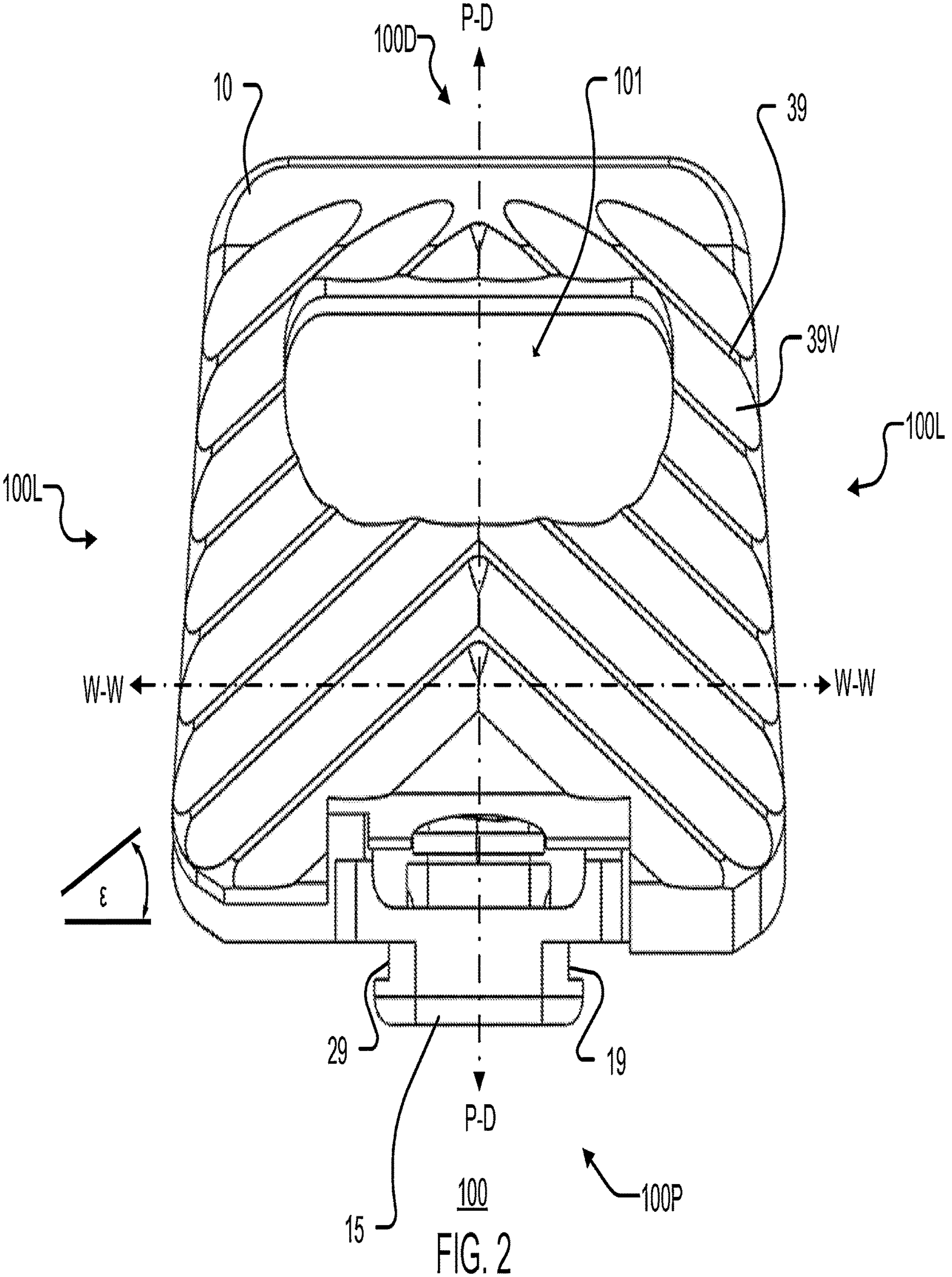
FIG. 2 is a top-down view of an expandable implant.
Figure 3:
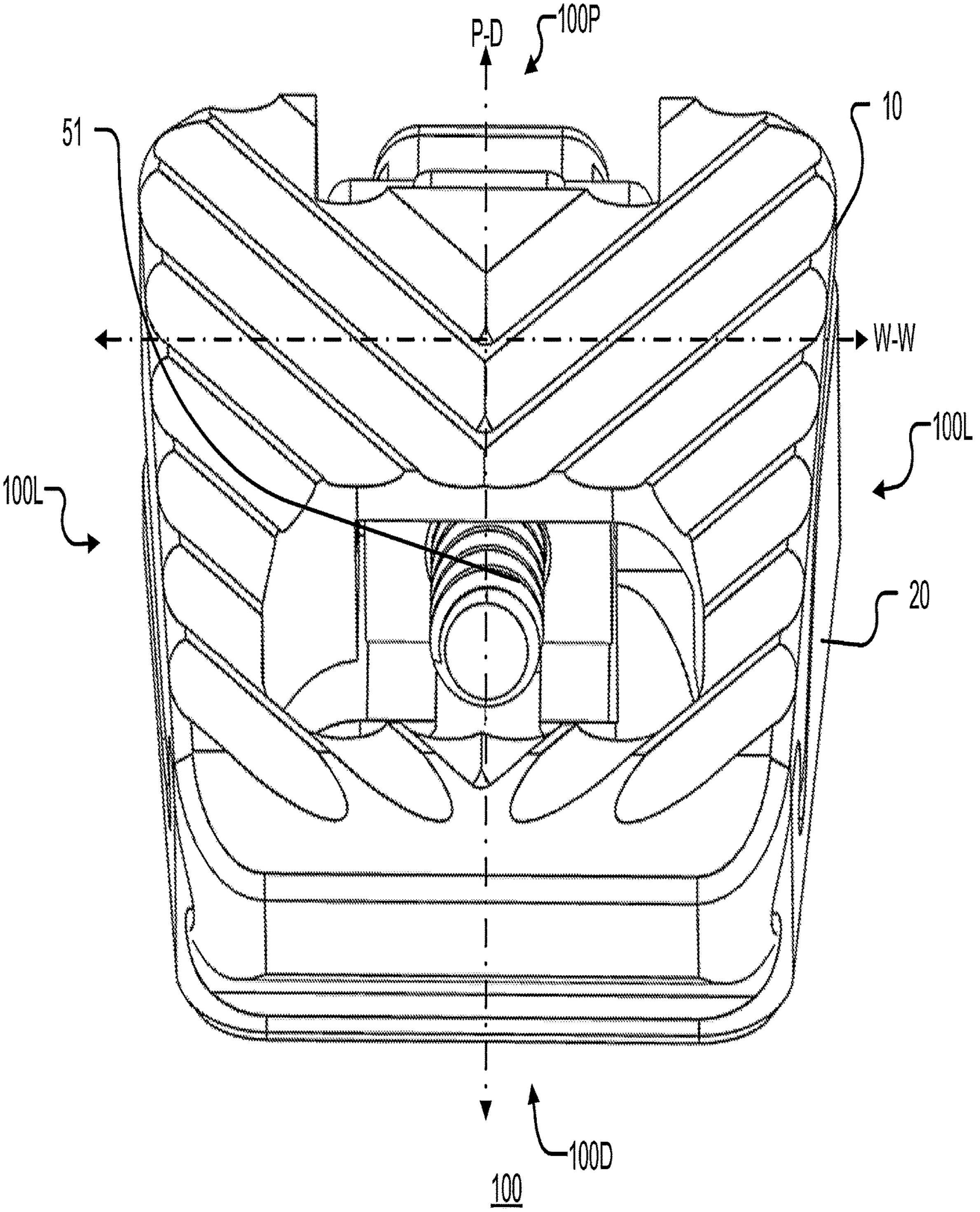
FIG. 3 is an alternative perspective view of an expandable implant.

Referring generally to FIGS. 1-3 various views of an expandable implant, or implant 100 in a collapsed position are illustrated. FIG. 1 is a perspective view of an expandable implant 100 having a first height $H_1$ or thickness between the superior endplate 10 and inferior endplate 20. FIG. 2 is a top-down view of an expandable implant 100. FIG. 3. Is another perspective of an expandable implant 100. In the example embodiment, expandable implant 100 may include a proximal end 100P, a distal end 100D, and lateral sides 100L.

Figure 15:
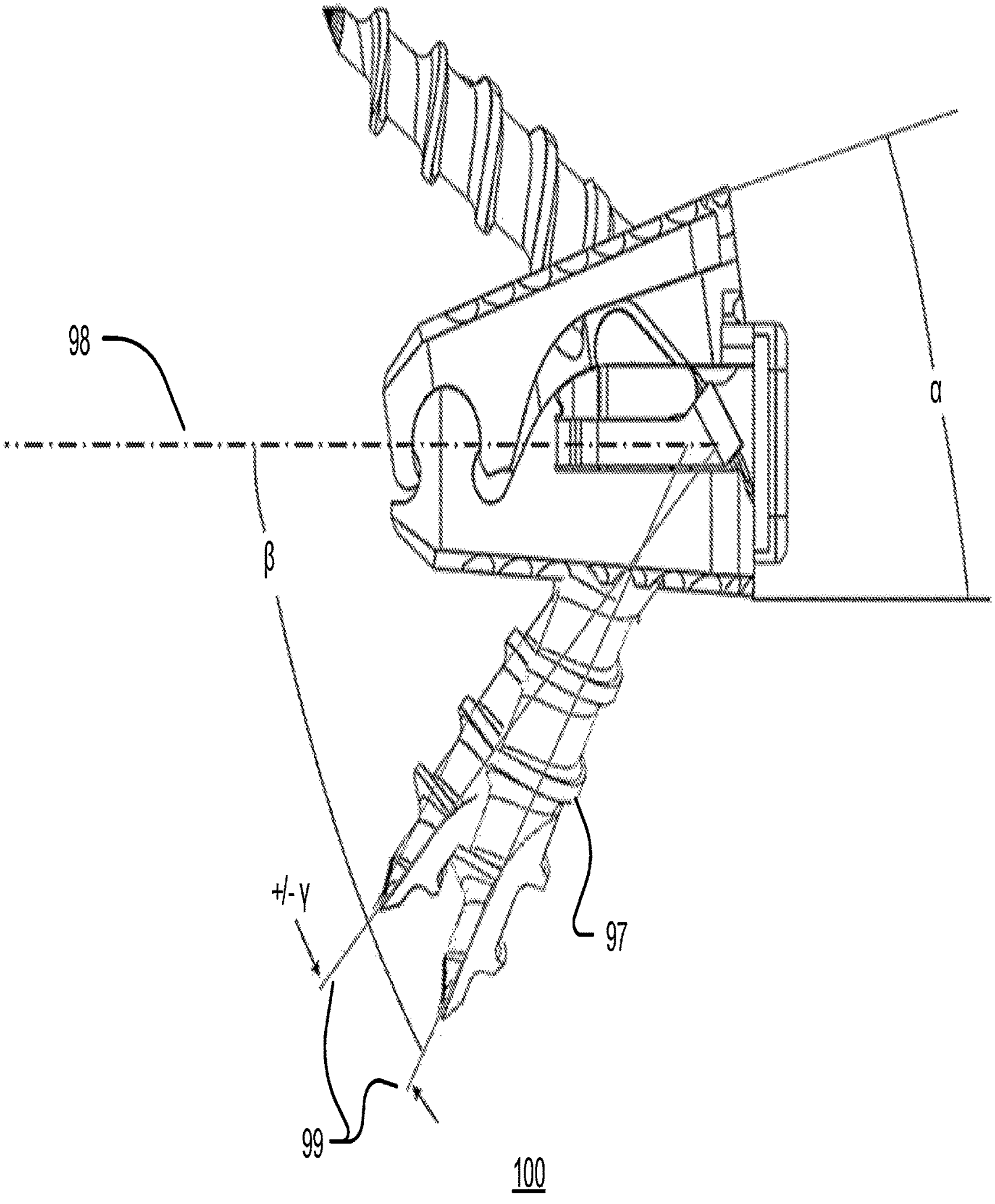
FIG. 15 is a side view of an expandable implant showing a bone screw trajectory.

In various embodiments, and as illustrated in FIGS. 1-2, gripping grooves 19, 29 may be present at the proximal end 100P of implant 100 for coupling with corresponding prongs of a surgical tool 200 (see FIGS. 21-28) disclosed herein. In various embodiments, the number of gripping grooves may vary, e.g., gripping groves may be 2, 3, 4, or more. In various embodiments, implant 100 may be referred to as an externally driven expandable implant because an end user or surgeon may use a surgical tool to open and close implant, e.g., expandable implant 100. A surgical tool 200 may adjust the lordotic angle of implant 100 by actuation of an expansion mechanism as will be explained in detail with respect to FIGS. 21-28. Implant 100 may be expanded to a patient specific and appropriate lordotic angle $\alpha$, as seen in FIG. 15 (also referred to as angle of inclination) by actuation of the expansion mechanism. Thereafter, a surgeon may lock the implant 100 in place by securing bone screws 97 into the adjacent vertebra $V_1$ and $V_2$ (see FIGS. 18-20). In some embodiments, superior endplate 10 may be referred to as a "cephalad" endplate, and inferior endplate 20 may be referred to as a "caudal" endplate consistent with standard medical terminology, e.g., particularly for an ACDF implant region of interest.

In some embodiments, implant 100 may include angled engagement features 39. In the example embodiment, engagement features 39 extend diagonally across the exposed uppermost surface of superior endplate 10 and across the exposed lowermost surface of inferior endplate 20. The engagement features 39 comprise flattened top rails that are sequentially spaced apart with rounded bottom valleys 39V therebetween. As seen best in the top-down view of FIG. 2, the engagement features 39 of the superior endplate 10 are oriented at an angle $\varepsilon$ with respect to a proximal face of the superior endplate 10. Similarly, the engagement features 39 of the inferior endplate 20 are oriented at an angle $\varepsilon$ with respect to a proximal face of the inferior endplate 20. In various embodiments, the angle $\varepsilon$ may be about 20 to about 40 degrees and in at least one embodiment the angle $\varepsilon$ may be angled at about 30 degrees. At least one advantage of this orientation may be a relatively greater resistance and/or suppression of expulsion of the implant 100 relative to embodiments in which engagement features solely extend horizontally across the implant 100. In the example embodiment, by orienting the engagement features 39 diagonally, the implant 100 may resist expulsion in multiple directions, e.g., forward flexion/extension and lateral bending. In the example embodiment, it may be seen that the engagement features 39 take a "V" shape pattern across the respective outer surface of the superior endplate 10 and inferior endplate 10. Additionally, it may be seen that an apex of the engagement features 39, where a change in direction occurs, is substantially centered along a middle axis that bisects implant 100 in the proximal-to-distal direction P-D.

At least one advantage of relying on an external tool to adjust a lordotic angle of implant 100 may be the case in expansion and the setting of the implant at a particular lordotic angle by a corresponding surgical tool 200 with a calibrated indicator. Expansion of the implant 100 with a moving mechanism may also be gentler on the patient anatomy due to a relatively consistent and controlled expansion versus other tools relying on jaws, forceps, or reverse pliers. Optimization of the footprint of the expansion mechanism is desirable to ensure that implant 100 may have a relatively large void space in the interior thereof, which may facilitate a fusion process during an ACDF procedure. For example, implant 100 may have a relatively large internal volume 101 that is open through the superior endplate 10 and inferior endplate 20 which may be packed with bone graft material, for example. In this vein, a moving direction of a wedge and expansion mechanism should be optimized to keep the internal volume 101 as large as reasonably possible.

As illustrated in FIGS. 2-3, implant 100 may extend in a proximal-to-distal direction from the proximal end 100P to the distal end 100D. In the art, the proximal-to-distal direction may also be referred to as a longitudinal direction and/or an anterior-to-posterior direction depending on surgical technique and final orientation. Similarly, the proximal end 100P may be referred to as an anterior end depending on surgical technique and final orientation and the distal end 100D may be referred to as a posterior end depending on surgical technique and final orientation. As illustrated, the proximal-to-distal direction may extend parallel to axis P-D through the center of the implant 100, for example. Implant 100 may extend in a widthwise direction (also referred to as lateral direction or transverse direction) from the first lateral side 100L to the second lateral side 100L through axis W-W through the center of implant 100 and the center of expansion screw 50, for example. The axis P-D may be perpendicular and/or substantially perpendicular to the axis W-W. For example, the proximal-to-distal direction may be perpendicular to the widthwise direction. Additionally, the width of the implant may taper from a proximal end 100P where it is widest towards a distal end 100D where it is narrowest to better conform to a disc space. In various embodiments, implant 100 may extend from a superior endplate 10 to an inferior endplate 20 in a heightwise direction (may also be referred to as a cephalad-to-caudal direction and/or vertical direction depending on surgical technique and final orientation).

Figure 4:
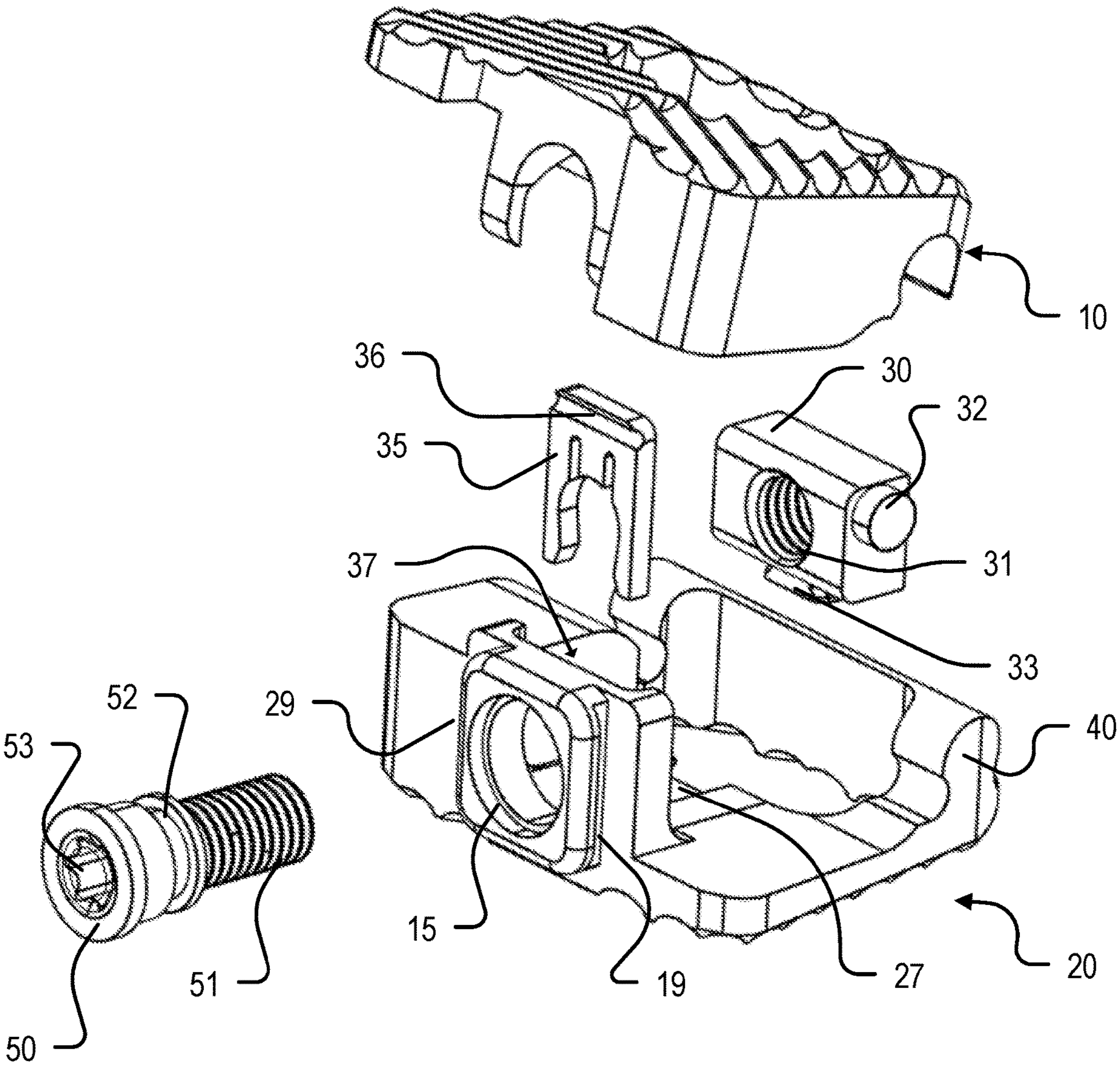
FIG. 4 is an exploded parts view of an expandable implant.

FIG. 4 is a perspective exploded parts view of an expandable implant 100. In the example embodiment, an expansion mechanism including an expansion screw 50 and wedge 30 is illustrated. Expansion screw 50 may include an external thread 51 on an outside circumferential surface thereof, for example. In some embodiments, a recess 37 is formed in the proximal surface of the frame portion 15, and a head portion of the drive expansion screw is seated within the recess 37. In some embodiments, expansion screw 50 may be disposed in recess 37 and may include an expansion screw groove 52 that mates with retaining clip 35 to support the expansion screw 50 in place. For example, this configuration may constrain relative linear movement of the expansion screw 50 only allowing the rotation of the expansion screw 50 thereby proximally translating wedge 30 separating superior endplate 10 from inferior endplate 20. In various embodiments, the retaining clip 35 and the recess 37 are configured to provide friction on the expansion screw to prevent the expansion screw from inadvertently rotating thereby preventing unwanted expansion and contraction of the implant post-installation.

In some embodiments, retaining clip 35 may have a retaining clip groove 36 that faces the proximal direction when seated in recess 37. In various embodiments, a surgeon may lift up on the retaining clip 35 via the clip groove 36 and pull the clip out thereby uncoupling from the expansion screw groove 52. The external thread 51 of expansion screw 50 may have a size and shape generally corresponding to the support frame 15, and threaded portion 31 of drive wedge 30, for example. In various embodiments, drive wedge 30 may include a tang 33 on a lower end which is operatively engaged with and/or coupled with channel 27 on inferior endplate 20 (see also FIG. 6). In this way, the wedge 30 may slide back and forth in the proximal to distal direction P-D and be operatively engaged with the inferior endplate 20. In the example embodiment tang 33 and channel 27 may be operatively coupled by a dovetail configuration although other configurations are contemplated, i.e., tongue and groove etc. In various embodiments, expansion screw 50 may include a drive feature 53 disposed with respect to the proximal end of the expansion screw 50, i.e., the head portion of the expansion screw. In the example embodiment, the drive feature may take a hexalobular shape, although various other shapes such as hexagonal, polygonal shapes having at least three sides, Torx, etc. are also contemplated. In some embodiments, a surgical tool too having a corresponding drive end may be coupled to cause rotation of expansion screw 50 via the drive feature.

Figure 5:
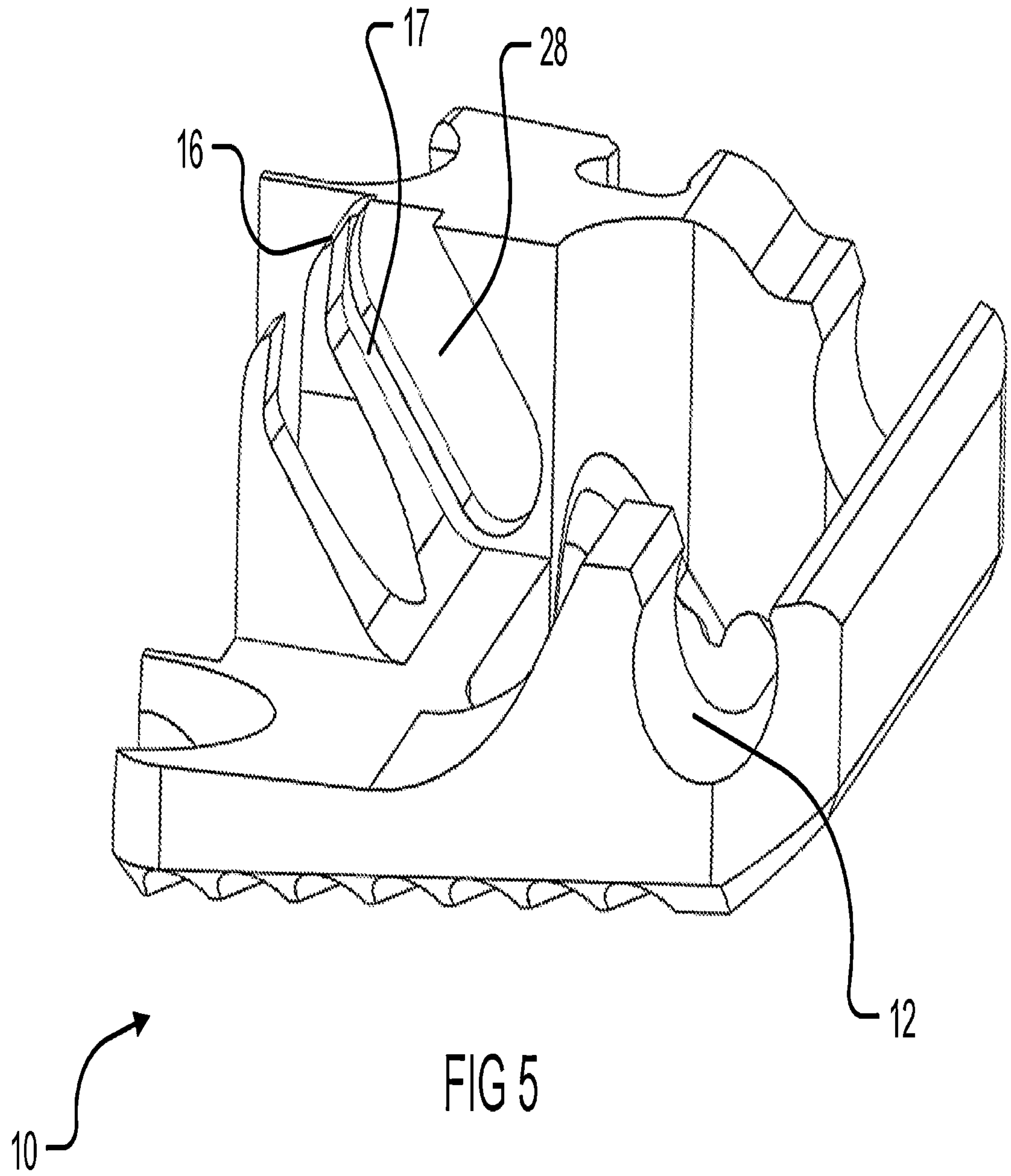
FIG. 5 is a perspective view of the interior of a superior endplate of an expandable implant.

FIG. 5 is a perspective view of the interior surfaces of a superior endplate 10. In the example illustration, it is shown that the distal end of superior endplate 10 includes an arcuate channel 12 extending in the widthwise direction of which the hinge member 40 of the inferior endplate may be disposed inside of. Superior endplate 10 may also include a ramp 16 comprising an inclined surface 17 that is sloped from the distal side of the superior endplate 10 towards the proximal side of the superior endplate 10. In some embodiments, as the expansion screw 50 is rotated and the wedge 30 is translated, the inclined surface 17 of ramp 16 rides on the top of the drive wedge 30. For example, expansion screw 50 may be screwed in the threaded portion 31 of wedge 30 such that rotation thereof may linearly translate drive wedge 30. In the example embodiment, rotation of expansion screw 50 may draw the wedge 30 towards the proximal end 100P of implant 100 thereby pushing the superior endplate 10 upward in the vertical direction and pivoting the implant due to the incline surface 17 of the ramp 16. In various embodiments, wedge pin 32 may extend in a lateral direction from a side surface of wedge 30 and be disposed within wedge pin groove 28 to provide an additional mating feature between wedge 30 and superior endplate 10. In this way, wedge pin 32 may ride upward at an inclined angle that corresponds to an inclined angle of surface 17. For example, wedge pin 32 may ride along groove 28 in a proximal direction to drive the superior endplate 10 upward while allowing superior endplate 10 to pivot around a pivoting axis defined by the connection between hinge member 40 and channel 12. In various embodiments, the cooperation between wedge pin 32 positioned in groove 28 may define the range of angulation of implant 100. In various embodiments, wedge pin 32 and groove 28 are configured to prevent an overexpansion of the implant and to maintain an angular position of the superior endplate 10 relative to the inferior endplate 20. For example, a first end of groove 28 may define a lowest extent of the range of angulation of implant 100 and second end opposite the first end may define a greatest extent of the range of angulation of implant 100. At least one advantage may be to prevent superior endplate 10 from expanding too much.

Figure 6:
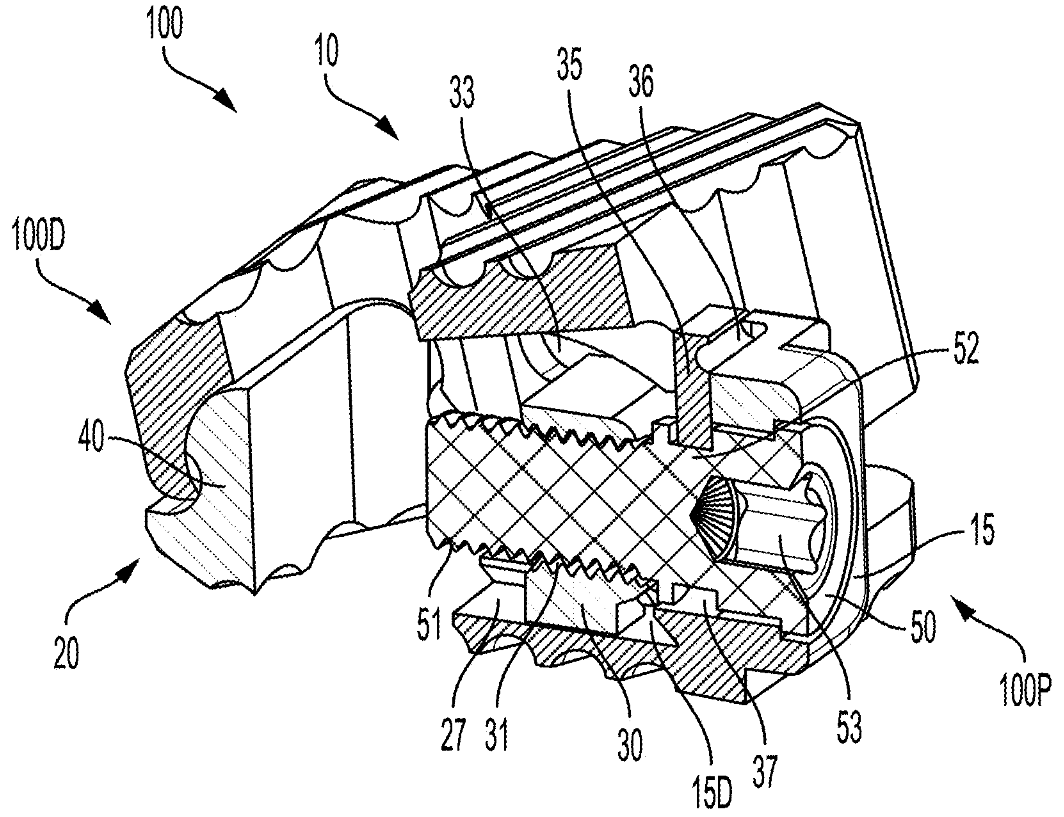
FIG. 6 is a perspective cross section view of an expandable implant

FIG. 6 is a perspective cross section view of expandable implant 100. In the example embodiment, it is shown that the superior endplate 10 and inferior endplate 20 are coupled together by a hinge member 40, and drive wedge 30 may be positioned behind the proximal face of inferior endplate 20. For example, the drive wedge may be positioned in the internal space of implant 100 behind the support frame 15 of the inferior endplate and within channel 27. Additionally, expansion screw 50 may extend through an aperture in the proximal face of the inferior endplate 20 such that the external thread 51 of the expansion screw 50 may engage with the threaded portion 31 of the drive wedge 30. In various embodiments, the expansion screw 50 engaged with the drive wedge 30 dispose within channel 27 constrains the lateral movement of the superior endplate 100 along W-W axis about hinge member 40 thereby preventing disassembling of the superior endplate 100 from inferior endplate 200. Additionally, retaining clip 35 may be seated in a corresponding recess 37 of the inferior endplate to constrain relative linear movement of the expansion screw 50. In this way, when expansion screw 50 is rotated the expansion screw 50 may remain in place while the wedge 30 is linearly translated towards the proximal end 100P of implant and slides across the inclined surface 17 of ramp 16 thereby separating superior endplate 10 from inferior endplate 20 and expanding implant 100. In the example embodiment, support frame 15 may take a generally rectangular shape and extend from the proximal face of the inferior endplate to form the recess 37 for supporting the clip 35 and to have various gripping portions as will be explained in more detail below.

Figure 7:
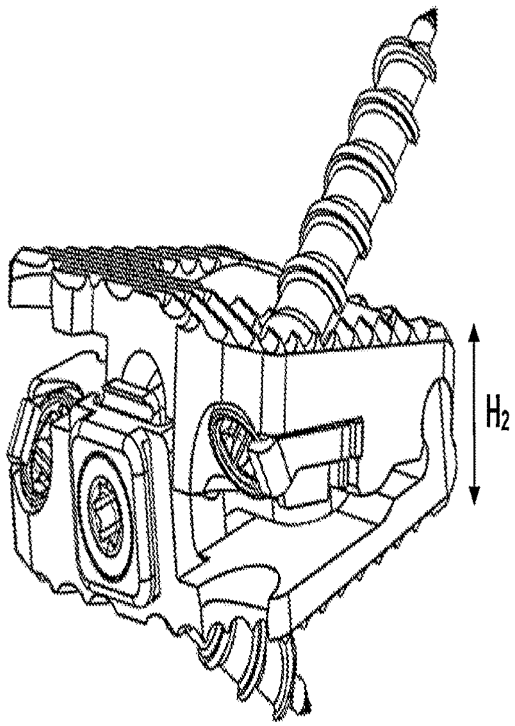
FIG. 7 is a perspective parts view of a second expandable implant.
Figure 8:
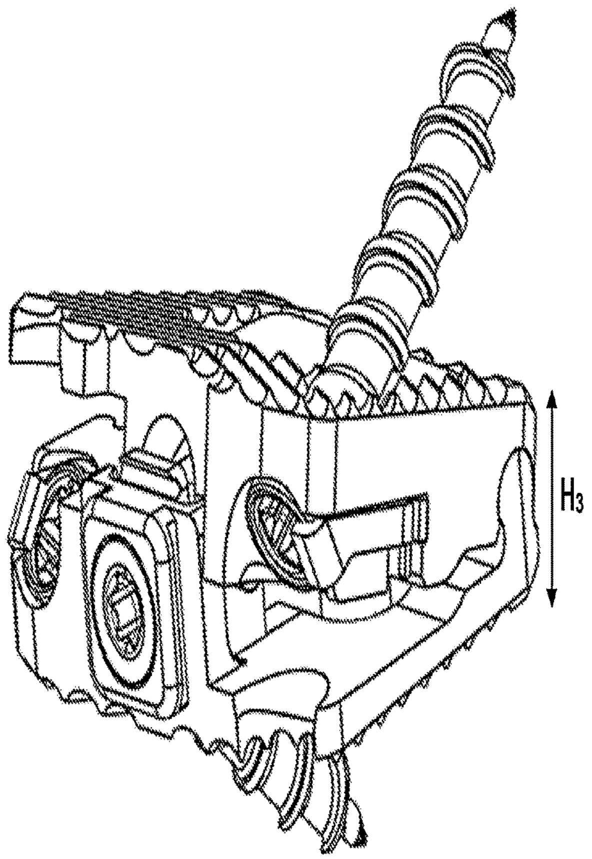
FIG. 8 is a perspective parts view of a third expandable implant.
Figure 9:
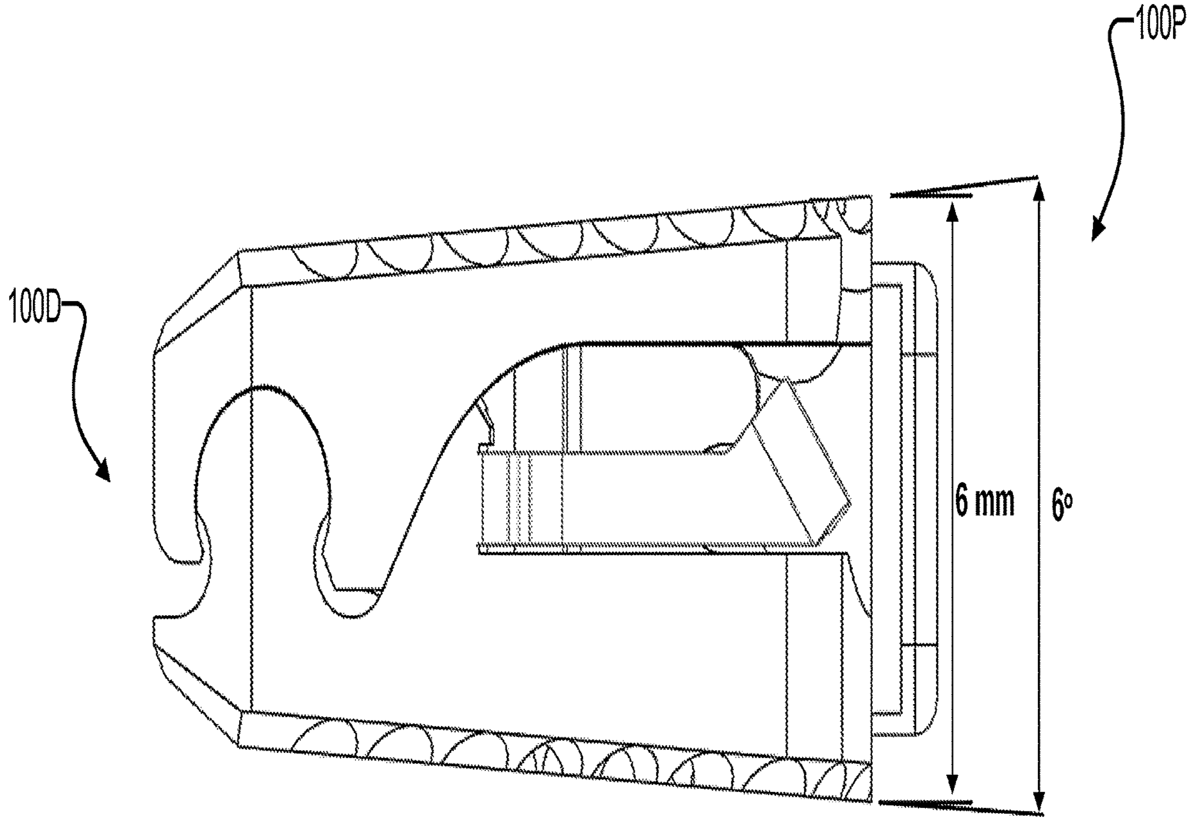
FIG. 9 is a side view of an expandable implant embodiment in a contracted position.
Figure 10:
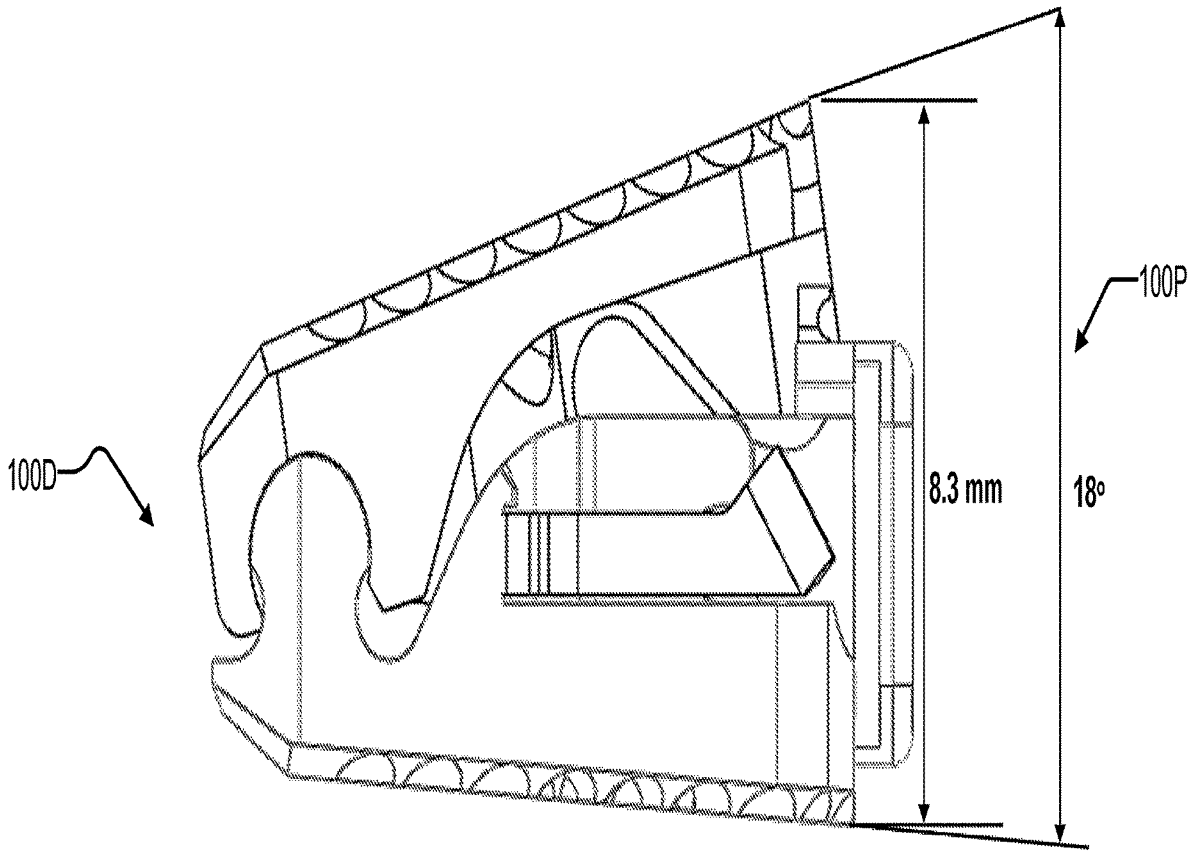
FIG. 10 is a side view of an expandable implant embodiment in an open position.

Referring generally to FIGS. 7-10, various views of example embodiments of expandable implant 100 are illustrated. FIG. 7 is a perspective view of a second expandable implant, FIG. 8 is a perspective view of a third expandable implant. In the series of illustrations, it is shown that various embodiments in accordance with the principles of this disclosure may be variously sized in length, width, height, and range of available expansion depending on the particular location in a human body and the particular patient-specific human anatomy. For example, FIG. 7 illustrates a second expandable implant 100 having a second height $H_2$ (thickness) between the superior endplate 10 and inferior endplate 20 and a second width $W_2$, FIG. 8 illustrates a third expandable implant 100 having a third height $H_3$ (thickness) and a third width $W_3$. In at least some embodiments, $H_1$ (see FIG. 1) may be about 6 mm, $H_2$ may be about 7 mm, $H_3$ may be about 8 mm, for example. In various embodiments, an angle of inclination between the superior endplate 10 and inferior endplate 20 may be about 6 degrees to about 20 degrees in an expanded configuration depending on a size of implant 100, e.g., an angled and/or inclined configuration (FIGS. 9-10).

Figure 11:
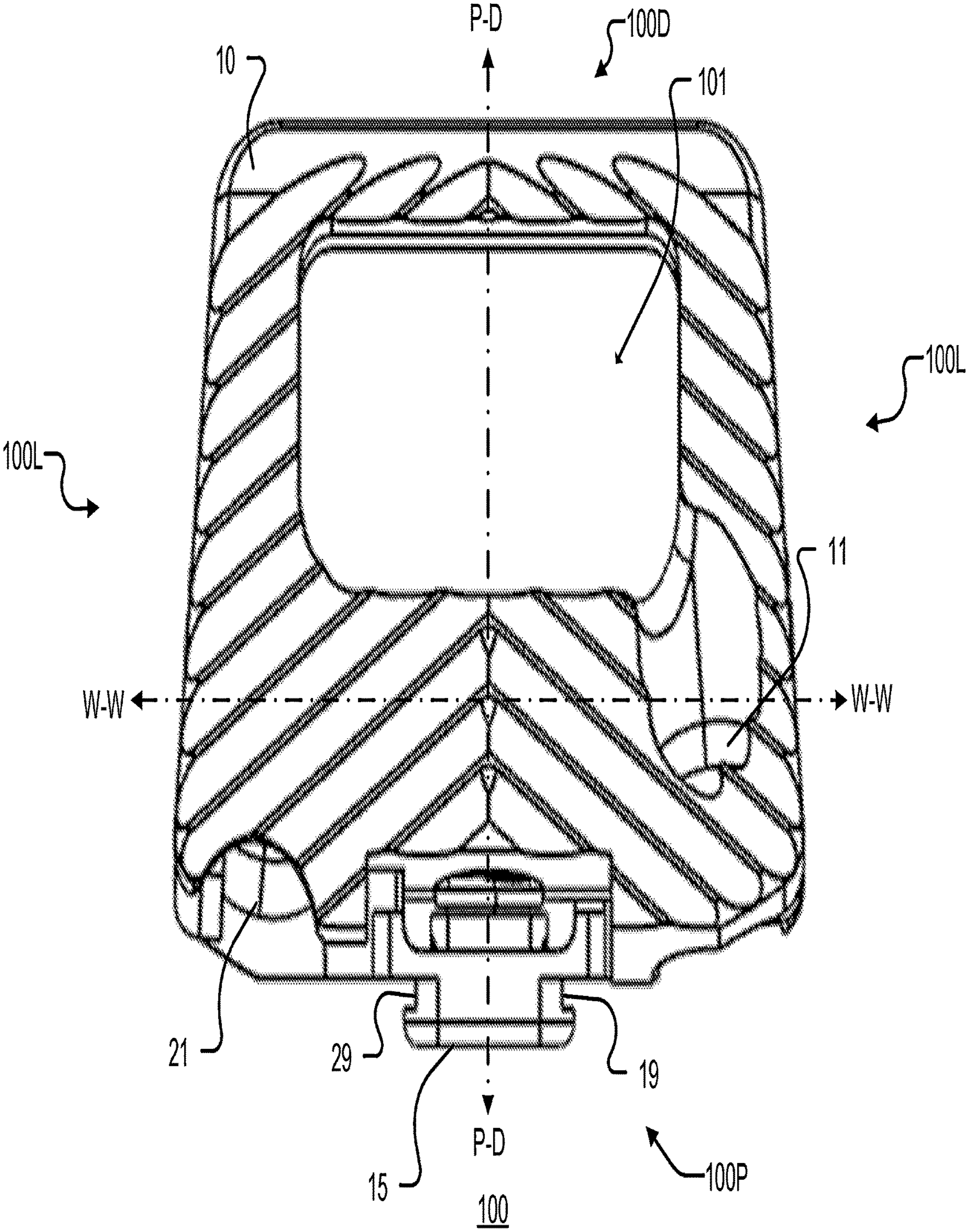
FIG. 11 is a top-down view of an expandable implant.
Figure 12:
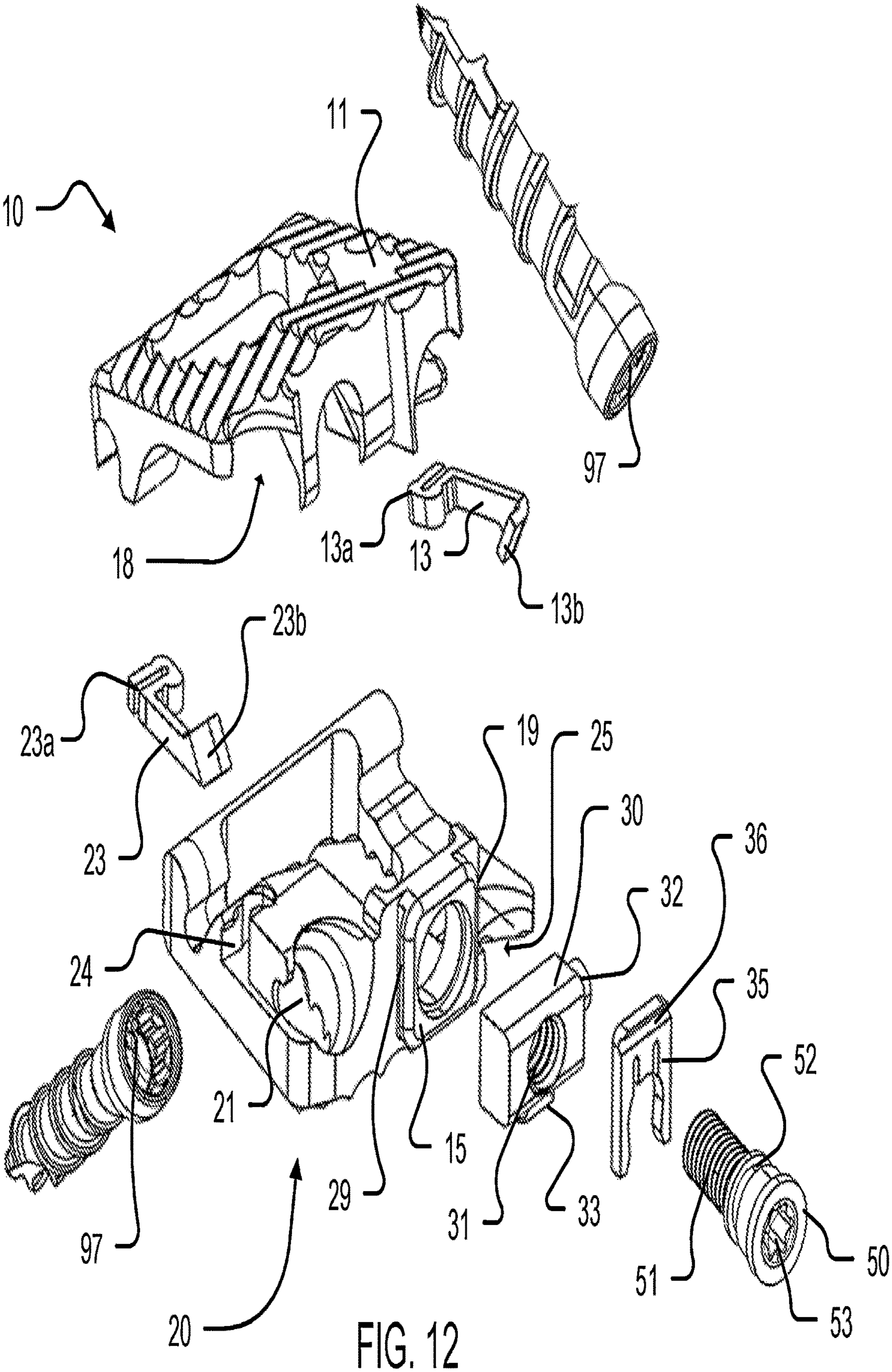
FIG. 12 is an exploded parts view of an expandable implant.

FIG. 11 is a top-down view of another embodiment of an expandable implant 100, and FIG. 12 is a perspective exploded parts view of the expandable implant 100 of FIG. 11. This embodiment may include the same, similar, and/or substantially the same features and components as previously explained. Accordingly, duplicative description regarding the moving mechanism's wedge 30 and expansion screw 50 will be omitted. This embodiment may include bone screw apertures 11, 21 as will be explained in more detail below.

In the example embodiment, a pair of bone screw apertures 11, 21 may be positioned on the proximal end 100P of implant 100. In various embodiments, a bone screw retention mechanism 13, 23 may be provided adjacent the corresponding bone screw aperture 11, 21. In some embodiments, the bone screw retention mechanism 13, 23 may be referred to as an anti-backout locking mechanism. In the example embodiment, the bone screw retention mechanism 13, 23 may comprise a flexible spring like tab member having an anchor portion 13*a*, 23*a* at a first end that is anchored into a corresponding cavity 24, 14 of a corresponding endplate. Additionally, the bone screw retention mechanism 13, 23 may include a hook portion 13*b*, 23*b* at a second end thereof that has an inclined contact surface. In this way, the bone screw retention mechanism is only anchored to the corresponding endplate at one end thereby allowing it to elastically deform and snap back into place. In operation, the flexible nature of bone screw retention mechanism allows it to flex outward in a lateral direction such that the hook portion moves out of the way seamlessly during the insertion of the bone screw 97 and snaps back over the edge of the head of the bone screw 97 once the bone screw is driven fully into boney anatomy of the patient. For example, as the bone screw 97 is driven in the bone screw aperture 11, 21, the bone screw retention mechanism 13, 23, may automatically flex outward as the head portion of the bone screw contacts the inclined surface of the hook portion 13*b*, 23*b*. Stated another way, the bone screw retention mechanism 13, 23 may be configured to move from a neutral position in which the hook portion covers at least a portion of the bone screw aperture to a splayed position in which the hook portion is moved sufficiently far away from the bone screw aperture to allow a bone screw to be driven therethrough the aperture. After driving of the bone screw, the bone screw retention mechanism may snap back to the neutral position and thereby prevent the already driven bone screw from backing out (see FIGS. 16-17).

Figure 13:
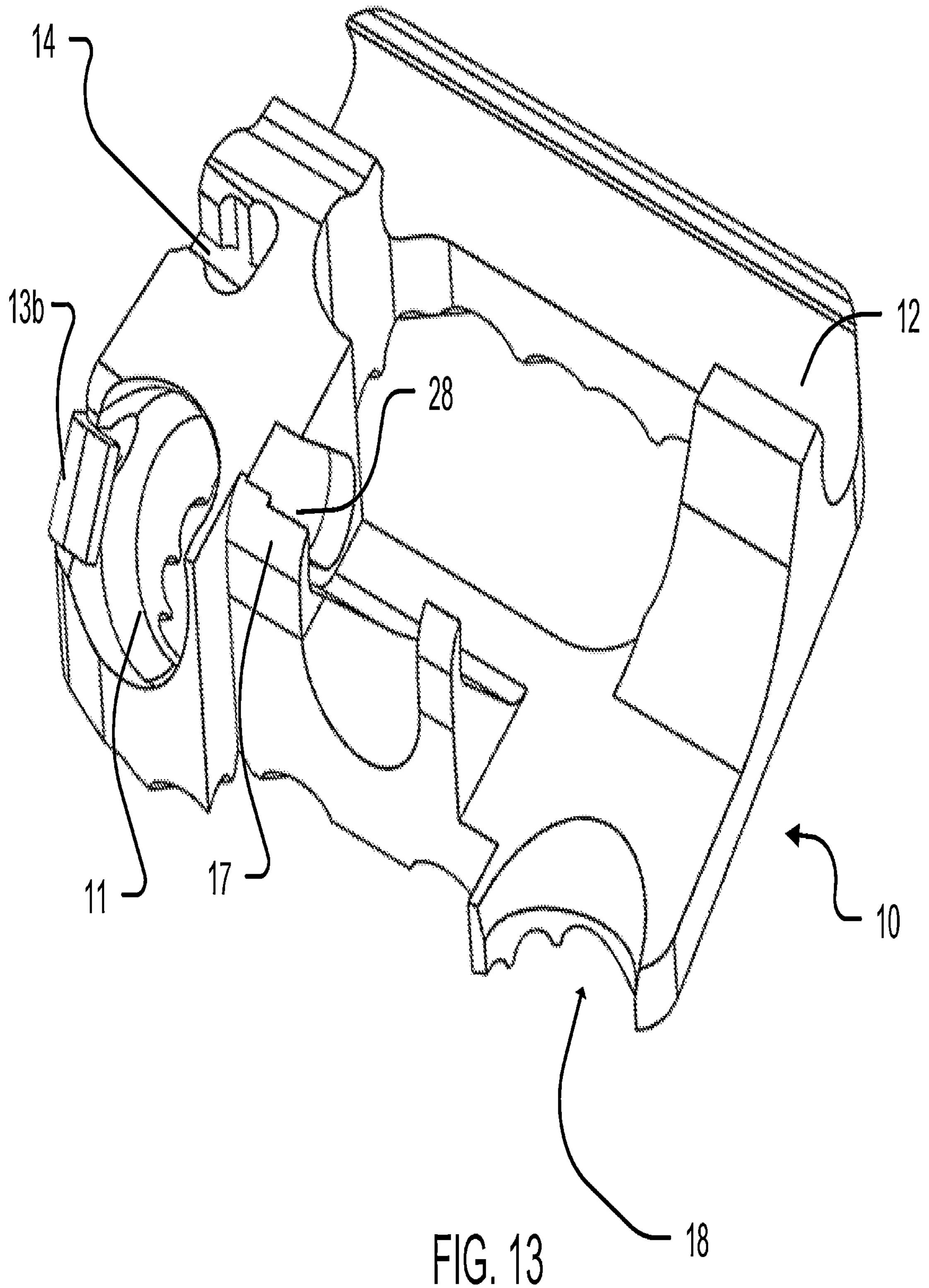
FIG. 13 is a perspective view of the interior of a superior endplate of an expandable implant.
Figure 14:
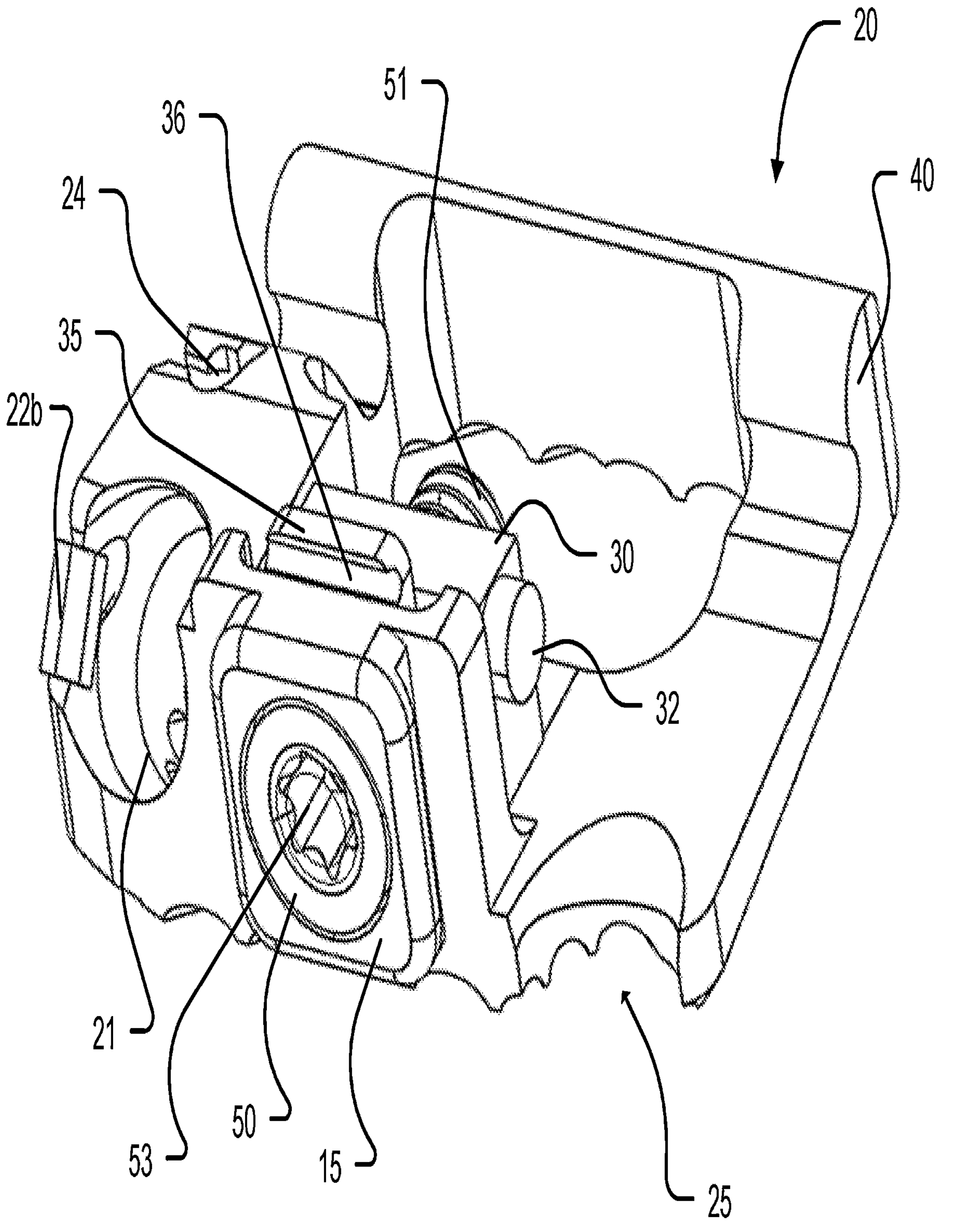
FIG. 14 is a perspective view of the interior of an inferior endplate of an expandable implant.

FIG. 13 is a perspective view of the interior surfaces of a superior endplate 10 including a cavity 14 for supporting a bone screw retention mechanism and FIG. 14 is a perspective view of the interior of an inferior endplate 20 including a cavity 24 for supporting a bone screw retention mechanism. The other features of the interior of the superior endplate 10 and inferior endplate 20 may be configured similarly as explained previously. Accordingly, duplicative description will be omitted. The proximal end of superior endplate 10 may include a cutout 18 that functions as relief area for a corresponding bone screw 97 to be inserted through bone screw aperture 21 of inferior endplate 20 without clashing with the superior endplate 10, for example. Similarly, the proximal end of the inferior endplate 20 may include a cutout 25 that functions as a relief area for a corresponding bone screw 97 to be inserted through bone screw aperture 11 of the superior endplate 10 without clashing with the inferior endplate 20, for example.

FIG. 15 is a side view of an expandable implant 100 in the expanded configuration. In an expanded position, an angle of inclination a may be relatively greater in an expanded position than in the closed configuration, for example. In the illustrated expanded configuration of FIG. 15, a may be about 6 degrees to about 20 degrees. In at least one embodiment, implant height may be about 8.3 mm in a fully expanded position and a may be about 18 degrees, for example. In FIG. 15, it is also shown that a centered or bone screw trajectory 99 of bone screw 97 is at an angle $\beta$ with respect to a transverse plane 98 that crosses through a center of the implant 100 from a first lateral side to a second lateral side, for example. Additionally, the bone screw trajectory 99 may be variable +/− by a degree $\gamma$, for example. In this way, a surgeon has some tolerance to install a bone screw +/−$\gamma$ radially in all directions from the nominal orientation defined by bone screw trajectory 99. In various embodiments, $\beta$ may be about 30 degrees to about 50 degrees and $\gamma$ may be about 2 degrees to about 10 degrees. In the example embodiment, $\beta$ may be about 40 degrees and $\gamma$ may be about 5 degrees.

Figure 16:
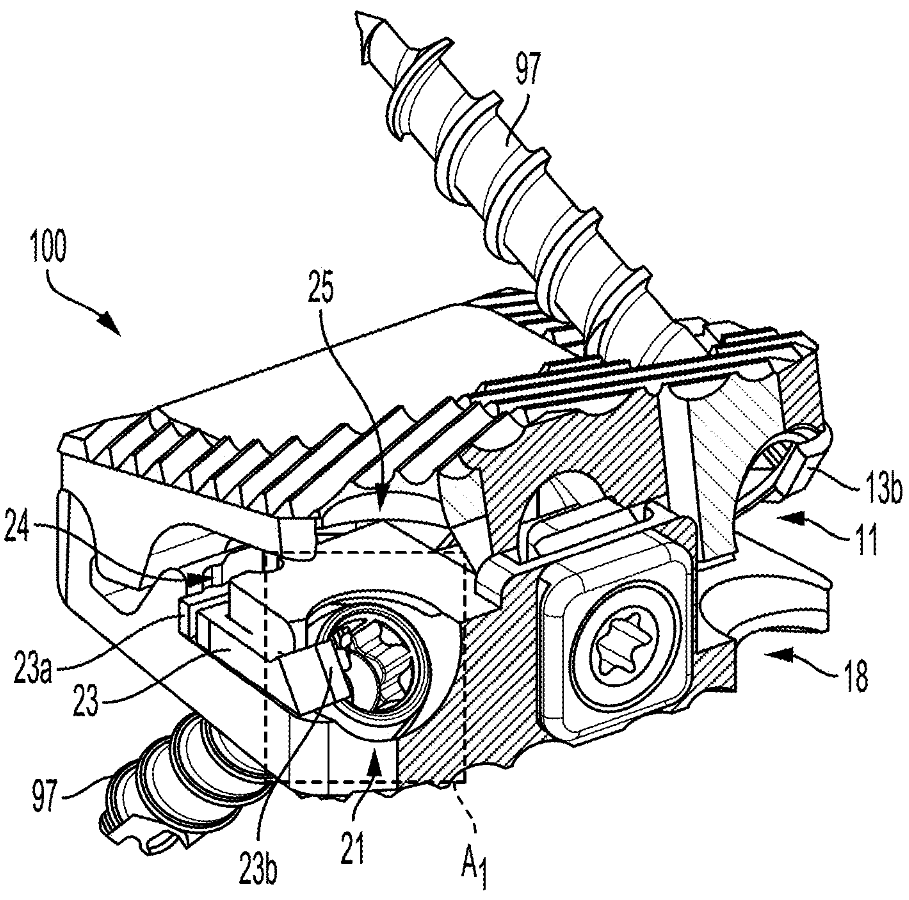
FIG. 16 is a front view of an expandable implant.
Figure 17:
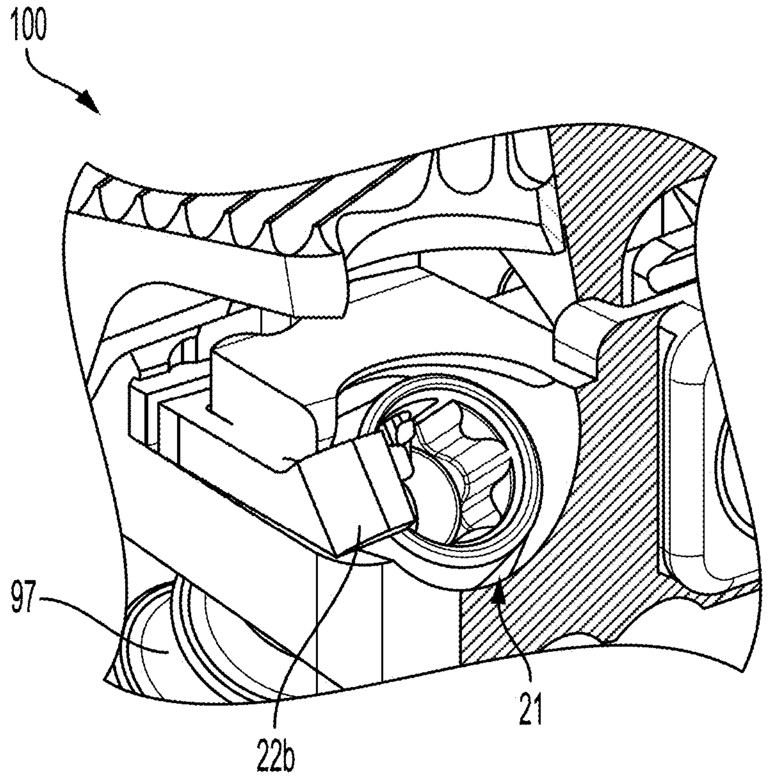
FIG. 17 is a front view of an enlarged area of FIG. 16.

FIG. 16 is a front view of an expandable implant 100 showing an area A1 and FIG. 17 is a front view of the enlarged area $A_1$ of FIG. 16. In the example embodiment, bone screw 97 is in a position extending through bone screw aperture 21 where it cannot back out due to bone screw retention mechanism 23 as explained above. The bone screw retention mechanism 23 includes an anchor portion **23*a* anchored in the corresponding cavity 24 inclined surface in the bone screw aperture 21 such that when bone screw 97 is being installed, an underside of the head portion of bone screw 97 directly contacts the inclined surface thereby pushing the hook portion 23*b* of bone screw retention mechanism 23 laterally outward and away from bone screw aperture 21, for example. Thereafter, when bone screw 97 is installed and the head portion of bone screw 97 is beneath the inclined surface, bone screw retention mechanism 23 may flex back towards bone screw aperture 21 such that it will prevent bone screw 97 from backing out, e.g., a blocking surface of bone screw retention mechanism 23 may contact an upper surface of the head portion of bone screw 97. In the example embodiment, anchor portion 23*a* may resemble a "c" clip (see FIG. 12) having a bulbous end that may be retaining within cavity 24. Additionally, bone screw retention mechanism 23 comprises a flexible hook (or spring tab) 23*b* having an inclined surface that is disposed on a lateral end of implant 100 adjacent bone screw aperture 21. The "c" clip shape of anchor portion 23*a* may be configured to facilitate flexion of the flexible hook 23*b***.

Figure 18:
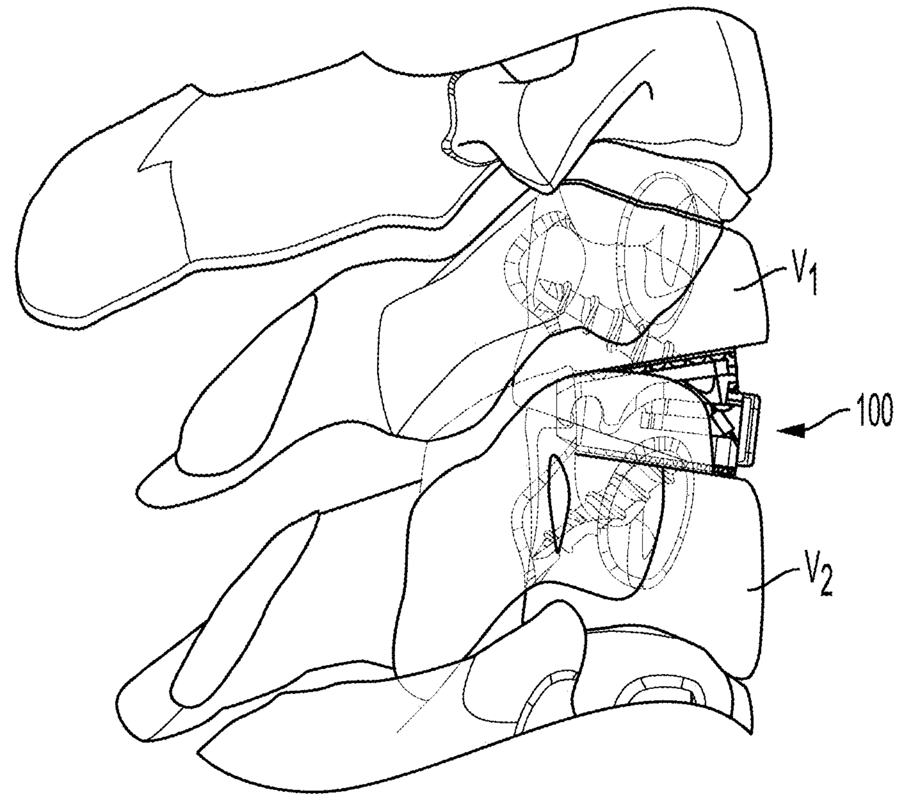
FIG. 18 is a side view of an expandable implant inserted between vertebrae.
Figure 19:
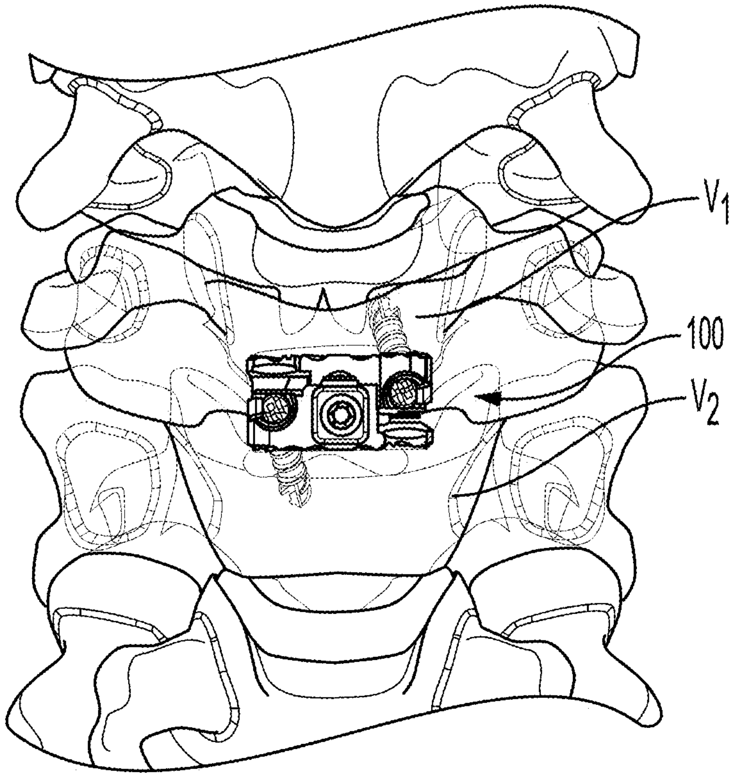
FIG. 19 is a front view of an expandable implant inserted between vertebrae.
Figure 20:
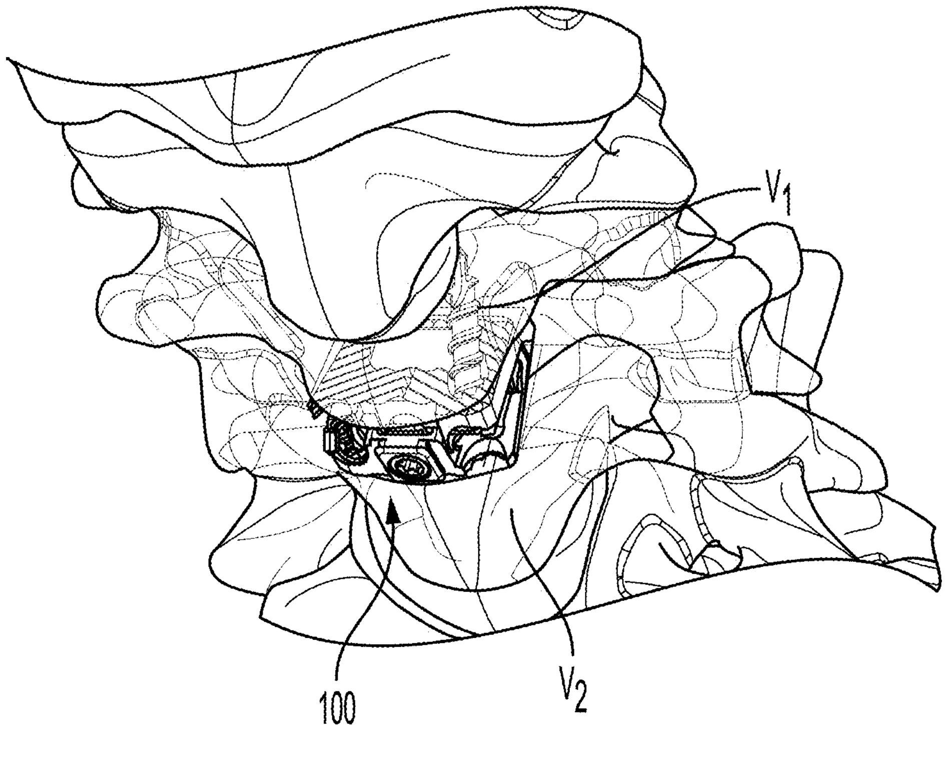
FIG. 20 is a perspective view of an expandable implant inserted between vertebrae.

Referring generally to FIGS. 18-20, various views of an expandable implant 100 installed between two vertebrae in an expanded position are illustrated. FIG. 18 is a side perspective view of an embodiment of an expandable implant 100 installed between two vertebrae $V_1$ and $V_2$. FIG. 19 is a front view showing the proximal end of an embodiment of an expandable implant 100 installed between two vertebrae $V_1$ and $V_2$. FIG. 20 is a perspective view of an embodiment of an expandable implant installed between two vertebrae $V_1$ and $V_2$.

Figure 21:
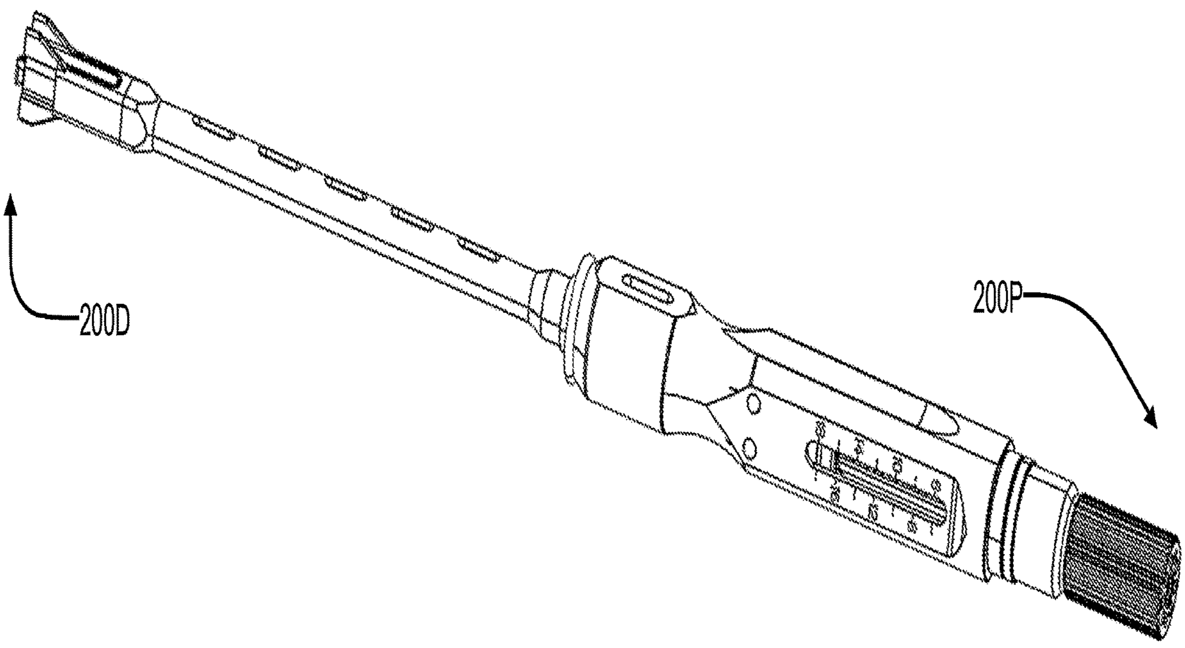
FIG. 21 is a perspective view of a surgical tool for use with disclosed expandable implants.
Figure 22:
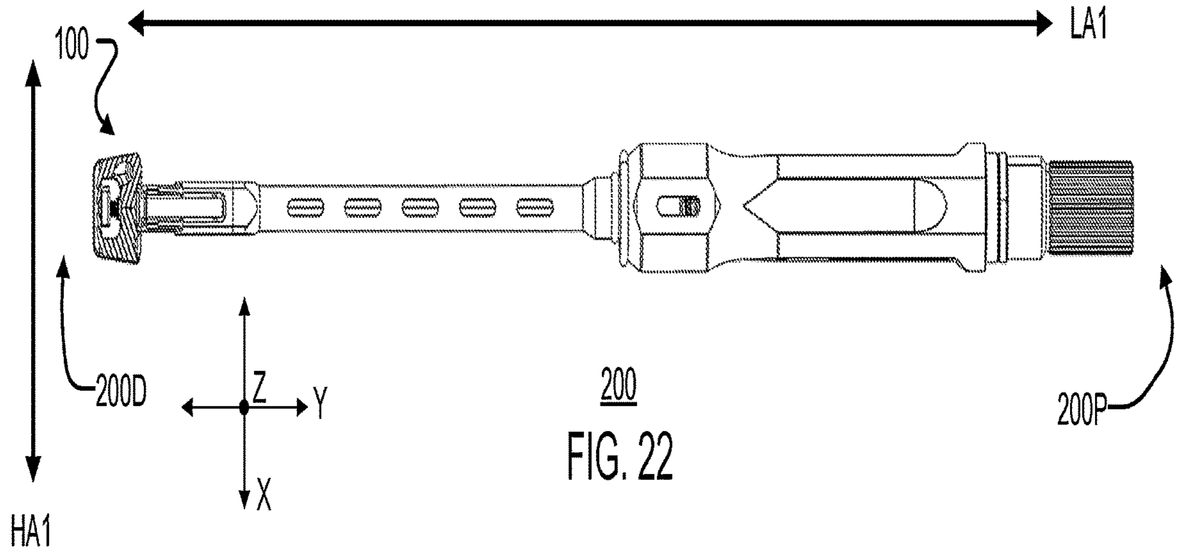
FIG. 22 is a top-down view of a surgical tool for use with disclosed expandable implants.
Figure 23:
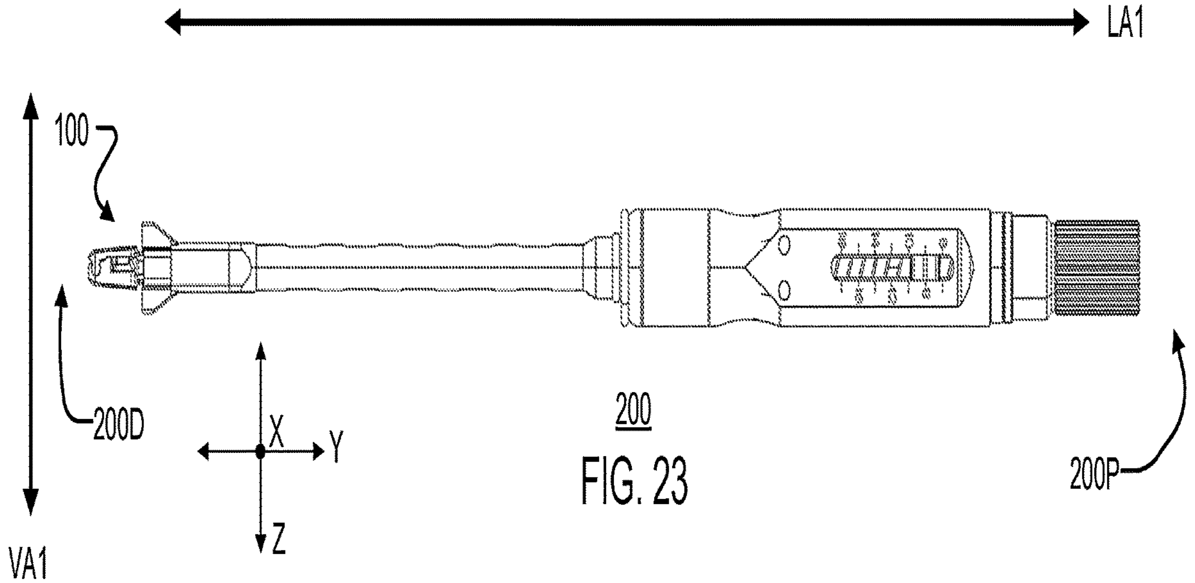
FIG. 23 is a side down view of a surgical tool for use with disclosed expandable implants.
Figure 24:
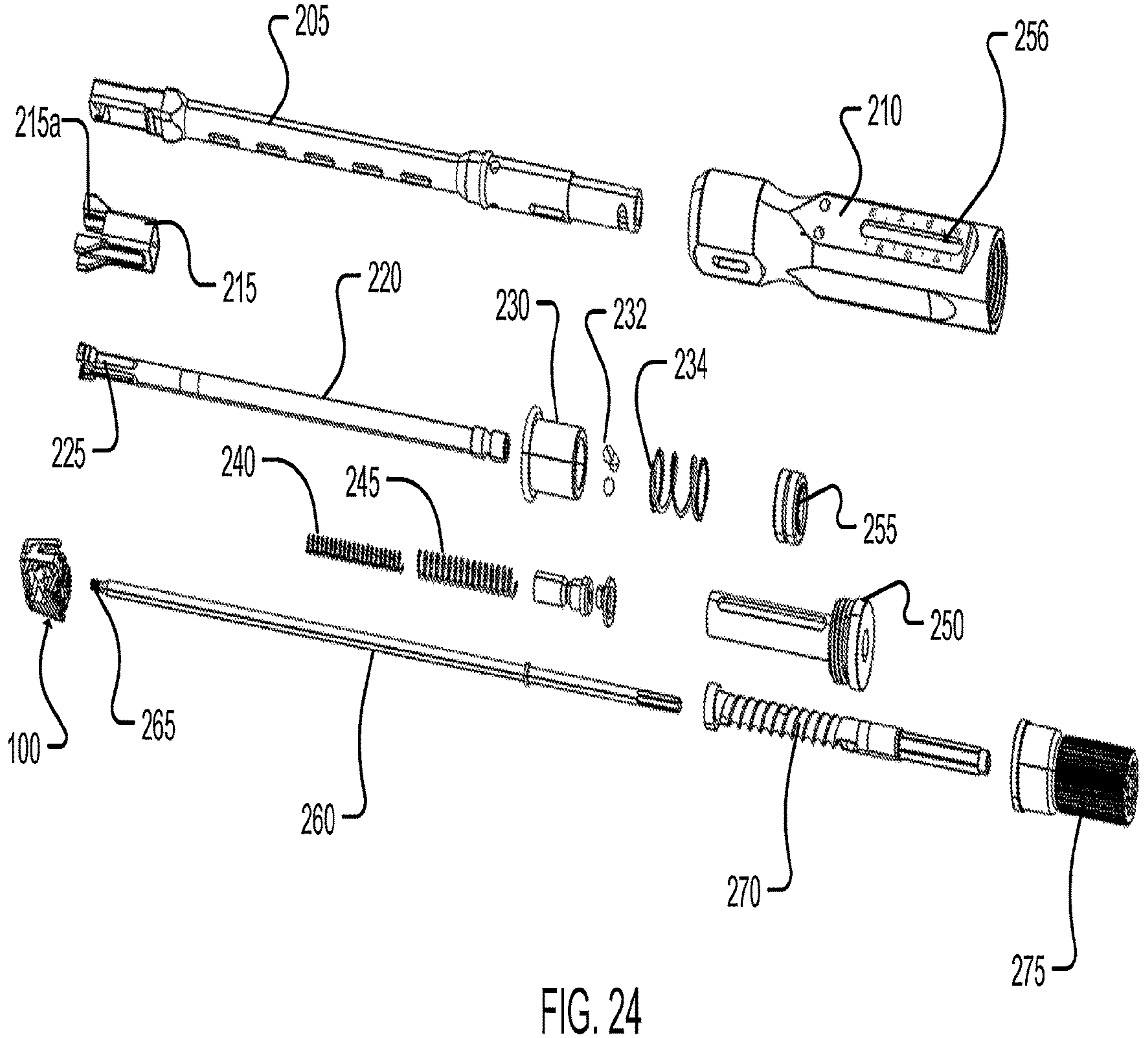
FIG. 24 is an exploded parts view of a surgical tool for use with disclosed implant embodiments.

Referring generally to FIGS. 21-24, a surgical tool 200 for use with disclosed expandable implants 100 is illustrated. FIG. 21 is a perspective view of surgical tool 200; FIG. 22 is a top-down perspective view of surgical tool 200; FIG. 23 is a side perspective view of surgical tool 200; and FIG. 24 is exploded parts view. In the example embodiment, surgical tool 200 may extend in a longitudinal direction LA1 from a proximal end 200P to a distal end 200D.

As shown in FIG. 24, the surgical tool 200 may include a jaw shaft assembly for coupling to the implant 100 and a drive shaft assembly for expanding the implant 100. In the example embodiment, an outer body 205 and a handle 210 house and/or support the components of the jaw shaft assembly and the drive shaft assembly. The jaw shaft assembly may comprise a plunger 220, a release actuator 230 for releasing jaw 225, positioning bearings 232, a biasing spring 234, a drive spring 240, and a plunger spring 245. The drive shaft assembly may comprise a drive shaft 260, turn shaft 270, angle indicator ring 255, zero adjustment knob 250, and turn knob 275.

Drive shaft 260 may extend through a hollow, central shaft of the plunger 220. In this way, plunger 220 may be coaxially aligned with and surround the drive shaft 260 and a drive end 265 may extend through the hollow shaft of plunger 220 and position the drive end 265 between the jaw 225. Additionally, the drive shaft 260 may be coupled to turn shaft 270 and may be independently rotatable relative to the plunger 220 by rotating the turn knob 275. For example, drive shaft 260 may be freely rotatable within the central hollow aperture of plunger 220. Additionally, plunger 220 may be independently translated in a longitudinal direction relative to drive shaft 260 by activating actuator 230. In various embodiments, drive shaft 260 is actionable by drive spring 240 and plunger 220 is actionable by plunger spring 245, both disposed at proximal portion of drive shaft 260. Generally, both the drive shaft 260 and plunger 220 will interact with and/or couple implant 100 as will be explained in further detail below.

A mounting jaw 225 for securely coupling to and uncoupling from implant 100 is located at the end of plunger 220 and defines the distal end of surgical tool 200. Mounting jaw 225 provides a latching mechanism for coupling with the gripping grooves 19, 29 of the inferior endplate 20 of implant 100 (see FIG. 25A). Plunger 220 may be disposed inside of outer body 205 and be linearly movable back and forth in the longitudinal direction. For example, a surgeon may slide actuator 230 which translates plunger 220 forward and backward in the longitudinal direction to effectuate horizontal opening and closing of the jaws 225. In some embodiments, surgical tool 200 may include a removable depth stop 215 that is sized to prevent an inadvertent over insertion of the coupled implant 100 into the disc space thereby preventing mounting jaw 225 from releasing implant 100. An additional advantage may be to facilitate the insertion of implant 100 at an appropriate target depth. The jaws **215*a* of depth stop 215 may be oriented such that a first jaw may contact the caudal vertebrae and the second jaw may contact the cephalad vertebrae. That is, each jaw of depth stop 215*a* may be perpendicularly oriented with respect to the mounting jaw 225 to control the insertion depth of the implant 100** into the target area.

Figure 25A:
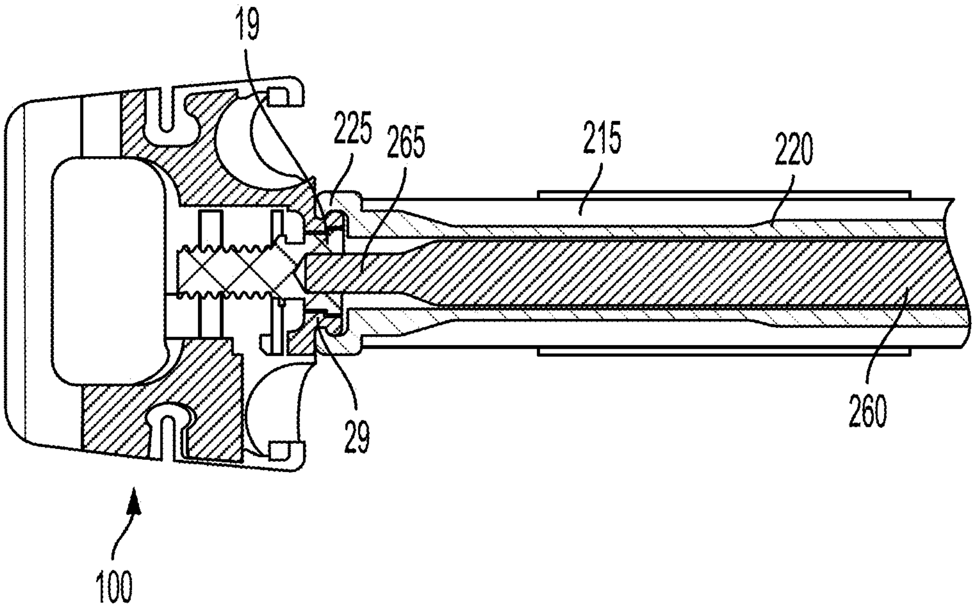
FIG. 25A is a cross section view showing a distal end of a surgical tool coupled with a disclosed implant embodiment.
Figure 25B:
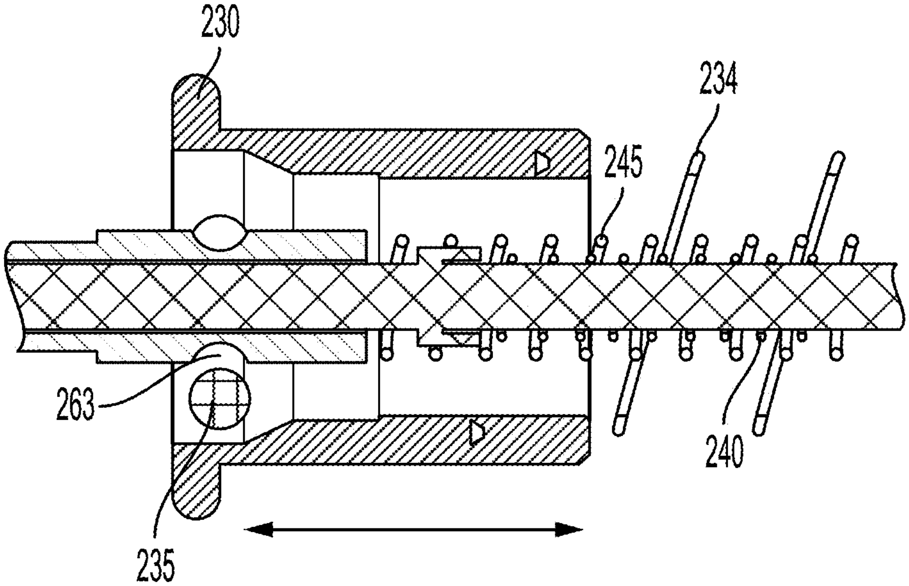
FIG. 25B is a cross section view showing a proximal end of a surgical tool coupled with a disclosed implant embodiment.

With reference to the cross-section perspective views of FIGS. 25A and 25B and the exploded parts view of FIG. 24 further details of the coupling process between surgical tool 200 and implant 100 will be disclosed. As seen in FIG. 25B, when actuator 230 is disposed in outer body 205 and is activated against biasing spring 234, the position bearings 235 disposed within the plunger groove 263 release into actuator 230 thereby releasing plunger 220 to move longitudinally in a distal direction by a biasing force applied by plunger spring 245 and splaying mounting jaw 225. In this "open" position, drive shaft end 265 of drive shaft 260 may be disposed within the hollow aperture of plunger 220 and move longitudinally in a distal direct by drive spring 240 to thereby engage with drive feature 53 at the proximal end of expansion screw 50. In various embodiments, drive shaft end 265 may have a size and shape that is designed to conform with the drive feature 53 of expansion screw 50. From the illustrated position of FIG. 25B, the plunger 220 is actuated longitudinally in the distal direction thereby retracting the mounting jaw 225 and engaging with gripping grooves 19, 29 of implant 100, i.e., implant 100 is brought towards surgical tool 200 (see FIG. 25A). In this fully engaged position, drive shaft 260 and plunger 220 are retracted longitudinally in the proximal direction thereby placing position bearings 235 back in plunger groove 263 thereby locking the actuator 230 and preventing inadvertent movement of plunger 220. In this "closed and locked" position, mounting jaw 225 is coupled with gripping grooves 19, 29 and drive end 265 is engaged with drive feature 53 of implant 100 such that implant 100 may be appropriately positioned and expanded.

Surgical tool 200 may include a second actuator in the form of a turn knob 275 that is securely coupled to a turn shaft 270. The turn shaft 270 may include a hollow space or aperture therein configured for disposal of drive shaft 260.

Figure 26A:
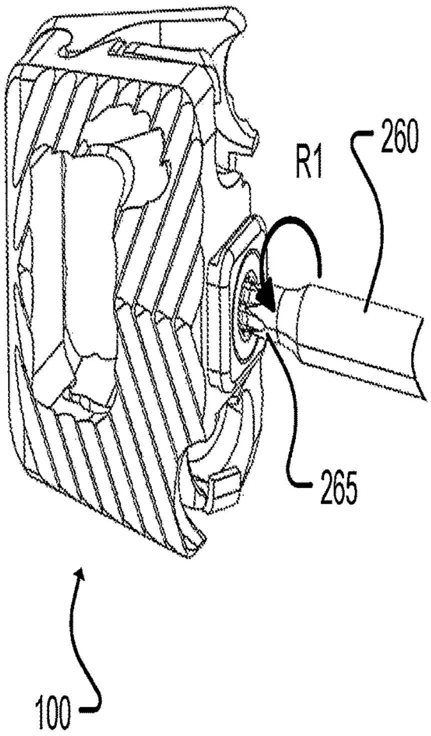
FIG. 26A is a perspective view showing a distal end of a surgical tool coupled with a disclosed implant embodiment.
Figure 26B:
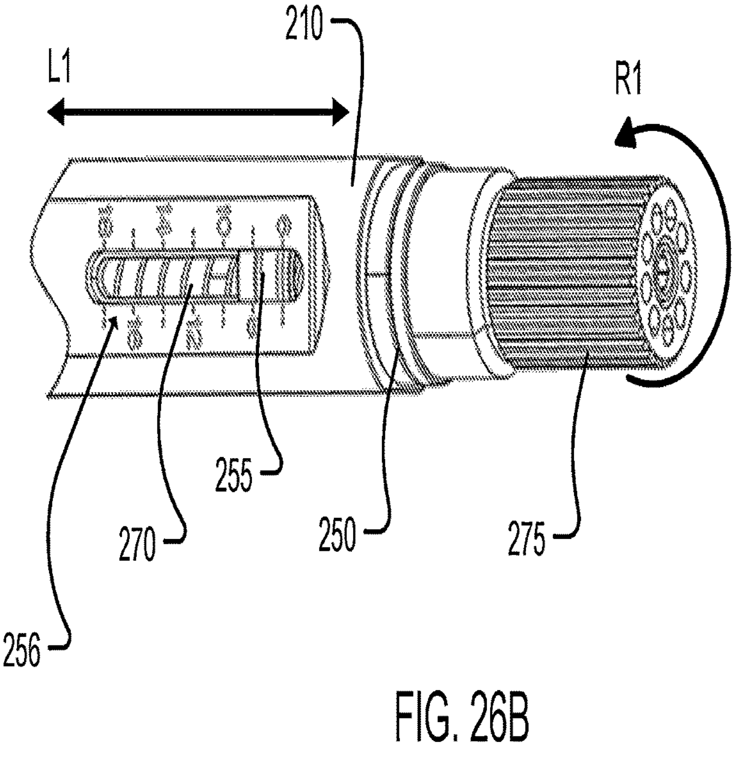
FIG. 26B is a perspective view showing the proximal end of a surgical tool coupled with a disclosed implant embodiment.

In this way, turn shaft 270 may be coupled to drive shaft 260 and each may rotate upon actuation of turn knob 275. FIGS. 26A and 26B show the distal and proximal ends of surgical tool 200 with mounting jaw 225 removed for ease of understanding and explanation of an expansion process.

As illustrated in FIG. 26A, once implant 100 is securely mated with surgical tool 200 via drive shaft 260, turn knob 275 may be actionable to rotate along the RI axis (see FIG. 26B) which, in turn, rotates the drive shaft 260 and drive shaft end 265 in the same RI rotation direction (see FIG. 26A). In this way, rotation of turn knob 275 may cause the turn shaft 270 and drive shaft 260 to rotate by an equal amount. In turn, external thread 51 of expansion screw 50 is threadably actuated in the threaded portion 31 thereby linearly translating wedge 30 in the proximal direction along channel 27 which extends along inferior endplate 20 (see FIG. 6). As wedge 30 is translated linearly along channel 27, wedge pin 32 rides along groove 28 and inclined surface 17 of superior endplate 10 thereby separating of superior endplate 10 from inferior endplate 20. For example, superior endplate 10 and inferior endplate 20 may pivotally separate away from one another at hinge member 40, which is disposed within arcuate channel 12.

At the distal end of surgical tool 200, turn knob 275 may be operatively coupled with turn shaft 270 which, in turn, is coupled with an angle indicator ring 255. Angle indicator ring 255 may be used to identify the angle of inclination a of which implant 100 is expanded. Angle indicator ring 255 may be slidable forward and backward along the threads of turn shaft 270 and be disposed inside of handle 210. In this way, rotation of turn knob causes the turn shaft 270 to rotate thereby linearly translating indicator ring 255 back and forth in the longitudinal direction to indicate the angle of inclination. A position of indicator ring 255 is visible through a window 256 in handle 210 which indicates the angle of inclination of the implant. In this way, the surgeon can rotate the expansion screw 50 the appropriate amount such that implant 100 is lordosed to a desired configuration.

Figure 27A:
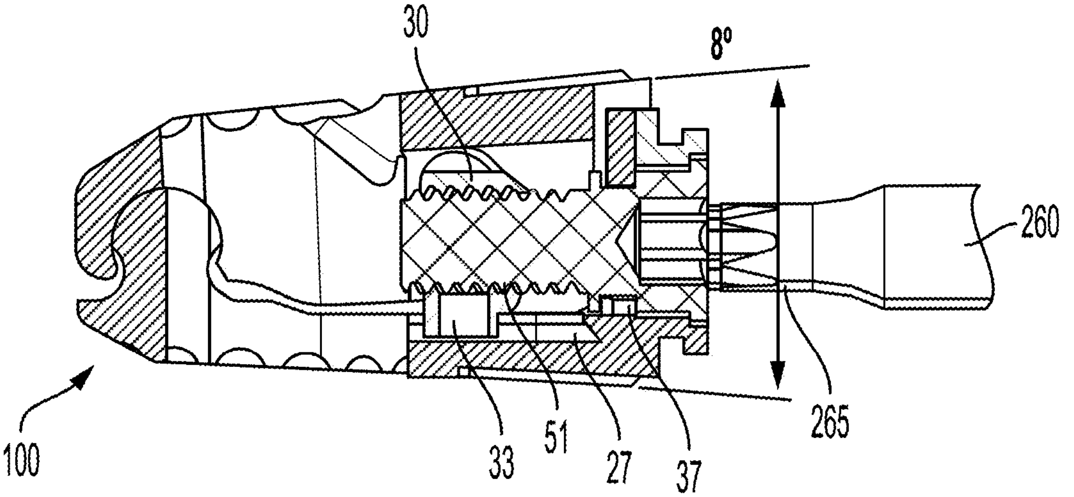
FIG. 27A is a side perspective of a distal end of a surgical tool coupled with a cross section view showing disclosed implant embodiment in a contracted position.
Figure 27B:
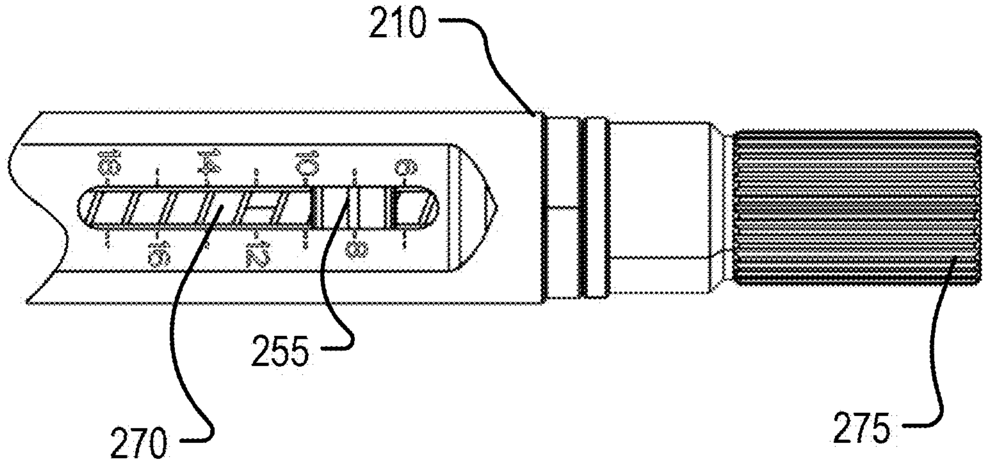
FIG. 27B is a side perspective of a proximal end of a surgical tool coupled with a disclosed implant embodiment in a contracted position.
Figure 28A:
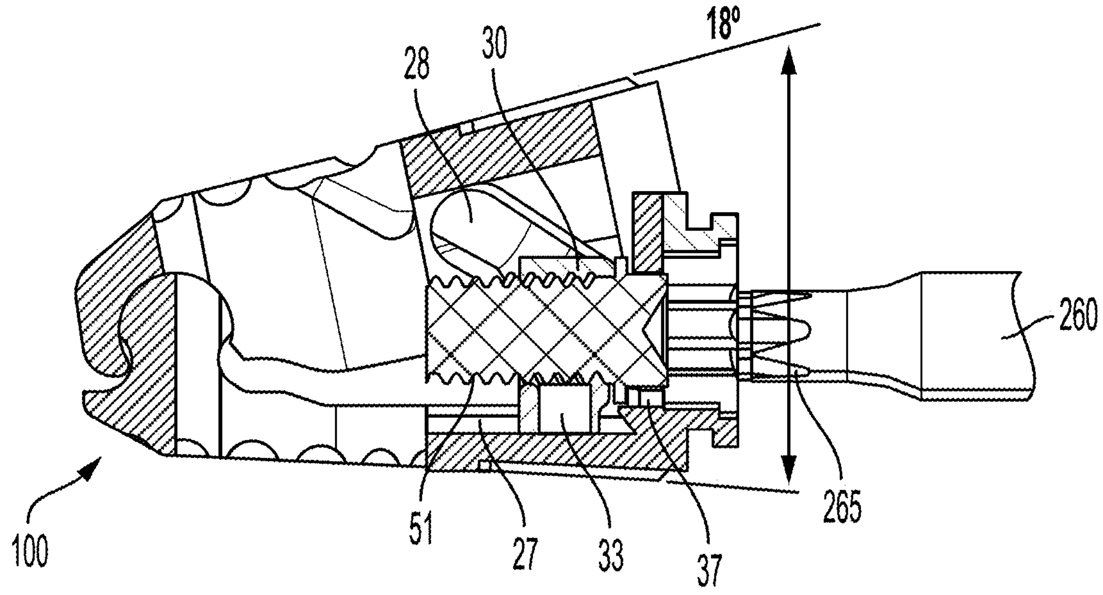
FIG. 28A is a side perspective of a distal end of a surgical tool coupled with a cross section view showing disclosed implant embodiment in an expanded position.
Figure 28B:
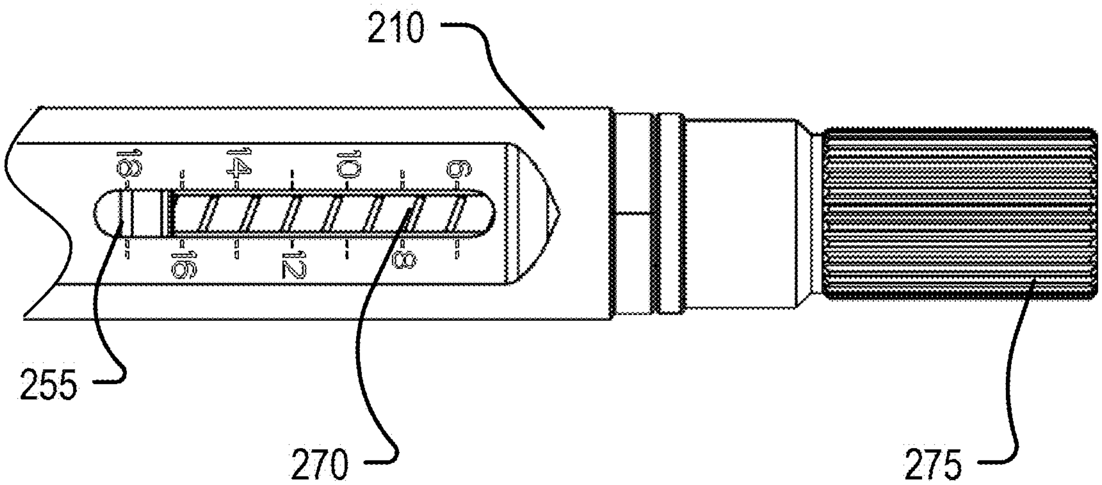
FIG. 28B is a side perspective of a proximal end of a surgical tool coupled with a disclosed implant embodiment in an expanded position.

With reference to FIGS. 27A and 27B, drive end 260 of surgical tool 200 is mated to an expandable implant 100 in a closed configuration is disclosed. FIG. 27A shows an implant 100 in a contracted, or a neutral configuration having 8° angle of inclination. Accordingly, the angle indicator 255 coupled to turn shaft 270 disposed in handle 210 shows 8° verifying angle of coupled implant 100 (see FIG. 27B). In the example embodiment in FIGS. 28A and 28B, implant 100 is illustrated in an expanded configuration. Similarly, in this expanded configuration, the angle of inclination of expanded implant 100 is 18° and verified by angle indicator 255. In order to account for implants of varying sizes, surgical tool 200 may be provided with a zero adjustment knob 250 to calibrate the angle indicator ring 255 for differently sized implants. For example, zero adjustment knob 250 may be utilized to calibrate or "zero" the indicator angle for the appropriate implant. In one example, a surgeon would "zero" the indicator angle immediately prior to beginning an expansion process based on a known size and pivoting rate of expansion of implant 100.

A method of operation for expanding an intervertebral implant to a desired angle of inclination will now be discussed. First, a surgeon may couple implant 100 to the surgical tool 200 by operating the actuator 230 thereby splaying open the jaws 225 (see FIGS. 25A, 25B). In this splayed configuration, the exposed drive end 265 may be mated with drive feature 53 of expansion screw 50. Once implant 100 is in the operatively engaged position with drive shaft end 265, mounting jaw 225 may grasp onto gripping grooves 19, 29 for securely engaging surgical tool 200 with implant 100. In this closed configuration, a surgeon may insert implant 100 into the disc space between superior (cephalad) and inferior (caudal) vertebrae, for example. Prior to beginning the expansion process the surgeon may "zero" or calibrate the angle indicator dial by zero adjustment knob 250 as explained above. After the implant 100 is positioned between the superior and inferior vertebrae, a surgeon may rotate turn knob 275 along RI axis rotating the drive shaft 260 and drive shaft end 265 and thereby threadably translating wedge 30 along groove 28 and inclined surface 17 separating the superior endplate 10 apart from the inferior endplate 20. In some embodiments, turn knob 275 may include a torque limiting feature to ensure that expansion screw is tight enough to hold the implant in the expanded configuration but not too tight that shearing might occur.

In various embodiments, a surgeon may verify the expanded angle of implant by the angle indicator ring 255. Once implant 100 is inserted and expanded to the desired configuration, a surgeon may disengage jaw 225 from gripping grooves 19, 29 by activating the actuator 230 to splay the jaw 225 horizontally and releasing from gripping grooves 19, 29. Those with skill in the art will appreciate that the splaying of the jaws horizontally away from one another vs. vertically away from one another is critical to prevent the jaws from being obstructed by the adjacent superior and inferior vertebrae. After disengaging the jaw 225, a surgeon may disengage drive end 265 from drive feature 53 of the expansion screw 50 thereby separating surgical tool 200 from inserted and expanded implant 100.

A method of anchoring or locking an intervertebral implant in a desired angle of inclination within vertebral disc will now be discussed. Once an intervertebral implant is inserted and expanded to a desired angle of inclination in the disc space, a surgeon may lock the superior endplate 10 and inferior endplate 20 in the desired configuration.

At this stage, a surgeon may insert a first bone screw 97 across cutout 25 of inferior endplate 20 and through a first bone screw aperture 11 of superior endplate 10 to operatively anchor second bone screw to superior vertebra. Similarly, a surgeon may insert a second bone screw 97 across cutout 18 of superior endplate 10 and through a second bone screw aperture 21 of inferior endplate 20 to operatively anchor second bone screw 97 to inferior vertebra (FIGS. 13, 14). In some embodiments, a first bone screw retention mechanism 13 is disposed in the corresponding cavity 14 of superior endplate 100 on a first lateral side 100L of implant 100. Similarly, a second bone screw retention mechanism 23 is disposed in the corresponding cavity 24 of inferior endplate 20 on a second lateral side 100L of implant 100. When a surgeon drives bone screw 97 into inclined surface of bone screw aperture 11, 21, hook portion 13*b*, 23*b* of bone screw retention mechanism 13, 23 may flex away from the bone screw aperture 11, 21 such that bone screws 97 drives through inclined surface of bone screw aperture 11, 21 and anchors to superior and inferior vertebrae. Thereafter, when bone screw 97 is fully inserted, hook portion 13*b*, and 23*b* may flex back towards bone screw aperture 11, 21 such that it will prevent bone crews 97 from backing out fully thereby anchoring implant 100 to superior and inferior vertebrae. In various embodiments, a surgeon may vary bone screw trajectory 99 by +/−γ degrees depending on size and the alignment of cephalad and caudal vertebrae to optimally anchor bone screws 97 to each vertebra (see FIG. 15).

Figure 29:
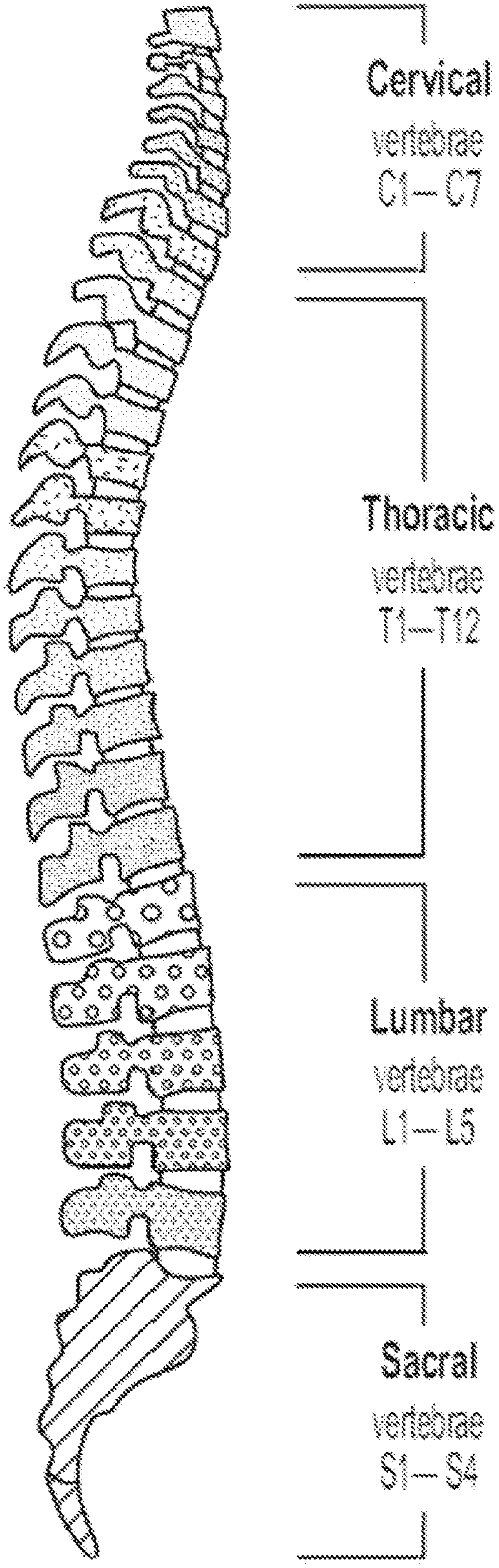
Figure 30:
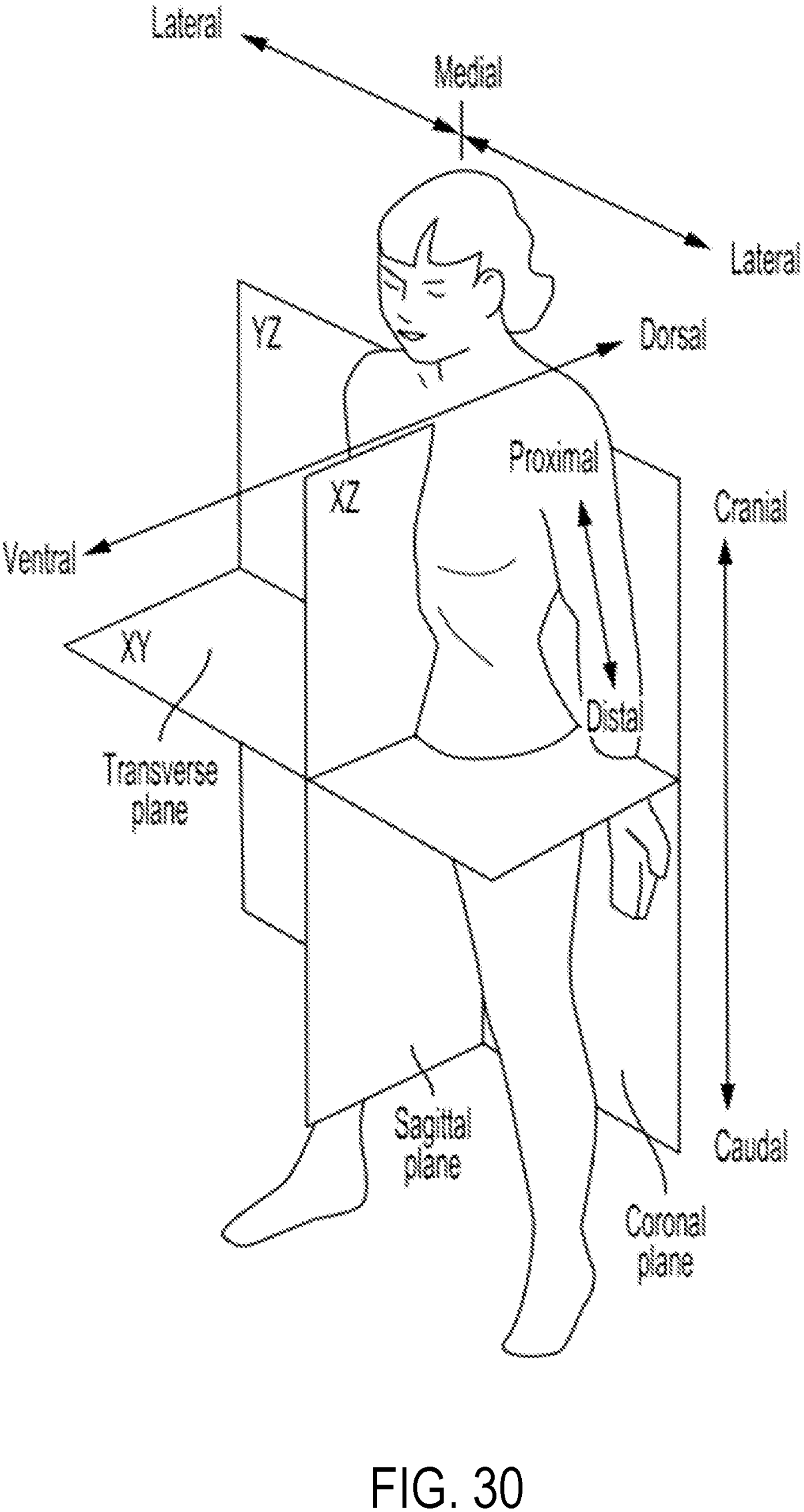
FIG. 30 is a reference drawing showing various planes and reference directions of which the various disclosed implant embodiments may move in or act in with respect to a patient.

FIG. 29 is a reference drawing showing the human spine of which various disclosed implant embodiments may be installed in. FIG. 30 is a reference drawing showing various planes and reference directions of which the various disclosed implant embodiments may move in or act in with reference to a patient 1.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

The techniques of this disclosure may also be described in the following examples.

Example 1: An expandable implant (100) movable between a contracted position and an expanded position, comprising:

a body extending from a proximal end to a distal end in a proximal-to-distal direction and extending from a first lateral side to a second lateral side in a widthwise direction, the expandable body being defined by a superior endplate (10) and an inferior endplate (20) that are pivotally connected; the superior endplate includes a ramp (16) that comprises an inclined surface (17); the inferior endplate comprises support frame (15) inside surface including a channel (27), wherein the support frame includes a frame portion having a proximal surface and a distal surface, wherein an aperture extends through the proximal surface and the distal surface;

a wedge (30) disposed between the superior endplate and the inferior endplate, the wedge including: a bearing surface on an upper end thereof configured to slide across the inclined surface of the ramp and a tang (33) on a lower end thereof configured for disposal within the channel; and an expansion screw (50) extending through the aperture and being operatively coupled to a threaded portion (31) of the wedge, wherein rotation of the expansion screw is configured to linearly translate the wedge in a longitudinal direction;

wherein proximal movement of the wedge cause the superior endplate to rotate away from the inferior endplate.

Example 2: The expandable implant of example 1, further comprising:

a groove (28) disposed on an interior sidewall of the superior endplate, and a pin (32) extending from the wedge and being configured to slide within the groove upon linear movement of the wedge, wherein the pin and the wedge are configured to prevent an overexpansion of the implant and to maintain an angular position of the superior endplate.

Example 3: The expandable implant of example 1, further comprising:

a recess (37) formed within the support frame portion, and wherein a head portion of the expansion screw resides within the recess.

Example 4: The expandable implant of example 3, further comprising:

a retaining clip (35) seated within the recess, the retaining clip being coupled to a groove portion (52) of the expansion screw, and wherein the retaining clip is configured to prevent the expansion screw from linearly translating while permitting the expansion screw to rotate; and wherein the retaining clip is configured to provide friction on the expansion screw to prevent the expansion screw from inadvertently rotating after insertion and expansion of the expandable implant.

Example 5: The expandable implant of example 1, further comprising:

at least one bone screw aperture (11, 21) extending through one of the superior endplate or the inferior endplate; and at least one retention tab (13, 23) having a hook portion (**13*b*, 23*b*) and an anchor portion (13*a*, 23*a*), wherein the at least one retention tab is configured to automatically deflect away from the at least one bone screw aperture during installation of a corresponding bone screw (97**) and return to a retaining position upon full seating of the bone screw within the at least one bone screw aperture.

Example 6: The expandable implant of example 1, further comprising: a first bone screw aperture (11) extending through the superior endplate;

a second bone screw aperture (21) extending through the inferior endplate;

a first retention tab (13) having a first hook (**13*b*) portion and a first anchor portion (13*a*), the first retention tab being configured to: (a) cover at least a portion of the first bone screw aperture in a neutral position, and (b) deflect away from the neutral position upon driving of a first bone screw into the first bone screw aperture when a head portion of the first bone screw contacts an inclined surface of the first hook portion; and a second retention (23) tab having a second hook (23*b*) portion and a second anchor portion (23*a***), the second retention tab being configured to: (a) cover at least a portion of the second bone screw aperture in a neutral position, and (b) deflect away from the neutral position upon driving of a second bone screw into the second bone screw aperture when a head portion of the second bone screw contacts an inclined surface of the second hook portion.

Example 7: The expandable implant of example 1, wherein the frame portion further comprises a first gripping groove (19) and a second gripping groove (29).

Example 8: The expandable implant of example 7, wherein:

the first gripping groove comprises a notch on one lateral side of the frame portion; and the second gripping groove comprises a notch on an opposite lateral side of the frame portion.

Example 9: The expandable implant of example 1, wherein:

the superior endplate comprises a first plurality of engagement features (39) that are angled about 20 degrees to about 40 degrees with respect to a proximal end of the superior endplate; and the inferior endplate comprises a second plurality of engagement features (39) that are angled about 20 degrees to about 40 degrees with respect to a proximal end of the inferior endplate.

Example 10: The expandable implant of example 1, wherein the channel extends in the proximal-to-distal direction and has a size and shape generally corresponding to a size and shape of the tang to couple the wedge within the channel.

Example 11: The expandable implant of example 1, wherein: the expansion screw comprises a threaded portion (51) at a distal end, a drive feature portion at proximal end (53), and a groove portion connecting the threaded portion and the drive feature portion, and a retaining clip is coupled to the groove portion.

Example 12: The expandable implant of example 1, wherein:

the superior endplate comprises a first bone screw aperture configured to orient a first bone screw in a cephalad direction and a first bone screw relief cutout (18); and the inferior endplate comprises a second bone screw aperture configured to orient a second bone screw in a caudal direction and a second bone screw relief cutout (25), wherein the first bone screw relief cutout is configured to provide additional clearance to the second bone screw during an installation process and the second bone screw relief cutout is configured to provide additional clearance to the first bone screw during an installation process.

Example 13: The expandable implant of example 1, further comprising V-shaped engagement features (39).

Example 14: The expandable implant of example 1, further comprising a handle (210) with a window (256).

Example 15: The expandable implant of example 1, further comprising:

a surgical tool (200) for inserting the expandable implant and moving the expandable implant from the contracted position to the expanded position, the surgical tool comprising:

a plunger (220) having a mounting jaw end (225) that is engaged by a jaw release actuator (230);

wherein activating the jaw release actuator moves the mounting jaw to an open configuration greater than a distance between the first gripping groove and the second gripping groove of the frame portion of the expandable implant;

a drive shaft (260) disposed within the plunger having a drive end (265) configured to engage a drive feature of the expansion screw;

wherein the jaw release actuator is configured to engage with the first gripping groove and the second gripping groove by pushing the drive shaft against the expansion screw;

a turn shaft (270) coupled to the drive shaft configured to rotate the drive shaft by actuation of a turn knob handle (275) coupled the turn shaft;

wherein actuating the turn knob handle rotates the drive shaft and the expansion screw to cause the superior endplate to pivotally separate away from the inferior endplate;

an angle indicator ring (275) operatively coupled with the turn shaft, wherein rotation of the drive shaft translates the angle indicator ring along the turn shaft thereby incrementally identifying a corresponding angle of expansion of the expandable implant throughout rotation of the turn shaft;

a depth stop (215) coupled perpendicularly to the mounting jaw;

wherein the depth stop is configured to engage surrounding vertebrae and prevent over-insertion of the expandable implant thereby preventing the mounting jaw from releasing the implant;

an outer body (205) extending through the plunger and the drive shaft; and a handle (210) enclosing the turn shaft and the angle indicator ring.

Various examples of the disclosure have been described. These and other examples are within the scope of the following claims.

What is claimed is:

1. An expandable implant movable between a contracted position and an expanded position, comprising:

a body extending from a proximal end to a distal end in a proximal-to-distal direction and extending from a first lateral side to a second lateral side in a widthwise direction, the body being defined by a superior endplate and an inferior endplate that are pivotally connected;

wherein the superior endplate includes an inside surface that comprises an inclined ramp;

wherein the inferior endplate comprises a support frame, an inside superior-facing surface including a channel, wherein the support frame includes a frame portion having a proximal surface and a distal surface, wherein an aperture extends through the proximal surface and the distal surface;

wherein a distal end of the inferior endplate comprises a hinge member that is disposed within an arcuate channel of the superior endplate, the hinge member forming a single pivoting axis between the superior endplate and the inferior endplate;

a groove disposed on an interior sidewall of the superior endplate;

a wedge disposed between the superior endplate and the inferior endplate, the wedge including: a bearing surface on an upper end thereof configured to slide across the inclined ramp and a tang positioned opposite the bearing surface on a lower end thereof configured for disposal within the channel;

a pin extending from the wedge and being configured to slide within the groove upon linear movement of the wedge, wherein the pin and the wedge are configured to prevent an overexpansion of the implant about the single pivoting axis and to maintain an angular position of the superior endplate relative to the inferior endplate; and an expansion screw extending through the aperture and being operatively coupled to a threaded portion of the wedge, wherein the expansion screw is configured to rotate and thereby linearly translate the wedge in a longitudinal direction;

wherein proximal movement of the wedge causes the superior endplate to rotate away from the inferior endplate.

2. The expandable implant of claim 1, further comprising:

a recess formed within the support frame portion, and wherein a head portion of the expansion screw resides within the recess.

3. The expandable implant of claim 2, further comprising:

a retaining clip seated within the recess, the retaining clip being coupled to a groove portion of the expansion screw;

wherein the retaining clip is configured to prevent the expansion screw from linearly translating while permitting the expansion screw to rotate; and wherein the retaining clip is configured to provide friction on the expansion screw to prevent the expansion screw from inadvertently rotating after insertion and expansion of the expandable implant.

4. The expandable implant of claim 1, further comprising:

at least one bone screw aperture extending through one of the superior endplate or the inferior endplate; and at least one retention tab having a hook portion and an anchor portion;

wherein the at least one retention tab is configured to automatically deflect away from the at least one bone screw aperture during installation of a corresponding bone screw and return to a retaining position upon full seating of the bone screw within the at least one bone screw aperture.

5. The expandable implant of claim 1, further comprising:

a first bone screw aperture extending through the superior endplate;

a second bone screw aperture extending through the inferior endplate;

a first retention tab having a first hook portion and a first anchor portion, the first retention tab being configured to: (a) cover at least a portion of the first bone screw aperture in a neutral position, and (b) deflect away from the neutral position upon driving of a first bone screw into the first bone screw aperture when a head portion of the first bone screw contacts an inclined surface of the first hook portion; and a second retention tab having a second hook portion and a second anchor portion, the second retention tab being configured to: (a) cover at least a portion of the second bone screw aperture in a neutral position, and (b) deflect away from the neutral position upon driving of a second bone screw into the second bone screw aperture when a head portion of the second bone screw contacts an inclined surface of the second hook portion.

6. The expandable implant of claim 1, wherein the frame portion further comprises a first gripping groove and a second gripping groove, wherein:

the first gripping groove comprises a notch on one lateral side of the frame portion; and the second gripping groove comprises a notch on an opposite lateral side of the frame portion.

7. The expandable implant of claim 1, wherein:

the superior endplate comprises a first plurality of engagement features that are angled about 20 degrees to about 40 degrees with respect to a proximal end of the superior endplate; and the inferior endplate comprises a second plurality of engagement features that are angled about 20 degrees to about 40 degrees with respect to a proximal end of the inferior endplate.

8. The expandable implant of claim 1, wherein the channel extends in the proximal-to-distal direction and has a size and shape generally corresponding to a size and shape of the tang to couple the wedge within the channel.

9. The expandable implant of claim 1, wherein: the expansion screw comprises a threaded portion at a distal end, a drive feature portion at proximal end, and a groove portion connecting the threaded portion and the drive feature portion, and a retaining clip is coupled to the groove portion.

10. The expandable implant of claim 1, wherein:

the superior endplate comprises a first bone screw aperture configured to orient a first bone screw in a cephalad direction and a first bone screw relief cutout; and the inferior endplate comprises a second bone screw aperture configured to orient a second bone screw in a caudal direction and a second bone screw relief cutout;

wherein the first bone screw relief cutout is configured to provide additional clearance to the second bone screw during an installation process and the second bone screw relief cutout is configured to provide additional clearance to the first bone screw during an installation process.

11. The expandable implant of claim 1, wherein the channel is positioned behind the support frame and extends along a medial portion of the inside lower surface in a proximal-to-distal direction such that the tang linearly slides within the channel thereby linearly translating the wedge in the longitudinal direction.

12. A system including a medical implant and a surgical tool, the system comprising:

an expandable implant movable between a contracted position and an expanded position, comprising:

a body extending from a proximal end to a distal end in a proximal-to-distal direction and extending from a first lateral side to a second lateral side in a widthwise direction, the expandable body being defined by a superior endplate and an inferior endplate that are pivotally connected;

the superior endplate includes an inside surface that comprises an inclined ramp;

the inferior endplate comprises a support frame, an inside superior-facing surface including a channel, and a frame portion having a proximal surface and a distal surface, wherein an aperture extends through the proximal surface and the distal surface of the frame portion;

wherein a distal end of the inferior endplate comprises a hinge member that is disposed within an arcuate channel of the superior endplate, the hinge member forming a single pivoting axis between the superior endplate and the inferior endplate;

a groove disposed on an interior sidewall of the superior endplate;

a wedge disposed between the superior endplate and the inferior endplate, the wedge including: a bearing surface on an upper end thereof configured to slide across the inclined ramp and a tang positioned opposite the bearing surface on a lower end thereof configured for disposal within the channel;

a pin extending from the wedge and being configured to slide within the groove upon linear movement of the wedge, wherein the pin and the wedge are configured to prevent an overexpansion of the implant about the pivoting axis and to maintain an angular position of the superior endplate relative to the inferior endplate; and an expansion screw extending through the aperture and being operatively coupled to the wedge;

wherein the expansion screw is configured to rotate and thereby linearly translate the wedge in a longitudinal direction; and a surgical tool for moving the expandable implant from the contracted position to the expanded position;

wherein rotation of a driver of the surgical tool causes the wedge to move proximally and causes the superior endplate to rotate away from the inferior endplate.

13. The system of claim 12, wherein:

the inferior endplate comprises a first gripping groove located at a first lateral side of the frame portion, and a second gripping groove located at a second lateral side of the frame portion;

the surgical tool comprises a mounting jaw configured to engage with the first gripping groove and the second gripping groove; and wherein in an insertion configuration, the first gripping groove and the second gripping groove of the expandable implant are engaged by the mounting jaw of the surgical tool.

14. The system of claim 13, wherein the surgical tool comprises:

a plunger having a jaw actuator configured to cause the mounting jaw to affirmatively engage and disengage with the gripping grooves of the expandable implant;

wherein activating the jaw actuator moves the mounting jaw to an open configuration by a distance that is greater than a distance between the first gripping groove and the second gripping groove of the frame portion of the expandable implant;

a drive shaft disposed within the plunger having a drive end configured to engage a drive feature of the expansion screw;

wherein the jaw actuator is configured to engage with the first gripping groove and the second gripping groove by pushing the drive shaft against the expansion screw;

a turn shaft coupled to the drive shaft and being configured to rotate the drive shaft by actuation of a turn knob coupled to the turn shaft;

wherein actuating the turn knob rotates the drive shaft and the expansion screw to cause the superior endplate to pivotally separate away from the inferior endplate;

an angle indicator ring operatively coupled with the turn shaft;

wherein rotation of the drive shaft translates the angle indicator ring along the turn shaft thereby incrementally identifying a corresponding angle of expansion of the expandable implant throughout rotation of the turn shaft;

an outer body surrounding the plunger and the drive shaft; and a handle enclosing the turn shaft and the angle indicator ring.

15. The system of claim 14, wherein rotation of the expansion screw causes the wedge disposed in the channel to slide within the inferior endplate towards the proximal end of the expandable implant thereby causing the bearing surface of the wedge to engage the inclined ramp to separate the superior endplate from the inferior endplate along a pivoting axis.

16. The system of claim 15 further comprising a depth stop coupled perpendicularly to the mounting jaw, the depth stop configured to engage surrounding vertebrae and prevent over-insertion of the expandable implant thereby preventing the mounting jaw from releasing the implant.

17. The system of claim 16, wherein an expanded angle between the superior endplate from the inferior endplate is identified by indicator ring of the surgical tool.

18. The system of claim 17, further comprising a retaining clip engaged in a recess of the frame portion, wherein the retaining clip is configured to engage a corresponding slot of the expansion screw to prevent the expansion screw from linearly translating while permitting the expansion screw to be rotated by a driver.

19. The system of claim 18, wherein the retaining clip is configured to provide friction on the expansion screw to prevent the expansion screw from inadvertently rotating in absence of the driver preventing unwanted expansion and contraction of the implant after insertion and expansion.

* * * * *